(12) United States Patent
Hong et al.

(10) Patent No.: US 11,515,366 B2
(45) Date of Patent: Nov. 29, 2022

(54) DISPLAY DEVICE

(71) Applicant: Samsung Display Co., Ltd., Yongin-si (KR)

(72) Inventors: Won Ki Hong, Suwon-si (KR); So Hee Park, Cheonan-si (KR); Hee Seomoon, Hwaseong-si (KR); Hyeon Jun Lee, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 101 days.

(21) Appl. No.: 17/087,501

(22) Filed: Nov. 2, 2020

(65) Prior Publication Data

US 2021/0296408 A1 Sep. 23, 2021

(30) Foreign Application Priority Data

Mar. 18, 2020 (KR) ........................ 10-2020-0033099

(51) Int. Cl.
*G09G 5/00* (2006.01)
*H01L 27/32* (2006.01)
*A61B 5/00* (2006.01)

(52) U.S. Cl.
CPC ........ *H01L 27/3227* (2013.01); *A61B 5/0053* (2013.01); *H01L 27/323* (2013.01); *A61B 2562/0247* (2013.01)

(58) Field of Classification Search
USPC ........................................ 345/156, 173, 174
See application file for complete search history.

(56) References Cited

U.S. PATENT DOCUMENTS

| 11,171,184 | B2 * | 11/2021 | Lee | H05K 1/189 |
| 2015/0185912 | A1 * | 7/2015 | Lee | G06F 3/0412 |
| | | | | 345/174 |
| 2016/0310027 | A1 * | 10/2016 | Han | A61B 5/6898 |
| 2017/0119307 | A1 * | 5/2017 | Shim | A61B 5/0022 |
| 2017/0281024 | A1 | 10/2017 | Narasimhan et al. | |
| 2017/0360306 | A1 | 12/2017 | Narasimhan et al. | |
| 2017/0372114 | A1 * | 12/2017 | Cho | G06F 3/0412 |
| 2019/0043420 | A1 * | 2/2019 | Jung | G09G 3/3225 |
| 2019/0095005 | A1 * | 3/2019 | Lee | G06F 3/044 |
| 2019/0123113 | A1 * | 4/2019 | Kim | H01L 27/323 |
| 2019/0266379 | A1 * | 8/2019 | Huang | G06V 40/13 |
| 2020/0026335 | A1 | 1/2020 | Lee et al. | |
| 2020/0057523 | A1 * | 2/2020 | Park | G06F 3/0412 |
| 2020/0058712 | A1 * | 2/2020 | Lee | H01L 27/323 |

(Continued)

FOREIGN PATENT DOCUMENTS

CN 110060578 A 7/2019
EP 3 788 950 A1 3/2021

(Continued)

*Primary Examiner* — Thuy N Pardo
(74) *Attorney, Agent, or Firm* — Lewis Roca Rothgerber Christie LLP

(57) ABSTRACT

A display device includes a display panel comprising a through hole and a pixel area, the pixel area surrounding the through hole and including pixels for displaying an image; a force sensor at a first surface of the display panel and configured to sense force applied from an outside; and a light sensor overlapping the through hole of the display panel in a thickness direction of the display panel, the light sensor being configured to sense light incident on the light sensor through the through hole.

20 Claims, 38 Drawing Sheets

(56) References Cited

U.S. PATENT DOCUMENTS

| | | | | |
|---|---|---|---|---|
| 2020/0173856 A1* | 6/2020 | Hai | .................... | H01L 51/5012 |
| 2020/0202099 A1* | 6/2020 | Sun | ........................ | H01L 51/56 |
| 2020/0301541 A1* | 9/2020 | Jeon | ..................... | G06F 1/1643 |
| 2020/0343311 A1* | 10/2020 | Li | ....................... | G06V 40/1318 |
| 2020/0348779 A1* | 11/2020 | Lee | ........................ | G06F 3/041 |
| 2020/0364434 A1* | 11/2020 | Bok | ................... | G06V 40/1318 |
| 2020/0382739 A1* | 12/2020 | Lu | ........................ | G02F 1/13318 |
| 2021/0067618 A1 | 3/2021 | Hong et al. | | |
| 2021/0233973 A1* | 7/2021 | Han | ..................... | H01L 27/3227 |
| 2021/0271916 A1* | 9/2021 | Lius | ........................ | G06F 3/041 |
| 2021/0349568 A1* | 11/2021 | Park | ................... | G06F 3/04142 |

FOREIGN PATENT DOCUMENTS

| | | |
|---|---|---|
| KR | 10-2017-0111827 A | 10/2017 |
| KR | 10-2021-0028302 | 3/2021 |

\* cited by examiner

DISPLAY DEVICE

CROSS-REFERENCE TO RELATED APPLICATION

This application claims priority to and the benefit of Korean Patent Application No. 10-2020-0033099, filed on Mar. 18, 2020, in the Korean Intellectual Property Office (KIPO), the entire content of which is incorporated by reference herein.

BACKGROUND

1. Field

The present disclosure relates to a display device.

2. Description of the Related Art

A display device is a device for displaying an image on a screen and may be used not only as a television (TV) or a monitor but also as a portable smartphone or a tablet personal computer (PC). A portable display device is equipped with various functions. For example, a camera and a fingerprint sensor may be included in the display device.

With the recent spotlight on the healthcare industry, methods of more easily obtaining biometric information about health are being developed. For example, attempts are being made to make a conventional oscillometric blood pressure measurement device into a portable blood pressure measurement device. However, the portable blood pressure measurement device itself may use an independent light source, sensor, and display, and may be carried separately in addition to a smartphone or a tablet PC.

SUMMARY

Aspects of some example embodiments of the present disclosure are directed toward a display device having a blood pressure measurement function.

However, example embodiments of the present disclosure are not limited to those set forth herein. The above and other example embodiments of the present disclosure will become more apparent to one of ordinary skill in the art to which the present disclosure pertains by referencing the detailed description of the present disclosure given below.

According to some example embodiments of the present disclosure, there is provided a display device comprising: a display panel comprising a through hole and a pixel area, the pixel area surrounding the through hole and including pixels to display an image; a force sensor at a first surface of the display panel and configured to sense force applied from an outside; and a light sensor overlapping the through hole of the display panel in a thickness direction of the display panel, the light sensor may sense light incident on the light sensor through the through hole.

According to some example embodiments of the present disclosure, there is provided a display device comprising: a display panel comprising a pixel area and a transmissive area adjacent to the pixel area, the pixel area comprising pixels to display an image; a force sensor at a surface of the display panel and may sense force applied from an outside; and a light sensor overlapping the transmissive area of the display panel in a thickness direction of the display panel and configured to sense light incident on the light sensor through the transmissive area.

According to the aforementioned and other example embodiments of the present disclosure, light emitted from a light emitting device or a display panel may be absorbed or reflected by blood vessels of a user's finger through a first optical hole of a force sensor and a through hole which is a physical hole of the display panel. The light reflected by the blood vessels of the user's finger may be sensed by a light sensor through the through hole of the display panel and the first optical hole of the force sensor. Therefore, the user's blood pressure can be calculated based on the amount of light sensed by the light sensor and the force sensed by the force sensor.

Further, light emitted from a light emitting device or a display panel may be absorbed or reflected by blood vessels of a user's finger through a first optical hole of a force sensor and a transmissive area which is an optical hole of the display panel. The light reflected by the blood vessels of the user's finger may be sensed by a light sensor through the transmissive area of the display panel and the first optical hole of the force sensor. Therefore, the user's blood pressure can be calculated based on the amount of light sensed by the light sensor and the force sensed by the force sensor.

Other aspects and example embodiments may be apparent from the following detailed description, the drawings, and the claims and equivalents thereof.

BRIEF DESCRIPTION OF THE DRAWINGS

The above and other example embodiments and features of the present disclosure will become more apparent by describing example embodiments thereof with reference to the attached drawings, in which.

DETAILED DESCRIPTION

Figure 1:
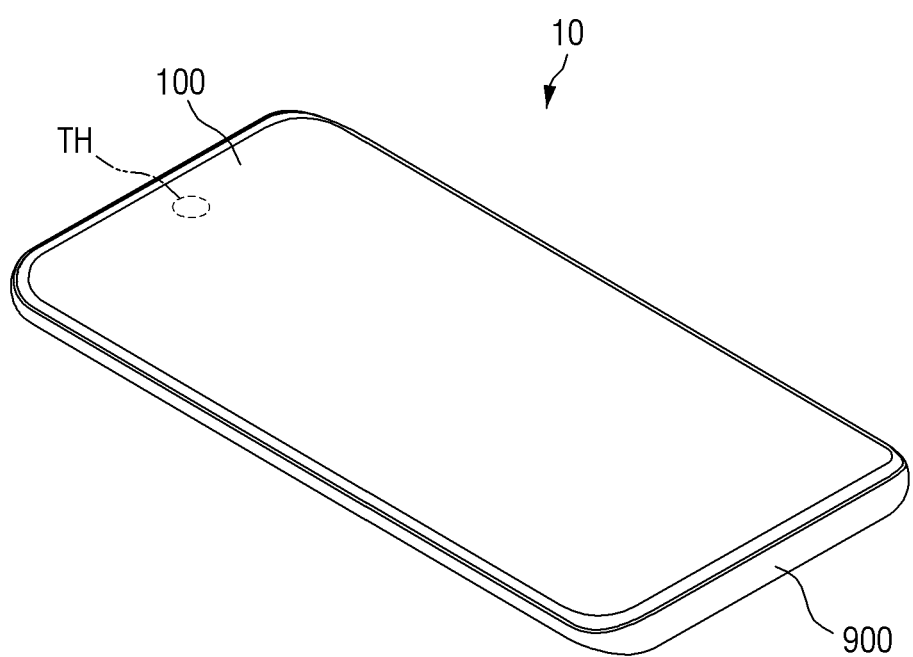
FIG. 1 is a schematic perspective view of a display device according to an embodiment.

The present disclosure will now be described more fully hereinafter with reference to the accompanying drawings, in which some embodiments of the disclosure are shown. This disclosure may, however, be embodied in different forms and should not be construed as being limited to the embodiments set forth herein. Rather, these embodiments are provided so that this disclosure will be thorough and complete, and will fully convey the scope of the disclosure to those skilled in the art. The same reference numbers indicate the same components throughout the specification. In the attached figures, the thickness of layers and regions may be exaggerated for clarity.

Herein, the use of the term "may," when describing embodiments of the present disclosure, refers to "one or more embodiments of the present disclosure." As used herein, the term "and/or" includes any and all combinations of one or more of the associated listed items. As used herein, the singular forms "a", "an" and "the" are intended to include the plural forms as well, unless the context clearly indicates otherwise. As used herein, expressions such as "at least one of", "one of", and "selected from", when preceding a list of elements, modify the entire list of elements and do not modify the individual elements of the list.

It will be understood that when an element or layer is referred to as being "on", "connected to", "coupled to", or "adjacent to" another element or layer, it can be directly on, connected to, coupled to, or adjacent to the other element or layer, or one or more intervening elements or layers may be present. In contrast, when an element or layer is referred to as being "directly on," "directly connected to", "directly coupled to", or "immediately adjacent to" another element or layer, there are no intervening elements or layers present. As used herein, the term "substantially," "about," and similar terms are used as terms of approximation and not as terms of degree, and are intended to account for the inherent deviations in measured or calculated values that would be recognized by those of ordinary skill in the art.

As used herein, the phrases such as "a plan view" may refer to a view from top or from a direction normal to the display area of the display device.

Spatially relative terms, such as "beneath," "below," "lower," "above," "upper," "bottom," "top" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" or "over" the other elements or features. Thus, the term "below" may encompass both an orientation of above and below. The device may be otherwise oriented (rotated 90 degrees or at other orientations), and the spatially relative descriptors used herein should be interpreted accordingly.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present disclosure, and should not be interpreted in an idealized or overly formal sense, unless expressly so defined herein.

Hereinafter, embodiments of the present disclosure will be described with reference to the attached drawings.

Figure 2:
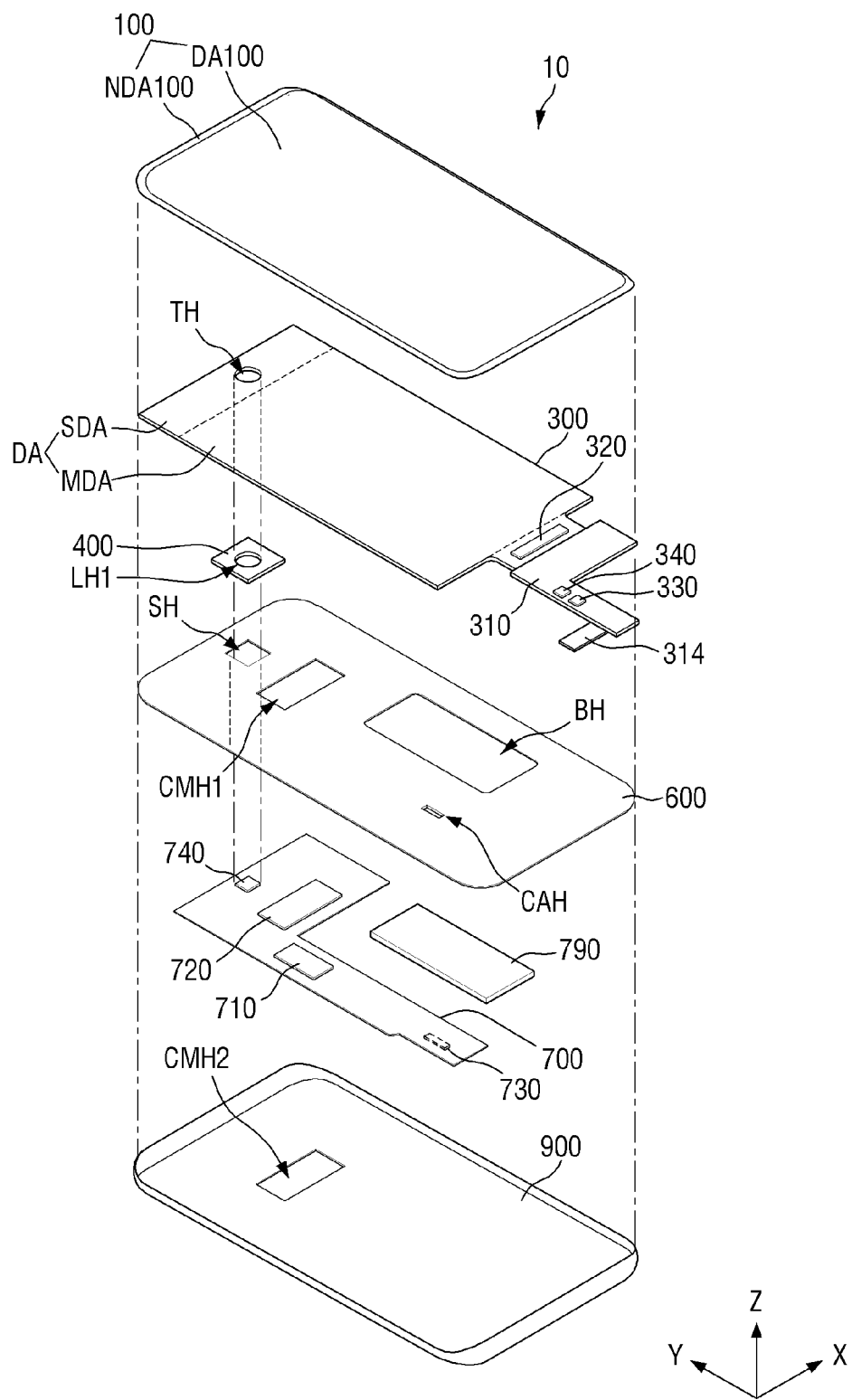
FIG. 2 is an exploded perspective view of the display device according to the embodiment.

FIG. 1 is a perspective view of a display device 10 according to an embodiment. FIG. 2 is an exploded perspective view of the display device 10 according to the embodiment.

Referring to FIGS. 1 and 2, the display device 10 according to the embodiment may be applied to portable electronic devices such as mobile phones, smartphones, tablet personal computers (PCs), mobile communication terminals, electronic notebooks, electronic books, portable multimedia players (PMPs), navigation devices, and ultra-mobile PCs (UMPCs). Alternatively, the display device 10 according to the embodiment may be applied as a display unit of a television, a notebook computer, a monitor, a billboard, or the Internet of things (IoT). Alternatively, the display device 10 according to the embodiment may be applied to wearable devices such as smart watches, watch phones, glass-like displays, and head-mounted displays (HMDs). Alternatively, the display device 10 according to the embodiment may be applied to a dashboard of a vehicle, a center fascia of a vehicle, a center information display (CID) disposed on a dashboard of a vehicle, a room mirror display in place of a side mirror of a vehicle, or a display disposed on the back of a front seat as an entertainment device for a rear seat of a vehicle.

In the present disclosure, a first direction (X-axis direction) may be a short side direction of the display device 10, for example, a horizontal direction of the display device 10, and a second direction (Y-axis direction) may be a long side direction of the display device 10, for example, a vertical direction of the display device 10. In other words, the display device may have a first side extending in the first direction that is shorter in length than a second side extending in the second direction. A third direction (Z-axis direction) may be a thickness direction of the display device 10.

The display device 10 may have a planar shape similar to a quadrangle. For example, the display device 10 may have a planar shape similar to a quadrangle having short sides in the first direction (X-axis direction) and long sides in the second direction (Y-axis direction) as illustrated in FIG. 1. Each corner where a short side extending in the first direction (X-axis direction) meets a long side extending in the second direction (Y-axis direction) may be rounded with a set (e.g., predetermined) curvature or may be right-angled (e.g., right-angle formed between the short side and the long side). The planar shape of the display device 10 is not limited to the quadrangular shape. For example, the planar shape of the display device 10 may be another polygonal shape, a circular shape, or an oval shape.

The display device 10 may be formed flat or substantially flat. Alternatively, the display device 10 may be formed such that two sides (e.g., facing or opposing sides) are bent. For example, the display device 10 may be formed such that left and right sides are bent. Alternatively, the display device 10 may be formed such that each of the upper, lower, left and right sides are bent.

The display device 10 according to the embodiment includes a cover window 100, a display panel 300, a display circuit board 310, a display driving circuit 320, a bracket 600, a main circuit board 700, a light sensor 740, and a bottom cover 900.

The cover window 100 may be disposed on the display panel 300 to cover a front surface of the display panel 300. Thus, the cover window 100 may protect the front surface of the display panel 300.

The cover window 100 may include a light transmitting part DA100 corresponding to the display panel 300 and a light blocking part NDA100 corresponding to an area other than the display panel 300. The light blocking part NDA100 may be adjacent to the light transmitting part DA100. In the embodiment, the light blocking part NDA100 may surround the light transmitting part DA100. The light blocking part NDA100 may be formed to be opaque. Alternatively, the light blocking part NDA100 may be formed as a decorative layer having a pattern that may be shown (or visible) to a user when an image is not displayed.

The display panel 300 may be disposed under the cover window 100. The display panel 300 may include a display area DA and a non-display area NDA. In an embodiment, the non-display area NDA of the panel 300 may correspond to the light blocking part NDA100 of the cover window 100. The display area DA may be an area which includes pixels displaying an image, and the non-display area NDA may be an area which does not display an image and is disposed around the display area DA. The non-display area NDA may not include pixels. The non-display area NDA may surround the display area DA as illustrated in FIG. 2, but the present disclosure is not limited thereto. The display area DA may occupy most of the area (e.g., planar area) of the display panel 300.

The display panel 300 may include a through hole TH. The through hole TH may be a hole penetrating the display panel 300. In other words, the through hole TH may extend through the display panel 300. The through hole TH may be surrounded by the display area DA (e.g., a sub-display area SDA of the display area DA).

The through hole TH may overlap a sensor hole SH of the bracket 600 and the light sensor 740 in the third direction (Z-axis direction). Thus, light passing through the through hole TH of the display panel 300 may be incident on the light sensor 740 through the sensor hole SH. Therefore, even though the light sensor 740 is disposed under the display panel 300, the light sensor 740 can sense light that is incident on the light sensor 740 from a front surface (e.g., a front surface of the cover window 100) of the display device 10.

Although the display panel 300 includes only one through hole TH in FIG. 2, the number of through holes TH is not limited thereto. For example, when the display panel 300 includes a plurality of through holes TH, any one of the through holes TH may overlap the light sensor 740 in the third direction (Z-axis direction), and the other one of the through holes TH may overlap a sensor device other than the light sensor 740. For example, the sensor device overlapping a through hole TH may be a proximity sensor, an illuminance sensor, or a front camera sensor.

The display panel 300 may be a light emitting display panel including light emitting elements. For example, the display panel 300 may be an organic light emitting display panel using organic light emitting diodes that include organic light emitting layers, a micro light emitting diode display panel using micro light emitting diodes, a quantum dot light emitting display panel using quantum dot light emitting diodes that include quantum dot light emitting layers, or an inorganic light emitting display panel using inorganic light emitting elements that include inorganic semiconductors. A case where the display panel 300 is an organic light emitting display panel may be mainly described below.

In addition, the display panel 300 may include a touch electrode layer having touch electrodes for sensing an object such as a human finger or a pen. In this case, the touch electrode layer may be disposed on a display layer in which pixels displaying an image are disposed. The display layer and the touch electrode layer will be described in more detail later with reference to FIG. 8.

The display circuit board 310 and the display driving circuit 320 may be attached to a side of the display panel 300. The display circuit board 310 may be a flexible printed circuit board that can be bent, a rigid printed circuit board that may be hard or rigid and may not be easily bent, or a composite printed circuit board including both a rigid printed circuit board and a flexible printed circuit board.

The display driving circuit 320 may receive control signals and power voltages through the display circuit board 310 and generate and output signals and voltages for driving the display panel 300. The display driving circuit 320 may be formed as an integrated circuit and attached onto the display panel 300 using a chip-on-glass (COG) method, a chip-on-plastic (COP) method, or an ultrasonic bonding method. However, the present disclosure is not limited thereto. For example, the display driving circuit 320 may be attached onto the display circuit board 310 and/or the display panel 300.

A touch driving circuit 330 and a force driving circuit 340 may be disposed on the display circuit board 310. Each of the touch driving circuit 330 and the force driving circuit 340 may be formed as an integrated circuit and attached onto an upper surface of the display circuit board 310. Alternatively, the touch driving circuit 330 and the force driving circuit 340 may be integrated into one integrated circuit (e.g., one monolithic structure) in some cases.

The touch driving circuit 330 may be connected (e.g., electrically connected) to the touch electrodes of the touch electrode layer of the display panel 300 through the display circuit board 310. The touch driving circuit 330 may output a touch driving signal to the touch electrodes and sense a voltage charged in a capacitor formed by each touch electrode to measure a chance in capacitance.

The touch driving circuit 330 may generate touch data according to a change in an electrical signal sensed at each of the touch electrodes and transmit the touch data to a main processor 710, and the main processor 710 may analyze the touch data to calculate touch coordinates at which a touch has occurred. A touch may include a contact touch and a proximity touch. The contact touch refers to a case where an object such as a human finger or a pen directly contacts the cover window 100 disposed on the touch electrode layer. The proximity touch refers to a case where an object such as a human finger or a pen is positioned (e.g., hovers) above the cover window 100 in proximity to the cover window 100.

The force driving circuit 340 may sense an electrical signal from a force sensor electrode of a force sensor 400, convert the sensed signal into force data, and transmit the force data to the main processor 710. Based on the force data, the main processor 710 may determine whether force has been applied to the force sensor 400 and calculate the magnitude of the force applied to the force sensor 400.

In addition, a power supply unit for supplying display driving voltages for driving the display driving circuit 320 may be additionally disposed on the display circuit board 310.

The bracket 600 may be disposed under the display panel 300. The bracket 600 may include plastic, metal, or both plastic and metal. The bracket 600 may include a first camera hole CMH1 into which a first camera sensor 720 is inserted, a battery hole BH in which a battery 790 is disposed, a cable hole CAH through which a cable 314 connected to the display circuit board 310 passes, and the sensor hole SH which overlaps the light sensor 740 in the third direction (Z-axis direction). In this case, the light sensor 740 may be disposed in the sensor hole SH. Alternatively, the bracket 600 may be formed not to overlap a sub-display area SDA of the display panel 300 instead of including the sensor hole SH.

The main circuit board 700 and the battery 790 may be disposed under the bracket 600. The main circuit board 700 may be a printed circuit board or a flexible printed circuit board.

The main circuit board 700 may include the main processor 710, the first camera sensor 720, a main connector 730, and the light sensor 740. The first camera sensor 720 may be disposed on both an upper surface and a lower surface of the main circuit board 700, the main processor 710 may be disposed on the upper surface of the main circuit board 700, and the main connector 730 may be disposed on the lower surface of the main circuit board 700. The light sensor 740 may be disposed on the upper surface of the main circuit board 700.

The main processor 710 may control functions (e.g., all of the functions) of the display device 10. For example, the main processor 710 may output digital video data to the display driving circuit 320 through the display circuit board 310 so that the display panel 300 can display an image. In addition, the main processor 710 may receive touch data from the touch driving circuit 330, determine touch coordinates of a user, and then execute an application indicated by an icon displayed at the touch coordinates of the user. In addition, the main processor 710 may convert first image data received from the first camera sensor 720 into digital video data and output the digital video data to the display driving circuit 320 through the display circuit board 310. Thus, an image captured by the first camera sensor 720 can be displayed on the display panel 300. In addition, the main processor 710 may determine a user's blood pressure according to a sensor signal received from the light sensor 740.

The first camera sensor 720 processes an image frame such as a still image or a moving image obtained by an image sensor and outputs the processed image frame to the main processor 710. The first camera sensor 720 may be a complementary metal-oxide-semiconductor (CMOS) image sensor or a charge-coupled device (CCD) sensor. The first camera sensor 720 may be exposed on a lower surface of the bottom cover 900 by a second camera hole CMH2. Thus, the first camera sensor 720 can photograph an object or background disposed under the display device 10.

The cable 314 passing through the cable hole CAH of the bracket 600 may be connected to the main connector 730. Therefore, the main circuit board 700 may be connected (e.g., electrically connected) to the display circuit board 310.

The light sensor 740 may include a light receiving element capable of sensing light through the through hole TH that is incident on the light receiving element. In this case, the light receiving element may be a photodiode or a phototransistor. For example, the light sensor 740 may be a CMOS image sensor or a CCD sensor capable of sensing light. The light sensor 740 may output an optical signal to the main processor 710 according to the amount of light reflected by an object disposed on the through hole TH. Based on the optical signal, the main processor 710 may generate a pulse wave signal that reflects blood changes according to a heartbeat. The main processor 710 may measure a user's blood pressure according to the pulse wave signal. A method of measuring a person's blood pressure using the light sensor 740 will be described later in more detail with reference to FIGS. 4 and 5.

The battery 790 may be disposed not to overlap the main circuit board 700 in the third direction (Z-axis direction). The battery 790 may overlap the battery hole BH of the bracket 600. For example, the battery 790 may be disposed at or in the battery hole BH of the bracket 600.

In addition, the main circuit board 700 may further include a mobile communication module capable of transmitting and receiving wireless signals to and from at least one of a base station, an external terminal, or a server over a mobile communication network. The wireless signals may include voice signals, video call signals, or various types of data according to transmission/reception of text/multimedia messages.

The bottom cover 900 may be disposed under the main circuit board 700 and the battery 790. The bottom cover 900 may be fastened and fixed to the bracket 600. The bottom cover 900 may form the bottom exterior of the display device 10. The bottom cover 900 may include plastic, metal, or both plastic and metal.

The second camera hole CMH2 exposing a lower surface of the first camera sensor 720 may be formed in the bottom cover 900. The position of the first camera sensor 720 and the positions of the first and second camera holes CMH1 and CMH2 corresponding to the first camera sensor 720 are not limited to the embodiment illustrated in FIG. 2. In other words, the position of the first camera sensor 720 and the positions of the first and second camera holes CMH1 and CMH2 corresponding to the first camera sensor 720 may be at any suitable location of the display device 10.

Figure 3:
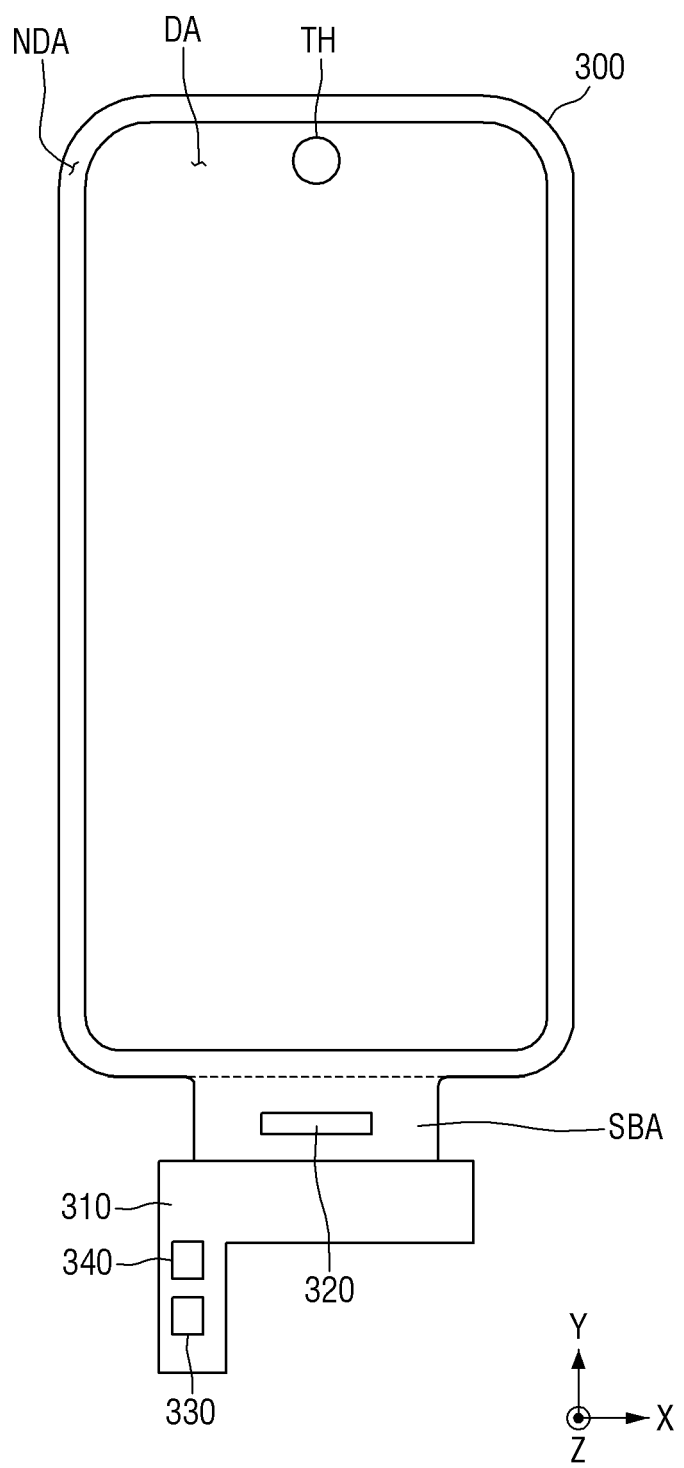
FIG. 3 is a plan view illustrating a display panel, a display circuit board, a display driving circuit, and a touch driving circuit according to an embodiment.

FIG. 3 is a plan view illustrating the display panel 300, the display circuit board 310, the display driving circuit 320, and the touch driving circuit 330 according to an embodiment.

Referring to FIG. 3, the display panel 300 may be a rigid display panel that is hard or rigid and not easily bent or a flexible display panel that is flexible and can be easily bent, folded or rolled. For example, the display panel 300 may be a foldable display panel that can be folded and unfolded, a curved display panel whose display surface is curved, a bended display panel whose areas other than a display surface are bent, a rollable display panel that can be rolled or unrolled, or a stretchable display panel that can be stretched.

In addition, the display panel 300 may be a transparent display panel that is implemented to be transparent so that an object or background disposed on a lower surface of the display panel 300 can be seen from (or through) the front surface of the display panel 300. In other words, an object or background facing a lower surface (e.g., a rear surface) of the display panel 300 may be visible from (or through) the front surface of the display panel 300. Alternatively, the display panel 300 may be a reflective display panel that can show a reflection of an object or background on the front surface of the display panel 300.

The display panel 300 may include a main area MA and a sub area SBA protruding from a side of the main area MA. The main area MA may include the display area DA which displays an image and the non-display area NDA which is disposed around the display area DA. The display area DA may occupy most of the main area MA. The display area DA may be disposed at the center of the main area MA. The non-display area NDA may be an area outside the display area DA. The non-display area NDA may be defined as an edge area of the display panel 300.

The display panel 300 may include the through hole TH. The through hole TH may be a hole penetrating the display panel 300. Although the through hole TH is a hole penetrating the display panel 300 (i.e., a physically formed hole through the display panel 300 in FIG. 3), the present disclosure is not limited thereto. The through hole TH may also be an optical hole through which light can pass. Alternatively, the through hole TH may be a combination of a physical hole and an optical hole.

Because the through hole TH overlaps the light sensor 740 in the third direction (Z-axis direction) as illustrated in FIG. 2, light passing through the through hole TH may be incident on the light sensor 740. Therefore, even though the light sensor 740 is overlapped by the display panel 300 in the third direction (Z-axis direction), the light sensor 740 can sense light that is incident on the light sensor 740 from the front surface of the display device 10. For example, the light sensor 740 may sense light reflected by an object disposed on the through hole TH.

The through hole TH may be surrounded by the display area DA. Alternatively, the through hole TH may be surrounded by the non-display area NDA or may be disposed between the display area DA and the non-display area NDA (i.e., the through hole TH may be arranged across a boundary between the display area DA and the non-display area NDA). In addition, although the through hole TH is disposed at an upper center of the display panel 300, the position of the through hole TH is not limited thereto. For example, the through hole TH may be disposed at any suitable location of the display panel 300.

The sub area SBA may protrude in the second direction (Y-axis direction) from a side of the main area MA. As illustrated in FIG. 2, a length of the sub area SBA in the first direction (X-axis direction) may be smaller (or less) than a length of the main area MA in the first direction (X-axis direction), and a length of the sub area SBA in the second direction (Y-axis direction) may be smaller (or less) than a length of the main area MA in the second direction (Y-axis direction), but the present disclosure is not limited thereto. The sub area SBA may be bent and disposed under the display panel 300. In this case, the sub area SBA may be overlapped by the main area MA in the third direction (Z-axis direction).

The sub area SBA of the display panel 300 may be bent and disposed under the display panel 300 as illustrated in FIG. 2. In this case, the sub area SBA of the display panel 300 may be overlapped by the main area MA of the display panel 300 in the third direction (Z-axis direction).

The display circuit board 310 and the display driving circuit 320 may be attached to the sub area SBA of the display panel 300. The display circuit board 310 may be attached onto pads of the sub area SBA of the display panel 300 by using a low-resistance, high-reliability material such as an anisotropic conductive film and/or a self-assembly anisotropic conductive paste (SAP). The touch driving circuit 330 may be disposed on the display circuit board 310.

Figure 4:
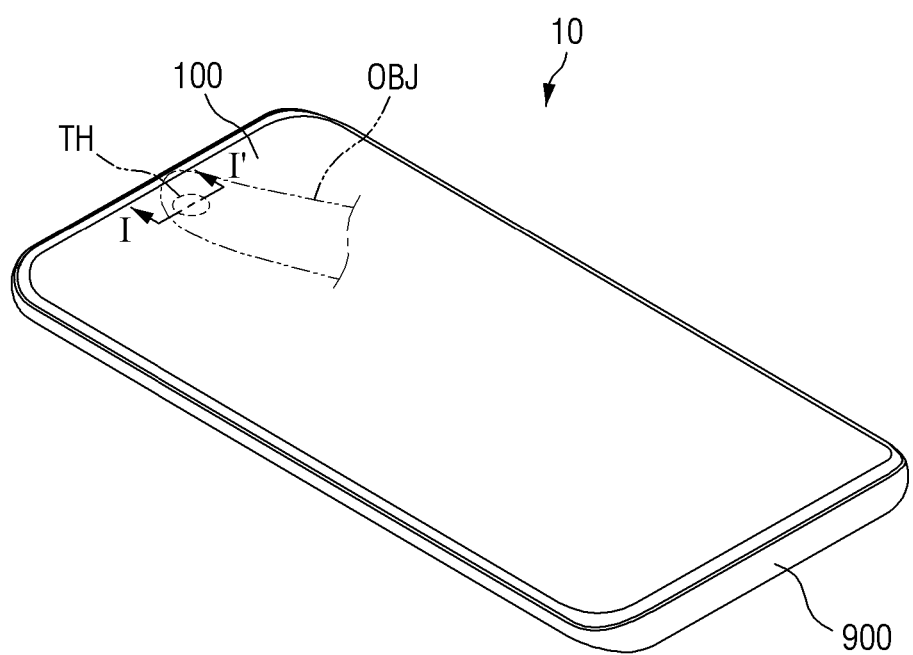
FIG. 4 is a schematic perspective view illustrating a case where blood pressure is measured by the display device according to the embodiment.
Figure 5:
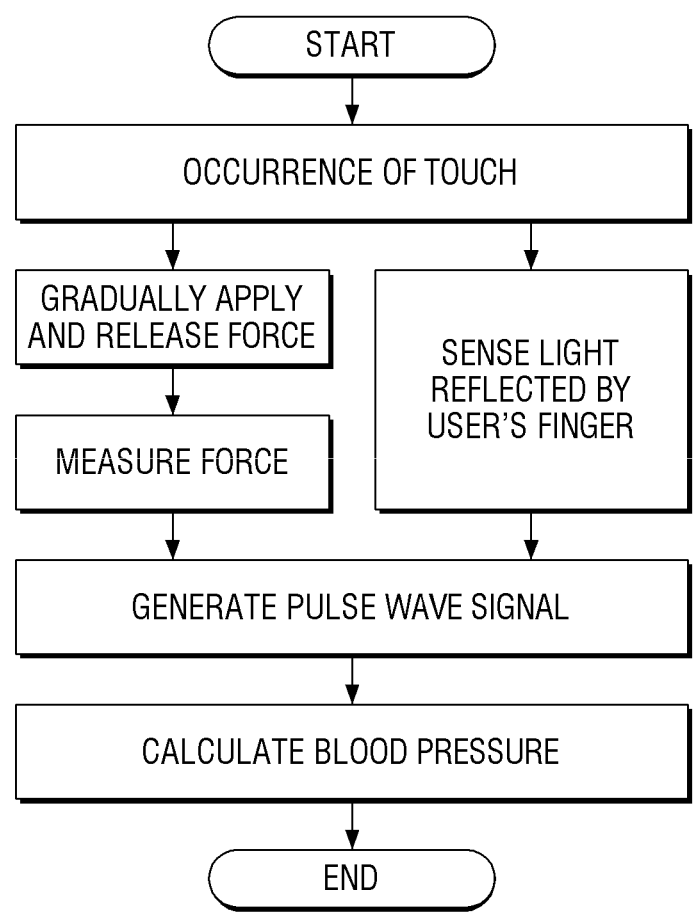
FIG. 5 is a flowchart illustrating a blood pressure measurement method of the display device according to the embodiment.

FIG. 4 is a schematic perspective view illustrating a case where blood pressure is measured by the display device 10 according to the embodiment. FIG. 5 is a flowchart illustrating a blood pressure measurement method of the display device 10 according to the embodiment.

Referring to FIGS. 4 and 5, when a part of a user's body (e.g., a finger OBJ touches the front surface of the display device 10), the display device 10 may recognize that a touch has occurred. The display device 10 may recognize the user's touch by using the touch electrode layer of the display panel 300 or the force sensor 400.

When determining that a touch has occurred, the display device 10 may operate in a blood pressure measurement mode. For example, when a user sets the blood pressure measurement mode through a program or an application of the display device 10 before measuring blood pressure, the display device 10 may perform blood pressure measurement according to the occurrence of a touch (e.g., the touch may trigger the blood pressure measurement mode). Alternatively, the display device 10 may automatically switch to the blood pressure measurement mode after a touch occurs without the user's mode determination operation (e.g., without the user selecting a program or an application of the display device 10). The display device 10 may operate in a touch mode when the user's touch position is irrelevant to a blood pressure measurement position (i.e., the touch position does not correspond to the blood pressure measurement position) and may operate in the blood pressure measurement mode when the user's touch position corresponds to the blood pressure measurement position. In addition, when the user increases touch force, the display device 10 may operate in the blood pressure measurement mode through force analysis of the force sensor 400.

The display device 10 may measure blood pressure using both the light sensor 740 and the force sensor 400 in the blood pressure measurement mode.

Figure 6:
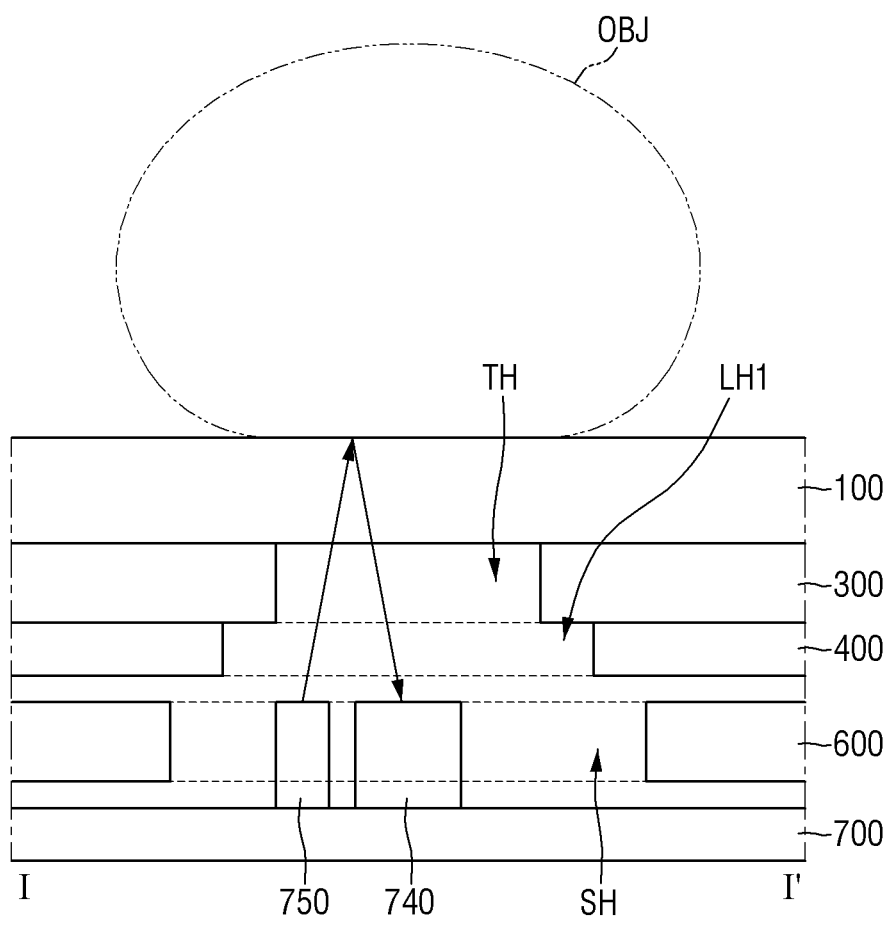
FIG. 6 is a cross-sectional view illustrating a cover window, the display panel, a force sensor, a light emitting device, and a light sensor according to an embodiment.

As illustrated in FIG. 6, light reflected by a user's finger OBJ among light output from a light emitting device 750 may be sensed by the light sensor 740 through the through hole TH. Blood ejected from the left ventricle of the heart during systole of the heart is moved to peripheral tissues, thereby increasing the blood volume of the arteries. In addition, red blood cells carry more oxygen hemoglobin to the peripheral tissues during the systole of the heart. During diastole of the heart, blood is partially drawn from the peripheral tissues toward the heart. When light is irradiated to peripheral blood vessels, the irradiated light is absorbed by the peripheral tissues. Light absorbance is dependent on hematocrit and blood volume. The light absorbance may have a maximum value during the systole of the heart and a minimum value during the diastole of the heart. Therefore, the amount of light sensed by the light sensor 740 may be the smallest or lowest during the systole of the heart and may be the largest or greatest during the diastole of the heart.

In addition, when a user places a finger on the display device 10 and then lifts the finger off the display device 10 in the blood pressure measurement mode, force (e.g., contact force) applied to the force sensor 400 may gradually increase to reach a maximum value and then may gradually decrease. When the contact force increases, blood vessels may shrink, causing blood flow to decrease or to become zero. When the contact force decreases, the blood vessels may expand, causing blood to flow again. A further decrease in contact force results in a greater blood flow. Therefore, a change in the amount of light sensed by the light sensor 740 may be proportional to a change in blood flow.

The main processor 710 may generate a pulse wave signal according to force applied by a user based on a force value calculated by the force sensor 400 and an optical signal according to the amount of light sensed by the light sensor 740 and may calculate blood pressure based on the pulse wave signal. The pulse wave signal may have a waveform that vibrates according to a heartbeat cycle. For example, the main processor 710 may estimate blood pressure levels of blood vessels of the user's finger OBJ based on differences between times corresponding to peaks of the generated pulse wave signal and times corresponding to peaks of filtered pulse waves. Of the estimated blood pressure levels, a maximum blood pressure level may be calculated as systolic blood pressure, and a minimum blood pressure level may be calculated as diastolic blood pressure. In addition, other blood pressure levels such as an average blood pressure level may be calculated using the estimated blood pressure levels. The calculated blood pressure may be displayed to the user through the display area DA of the display device 10.

The above blood pressure measurement method is merely an example, and various other methods are disclosed in Korean Patent Publication Nos. 10-2018-0076050, 10-2017-0049280 and 10-2019-0040527, the entire disclosures of which may be incorporated herein by reference.

Although a user's finger OBJ is illustrated in FIGS. 4 and 5 as a part of the user's body where blood pressure is measured, the present disclosure is not limited thereto. For example, blood pressure may be measured at any suitable position of the user's body such as a wrist or other part of the body.

FIG. 6 is a cross-sectional view illustrating the cover window 100, the display panel 300, the force sensor 400, the light emitting device 750, and the light sensor 740 according to an embodiment.

In FIG. 6, an example of a cross-section of the display device 10 taken along I-I' of FIG. 4 is illustrated. In FIG. 6, the bottom cover 900 is omitted for ease of description.

Referring to FIG. 6, the display device 10 may further include the force sensor 400, and the light emitting device 750.

The force sensor 400 may be disposed on a surface of the display panel 300. For example, the force sensor 400 may be disposed on the lower surface of the display panel 300. In this case, an upper surface of the force sensor 400 may be attached to the lower surface of the display panel 300 by a transparent adhesive member. However, the present disclosure is not limited thereto, and any suitable attachment mechanism and material may be used.

The force sensor 400 may be overlapped by the display area DA of the display panel 300 in the third direction (Z-axis direction). For example, the force sensor 400 may be completely overlapped by the display area DA of the display panel 300 in the third direction (Z-axis direction). In other words, the entire force sensor 400 may be overlapped by the display area DA of the display panel 300 in the third direction (Z-axis direction). Alternatively, a part of the force sensor 400 may be overlapped by the display area DA of the display panel 300 in the third direction (Z-axis direction), and the other part (e.g., a separate part of the force sensor 400) may be overlapped by the non-display area NDA of the display panel 300 in the third direction (Z-axis direction).

The force sensor 400 may include a first optical hole LH1. The first optical hole LH1 may be an optical hole through which light can pass. Alternatively, the first optical hole LH1 may be a physically formed hole like a hole penetrating the force sensor 400. In other words, the first optical hole H1 may extend through the force sensor 400. Alternatively, the first optical hole LH1 may be a combination of a physical hole and an optical hole.

The through hole TH of the display panel 300 may completely overlap the first optical hole LH1 of the force sensor 400. The through hole TH of the display panel 300 may be smaller in size than the first optical hole LH1 of the force sensor 400. A length of the through hole TH in a direction may be smaller (or less) than a length of the first optical hole LH1 in the direction. For example, as illustrated in FIG. 6, a length of the through hole TH in the first direction (X-axis direction) may be smaller (or less) than a length of the first optical hole LH1 in the first direction (X-axis direction). Therefore, light passing through the through hole TH may be incident on the light sensor 740, which is overlapped by the through hole TH in the third direction (Z-axis direction), without being blocked by the force sensor 400.

The polarizing film may be disposed between the display panel 300 and the cover window 100. The polarizing film may include a first base member, a linear polarizing plate, a quarter-wave (λ/4) plate, a half-wave (λ/2) plate, and a second base member. In this case, the first base member, the λ/4 plate, the λ/2 plate, the linear polarizing plate, and the second base member may be stacked (e.g., sequentially stacked) on the display panel 300.

The bracket 600 may be disposed on a surface of the force sensor 400. For example, the bracket 600 may be disposed on a lower surface of the force sensor 400. The bracket 600 may include the sensor hole SH which is a physical hole penetrating the bracket 600. In other words, the sensor hole SH may extend through the bracket 600. Alternatively, the sensor hole SH may be an optical hole through which light can pass. Alternatively, the sensor hole SH may be a combination of a physical hole and an optical hole.

The through hole TH of the display panel 300 may completely overlap the sensor hole SH of the bracket 600. In other words, the entire through hole TH of the display panel 300 may overlap the sensor hole SH of the bracket 600. The through hole TH of the display panel 300 may be smaller in size than the sensor hole SH of the bracket 600. A length of the through hole TH in a direction may be smaller (or less) than a length of the sensor hole SH in the direction. For example, as illustrated in FIG. 6, the length of the through hole TH in the first direction (X-axis direction) may be smaller (or less) than a length of the sensor hole SH in the first direction (X-axis direction).

In addition, the first optical hole LH1 of the force sensor 400 may completely overlap the sensor hole SH of the bracket 600. In other words the entire first optical hole LH1 of the force sensor 400 may overlap the sensor hole SH of the bracket 600. The first optical hole LH1 of the force sensor 400 may be smaller in size than the sensor hole SH of the bracket 600. A length of the first optical hole LH1 in a direction may be smaller (or less) than a length of the sensor hole SH in the direction. For example, as illustrated in FIG. 6, the length of the first optical hole LH1 in the first direction (X-axis direction) may be smaller (or less) than the length of the sensor hole SH in the first direction (X-axis direction). Therefore, light passing through the through hole TH and the first optical hole LH1 may be incident on the light sensor 740, which is overlapped by the through hole TH in the third direction (Z-axis direction), without being blocked by the bracket 600.

The light emitting device 750 may include a light source that emits light. The light source may include, for example, at least one of a light emitting diode, an organic light emitting diode, a laser diode, quantum dots, or a phosphor.

The wavelength of light emitted by the light emitting device 750 may be an infrared wavelength, a blue wavelength of visible light, a red wavelength of visible light, or a green wavelength of visible light. Here, when a body part disposed on the through hole TH is a finger OBJ, because blood vessels of the finger OBJ are tiny, if the wavelength of light emitted by the light emitting device 750 is the infrared wavelength or the red wavelength of visible light, the light can easily penetrate into and be absorbed by the blood vessels (e.g., the tiny blood vessels) of the finger OBJ because the infrared wavelength and the red wavelength of visible light are longer than the green wavelength of visible light or the blue wavelength of visible light. In addition, when the body part disposed on the through hole TH is a wrist, because arteries of the wrist are sufficiently thick, even if the wavelength of light emitted by the light emitting device 750 is the green wavelength of visible light, the light can penetrate into and be absorbed by the arteries of the wrist. Accordingly, the wavelength of light emitted by the light emitting device 750 may be determined according to a part of the body to measure blood pressure.

The light sensor 740 and the light emitting device 750 may be disposed on a surface of the main circuit board 700. For example, the light sensor 740 and the light emitting device 750 may be mounted on an upper surface of the main circuit board 700.

The light sensor 740 and the light emitting device 750 may be overlapped by the through hole TH in the third direction (Z-axis direction). The light sensor 740 and the light emitting device 750 may be disposed in the sensor hole SH of the bracket 600. Alternatively, when the light sensor 740 and the light emitting device 750 are long in the third direction (Z-axis direction) (i.e., greater in length in the third direction than the sensor hole SH), they may be disposed in the first optical hole LH1 of the force sensor 400 or in both the through hole TH of the display panel 300 and the first optical hole LH1 of the force sensor 400. In this case, the through hole TH of the display panel 300 and the first optical hole LH1 of the force sensor 400 may all be physical holes. Accordingly, the light sensor 740 and/or the light emitting device 750 may be inserted into the sensor hole SH, the first optical hole LH1, and/or the through hole TH depending on a length of the light sensor 740 and/or the light emitting device 750 in the third direction (Z-axis direction).

As illustrated in FIG. 6, light emitted from the light emitting device 750 may be absorbed or reflected by the blood vessels of a user's finger OBJ through the first optical hole LH1 of the force sensor 400 and the through hole TH of the display panel 300. The light reflected by the blood vessels of the user's finger OBJ may be sensed by the light sensor 740 through the through hole TH of the display panel 300 and the first optical hole LH1 of the force sensor 400.

Figure 7:
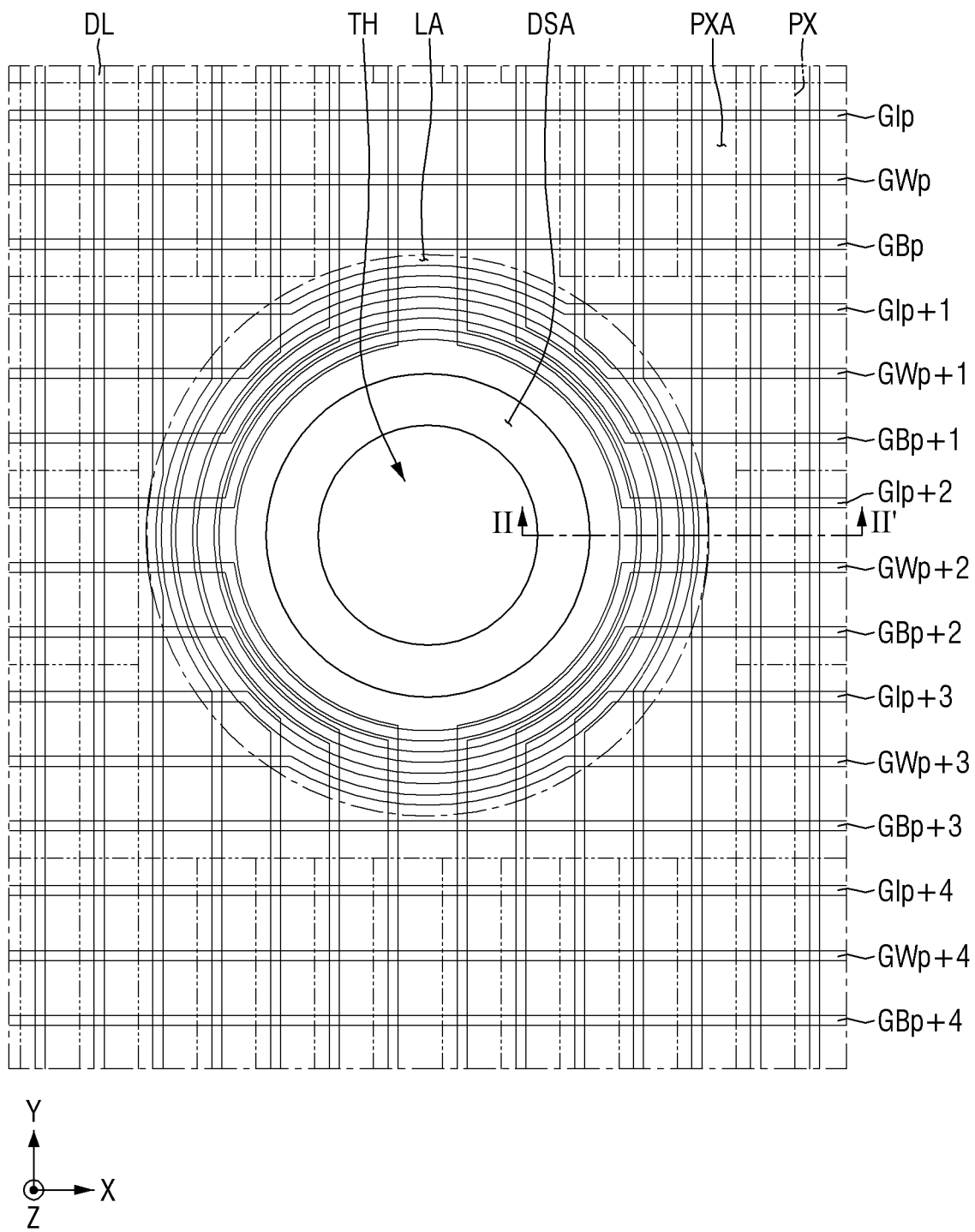
FIG. 7 is a layout view illustrating a display area and a through hole of the display panel according to an embodiment.

FIG. 7 is a layout view illustrating the display area DA and the through hole TH of the display panel 300 according to an embodiment.

Referring to FIG. 7, the display area DA may include the through hole TH, a dead space area DSA, a wiring area LA, and a pixel area PXA.

The dead space area DSA may surround the through hole TH. In the dead space area DSA, pixels PX, scan lines SL, and data wirings DL may not be disposed. The dead space area DSA may be an area for preventing or substantially preventing the through hole TH from invading (or being in) the wiring area LA due to a process error in a process of forming the through hole TH.

The wiring area LA may surround the dead space area DSA. Because the pixels PX are not disposed in the wiring area LA, the wiring area LA corresponds to the non-display area NDA which does not display an image.

In the wiring area LA, scan wirings and the data wirings DL bypassing the through hole TH may be disposed. The scan wirings may include first initialization scan wirings GIp through GIp+4 (GIp, GIp+1, GIp+2, GIp+3, and GIp+4), write scan wirings GWp through GWp+4 (GWp, GWp+1, GWp+2, GWp+3, and GWp+4), and second initialization scan wirings GBp through GBp+4 (GBp, GBp+1, GBp+2, GBp+3, and GBp+4).

The first initialization scan wirings GIp through GIp+4, the write scan wirings GWp through GWp+4, and the second initialization scan wirings GBp through GBp+4 may extend in the first direction (X-axis direction). The first initialization scan wirings GIp through GIp+4, the write scan wirings GWp through GWp+4, and the second initialization scan wirings GBp through GBp+4 may be curved in the second direction (Y-axis direction) to bypass or to not be present in the through hole TH. For example, of the first initialization scan wirings GIp through GIp+4, the write scan wirings GWp through GWp+4, and the second initialization scan wirings GBp through GBp+4, wirings bypassing an upper side of the through hole TH may be curved upward. On the other hand, of the first initialization scan wirings GIp through GIp+4, the write scan wirings GWp through GWp+4, and the second initialization scan wirings GBp through GBp+4, wirings bypassing a lower side of the through hole TH may be curved downward. Alternatively, the first initialization scan wirings GIp through GIp+4, the write scan wirings GWp through GWp+4, and the second initialization scan wirings GBp through GBp+4 may be bent in a staircase shape to bypass or to not be present in the through hole TH.

The data wirings DL may extend in the second direction (Y-axis direction). The data wirings DL may be curved in the first direction (X-axis direction) to bypass or to not be present in the through hole TH. For example, of the data wirings DL, wirings bypassing a left side of the through hole TH may be curved to the left. On the other hand, of the data wirings DL, wirings bypassing a right side of the through hole TH may be curved to the right. Alternatively, the data wirings DL may be bent in a staircase shape to bypass or to not be present in the through hole TH.

To minimize or reduce the size of the wiring area LA, a gap between adjacent scan wirings may be smaller (or less) in the wiring area LA than a gap between adjacent scan wirings in the pixel area PXA. In addition, a gap between adjacent data wirings DL may be smaller (or less) in the wiring area LA than a gap between adjacent data wirings DL in the pixel area PXA. In addition, in the wiring area LA, the scan wirings may overlap the data wirings DL in the third direction (Z-axis direction).

Each of the pixels PX may overlap any one of the first initialization scan wirings GIp through GIp+4, any one of the write scan wirings GWp through GWp+4, any one of the second initialization scan wirings GBp through GBp+4, and any one of the data wirings DL.

As illustrated in FIG. 7, the scan wirings and the data wirings DL are designed to bypass or to not be present in the through hole TH in the wiring area LA, and the pixels PX are not disposed in the wiring area LA. Therefore, even though the through hole TH penetrates (or extends through) the display area DA of the display panel 300, the display panel 300 may stably display an image.

Figure 8:
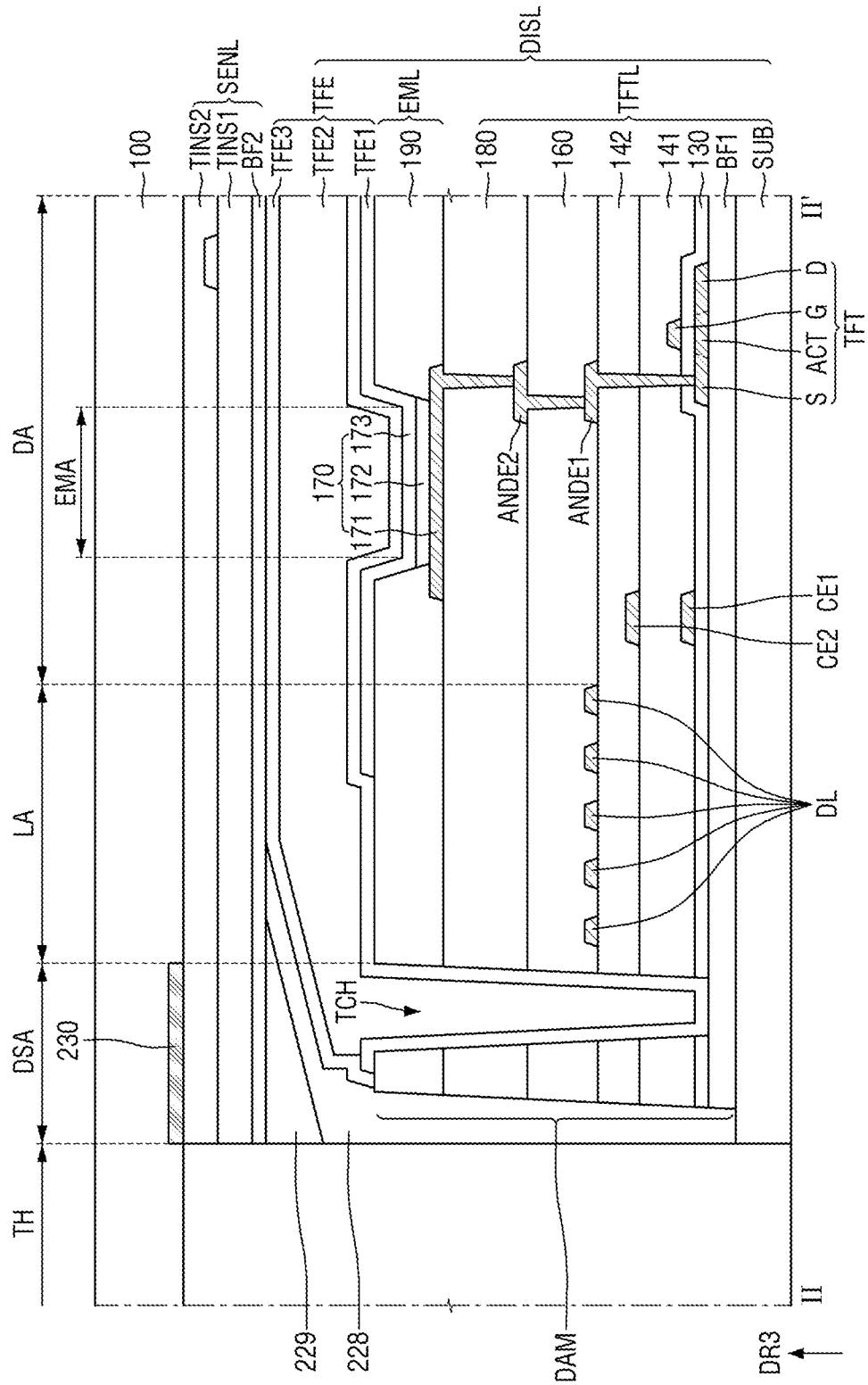
FIG. 8 is a cross-sectional view of an example of the display panel of FIG. 7.

FIG. 8 is a cross-sectional view of an example of the display panel 300 of FIG. 7. In FIG. 8, a cross-section of the display panel 300 taken along II-II' of FIG. 7 is illustrated.

Referring to FIG. 8, a first buffer layer BF1 may be disposed on a substrate SUB, and a thin-film transistor layer TFTL, a light emitting element layer EML, an encapsulation layer TFE and a touch electrode layer SENL may be disposed (e.g., sequentially disposed) on the first buffer layer BF1.

The substrate SUB may be made of an insulating material such as glass, quartz, and/or polymer resin. For example, the substrate SUB may include polyimide. The substrate SUB may be a flexible substrate that can be bent, folded, and rolled.

The first buffer layer BF1 is a layer for protecting thin-film transistors TFT of the thin-film transistor layer TFTL and a light emitting layer 172 of the light emitting element layer EML from moisture introduced through the substrate SUB which is vulnerable to moisture penetration. The first buffer layer BF1 may be composed of a plurality of inorganic layers stacked alternately. For example, the first buffer layer BF1 may be a multilayer in which one or more inorganic layers selected from a silicon nitride layer, a silicon oxynitride layer, a silicon oxide layer, a titanium oxide layer, and an aluminum oxide layer are alternately stacked.

A light blocking layer BML may be disposed on the substrate SUB. The light blocking layer BML may overlap an active layer ACT of each thin-film transistor TFT to prevent or reduce the generation of leakage current due to light incident on the active layer ACT of the thin-film transistor TFT. The light blocking layer BML may be covered by the first buffer layer BF1. The light blocking layer BML may be a single layer or a multilayer made of any one or more of molybdenum (Mo), aluminum (Al), chromium (Cr), gold (Au), titanium (Ti), nickel (Ni), neodymium (Ne), copper (Cu), and alloys of the same.

The thin-film transistor layer TFTL includes the active layer ACT, a first gate layer GTL1, a second gate layer GTL2, a first source metal layer DTL1, a second source metal layer DTL2, a gate insulating layer 130, a first interlayer insulating film 141, a second interlayer insulating film 142, a first planarization layer 160, and a second planarization layer 180.

The active layer ACT, a source electrode S, and a drain electrode D may be formed on the first buffer layer BF1. The active layer ACT may include polycrystalline silicon, monocrystalline silicon, low-temperature polycrystalline silicon, amorphous silicon, or an oxide semiconductor. When the active layer ACT is made of polycrystalline silicon, the ion-doped active layer ACT may have conductivity. Therefore, the source electrode S and the drain electrode D may be formed by doping the active layer ACT with ions.

The gate insulating layer 130 may be formed on the active layer ACT, the source electrode S, and the drain electrode D. The gate insulating layer 130 may be made of an inorganic layer, for example, a silicon nitride layer, a silicon oxynitride layer, a silicon oxide layer, a titanium oxide layer, or an aluminum oxide layer.

A gate electrode G and a first capacitor electrode CE1 may be formed on the gate insulating layer 130. Each of the gate electrode G and the first capacitor electrode CE1 may be a single layer or a multilayer made of any one or more of molybdenum (Mo), aluminum (Al), chromium (Cr), gold (Au), titanium (Ti), nickel (Ni), neodymium (Ne), copper (Cu), and alloys of the same.

The first interlayer insulating film 141 may be formed on the gate electrode G and the first capacitor electrode CE1. The first interlayer insulating film 141 may be made of an inorganic layer, for example, a silicon nitride layer, a silicon oxynitride layer, a silicon oxide layer, a titanium oxide layer, or an aluminum oxide layer. The first interlayer insulating film 141 may include a plurality of inorganic layers.

A second capacitor electrode CE2 may be formed on the first interlayer insulating film 141. The second capacitor electrode CE2 may be a single layer or a multilayer made of any one or more of molybdenum (Mo), aluminum (Al), chromium (Cr), gold (Au), titanium (Ti), nickel (Ni), neodymium (Ne), copper (Cu), and alloys of the same.

The second interlayer insulating film 142 may be formed on the second capacitor electrode CE2. The second interlayer insulating film 142 may be made of an inorganic layer, for example, a silicon nitride layer, a silicon oxynitride layer, a silicon oxide layer, a titanium oxide layer, or an aluminum oxide layer. The second interlayer insulating film 142 may include a plurality of inorganic layers.

A first anode connection electrode ANDE1 may be included on the second interlayer insulating film 142. The first anode connection electrode ANDE1 may be connected to the source electrode S through a contact hole penetrating (or extending through) the gate insulating layer 130, the first interlayer insulating film 141, and the second interlayer insulating film 142. The first anode connection electrode ANDE1 may be a single layer or a multilayer made of any one or more of molybdenum (Mo), aluminum (Al), chromium (Cr), gold (Au), titanium (Ti), nickel (Ni), neodymium (Ne), copper (Cu), and alloys of the same.

The first planarization layer 160 may be formed on the first anode connection electrode ANDE1 to flatten a step due to the active layer ACT, the source electrode S, the drain electrode D, the gate electrode G, the first capacitor electrode CE1, the second capacitor electrode CE2, and the first anode connection electrode ANDE1. The first planarization layer 160 may be made of an organic layer such as acryl resin, epoxy resin, phenolic resin, polyamide resin, and/or polyimide resin.

In an embodiment a protective layer may be additionally formed between the first anode connection electrode ANDE1 and the first planarization layer 160. The protective layer between the first anode connection electrode ANDE1 and the first planarization layer 160 may be made of an inorganic layer, for example, a silicon nitride layer, a silicon oxynitride layer, a silicon oxide layer, a titanium oxide layer, or an aluminum oxide layer.

A second anode connection electrode ANDE2 may be formed on the first planarization layer 160. The second anode connection electrode ANDE2 may be connected to the first anode connection electrode ANDE1 through a contact hole penetrating (or extending through) the first planarization layer 160. The second anode connection electrode ANDE2 may be a single layer or a multilayer made of any one or more of molybdenum (Mo), aluminum (Al), chromium (Cr), gold (Au), titanium (Ti), nickel (Ni), neodymium (Ne), copper (Cu), and alloys of the same.

The second planarization layer 180 may be formed on the second anode connection electrode ANDE2. The second planarization layer 180 may be made of an organic layer such as acryl resin, epoxy resin, phenolic resin, polyamide resin, and/or polyimide resin.

In FIG. 8, the thin-film transistor TFT is formed as a top-gate type in which the gate electrode G is located above the active layer ACT. However, it should be noted that the present disclosure is not limited thereto. That is, the thin-film transistor TFT may also be formed as a bottom-gate type in which the gate electrode G is located under the active layer ACT or a double-gate type in which the gate electrode G is located both above and under the active layer ACT.

The light emitting element layer EML is formed on the thin-film transistor layer TFTL. The light emitting element layer EML includes light emitting elements 170 and a bank 190.

The light emitting elements 170 and the bank 190 are formed on the planarization layer 160. Each of the light emitting elements 170 may include a first light emitting electrode 171, the light emitting layer 172, and a second light emitting electrode 173.

The first light emitting electrode 171 may be formed on the second planarization layer 180. The first light emitting electrode 171 may be connected to the second anode connection electrode ANDE2 through a contact hole penetrating (or extending through) the second planarization layer 180.

In a top emission structure in which light is emitted in a direction from the light emitting layer 172 toward the second light emitting electrode 173, the first light emitting electrode 171 may be made of a metal material having high reflectivity, such as a stacked structure (Ti/Al/Ti) of aluminum and titanium, a stacked structure (ITO/Al/ITO) of aluminum and indium tin oxide, an APC alloy, or a stacked structure (ITO/APC/ITO) of an APC alloy and indium tin oxide. The APC alloy is an alloy of silver (Ag), palladium (Pd), and copper (Cu).

The bank 190 may be formed on the second planarization layer 180 to define the first light emitting electrode 171 so as to define an emission area EMA. The bank 190 may be formed to cover edges of the first light emitting electrode 171. The bank 190 may be made of an organic layer such as acryl resin, epoxy resin, phenolic resin, polyamide resin, and/or polyimide resin.

The emission area EMA is an area in which the first light emitting electrode 171, the light emitting layer 172 and the second light emitting electrode 173 are sequentially stacked so that holes from the first light emitting electrode 171 and electrons from the second light emitting electrode 173 combine together in the light emitting layer 172 to emit light.

The light emitting layer 172 is formed on the first light emitting electrode 171 and the bank 190. The light emitting layer 172 may include an organic material to emit light of a set (e.g., predetermined) color. For example, the light emitting layer 172 may include a hole transporting layer, an organic material layer, and an electron transporting layer.

The second light emitting electrode 173 is formed on the light emitting layer 172. The second light emitting electrode 173 may be formed to cover the light emitting layer 172. The second light emitting electrode 173 may be a common layer common to all subpixels SP1 through SP3 (SP1, SP2, and SP3). A capping layer may be formed on the second light emitting electrode 173.

In the top emission structure, the second light emitting electrode 173 may be made of a transparent conductive material (TCO) capable of transmitting light, such as indium tin oxide (ITO) and/or indium zinc oxide (IZO), and/or a semi-transmissive conductive material such as magnesium (Mg), silver (Ag) or an alloy of Mg and Ag. When the second light emitting electrode 173 is made of a semi-transmissive conductive material, light output efficiency may be increased by a microcavity.

The encapsulation layer TFE may be formed on the light emitting element layer EML. The encapsulation layer TFE may include at least one inorganic layer to prevent or substantially prevent oxygen or moisture from penetrating into the light emitting element layer EML. In addition, the encapsulation layer TFE may include at least one organic layer to protect the light emitting element layer EML from foreign substances such as dust. For example, the encapsulation layer TFE may include a first inorganic layer TFE1, an organic layer TFE2, and a second inorganic layer TFE3.

The first inorganic layer TFE1 may be disposed on the second light emitting electrode 173, the organic layer TFE2 may be disposed on the first inorganic layer TFE1, and the second inorganic layer TFE3 may be disposed on the organic layer TFE2. Each of the first inorganic layer TFE1 and the second inorganic layer TFE3 may be a multilayer in which one or more inorganic layers selected from a silicon nitride layer, a silicon oxynitride layer, a silicon oxide layer, a titanium oxide layer, and an aluminum oxide layer are alternately stacked. The organic layer TFE2 may be a monomer.

The touch electrode layer SENL is disposed on the encapsulation layer TFE. The touch electrode layer SENL includes a second buffer layer BF2, touch electrodes SE, a first touch insulating layer TINS1, and a second touch insulating layer TINS2.

The second buffer layer BF2 may be disposed on the encapsulation layer TFE (e.g., the second inorganic layer TFE3 of the encapsulation layer TFE). The second buffer layer BF2 may include at least one inorganic layer. For example, the second buffer layer BF2 may be a multilayer in which one or more inorganic layers selected from a silicon nitride layer, a silicon oxynitride layer, a silicon oxide layer, a titanium oxide layer, and an aluminum oxide layer are alternately stacked. The second buffer layer BF2 can be omitted.

The first touch insulating layer TINS1 may be disposed on the second buffer layer BF2. The first touch insulating layer TINS1 may be made of an inorganic layer, for example, a silicon nitride layer, a silicon oxynitride layer, a silicon oxide layer, a titanium oxide layer, or an aluminum oxide layer. Alternatively, the first touch insulating layer TINS1 may be made of an organic layer, for example, acryl resin, epoxy resin, phenolic resin, polyamide resin, or polyimide resin.

The touch electrodes SE may be disposed on the first touch insulating layer TINS1. The touch electrodes SE do not overlap the emission area EMA. That is, the touch electrodes SE are not formed in the emission area EMA. Each of the touch electrodes SE may be a single layer made of molybdenum (Mo), titanium (Ti), copper (Cu) or aluminum (Al) or may have a stacked structure (Ti/Al/Ti) of aluminum and titanium, a stacked structure (ITO/Al/ITO) of aluminum and indium tin oxide, an APC alloy, or a stacked structure (ITO/APC/ITO) of an APC alloy and indium tin oxide.

A second touch insulating layer TINS2 may be disposed on the touch electrodes SE. The second touch insulating layer TINS2 may include at least one of an inorganic layer or an organic layer. The inorganic layer may be a silicon nitride layer, a silicon oxynitride layer, a silicon oxide layer, a titanium oxide layer, or an aluminum oxide layer. The organic layer may be acryl resin, epoxy resin, phenolic resin, polyamide resin, or polyimide resin.

The cover window 100 may be disposed on the touch electrode layer SENL. A polarizing film and a shock absorbing layer may be additionally disposed between the touch electrode layer SENL and the cover window 100.

A dam structure DAM may be disposed around the through hole TH. The dam structure DAM may include at least one of the insulating layers BF1, 130, 141, 142, 160, 180 or 190 stacked in the thin-film transistor layer TFTL and the light emitting element layer EML. A groove TCH formed by removing the insulating layers BF1, 130, 141, 142, 160, 180 and 190 may be disposed between the dam structure DAM and the emission area EMA. At least a part of the encapsulation layer TFE (e.g., the organic layer TFE2 of the encapsulation layer TFE) may be disposed in the groove TCH. For example, the organic layer TFE2 of the encapsulation layer TFE may be disposed up to or extend to the dam structure DAM and may not be disposed between the dam structure DAM and the through hole TH. That is, the dam structure DAM may prevent or substantially prevent the organic layer TFE2 from overflowing into the through hole TH. Although the first inorganic layer TFE1 and the second inorganic layer TFE2 end on the dam structure DAM in FIG. 8, the present disclosure is not limited thereto. For example, the first inorganic layer TFE1 and the second inorganic layer TFE2 may end in an area between the dam structure DAM and the through hole TH.

A light blocking pattern 230 may be disposed on a surface of the cover window 100. The light blocking pattern 230 may overlap the dam structure DAM in the third direction (Z-axis direction). The light blocking pattern 230 may overlap an edge of the through hole TH in the third direction (Z-axis direction).

One or more organic layers 228 and 229 may be further disposed on the encapsulation layer TFE in the area between the dam structure DAM and the through hole TH. For example, a first organic layer 228 may be disposed on the second inorganic layer TFE3, and a second organic layer 229 may be disposed on the first organic layer 228. The first organic layer 228 and the second organic layer 229 may fill a space between the dam structure DAM and the through hole TH to flatten the space.

Figure 9:
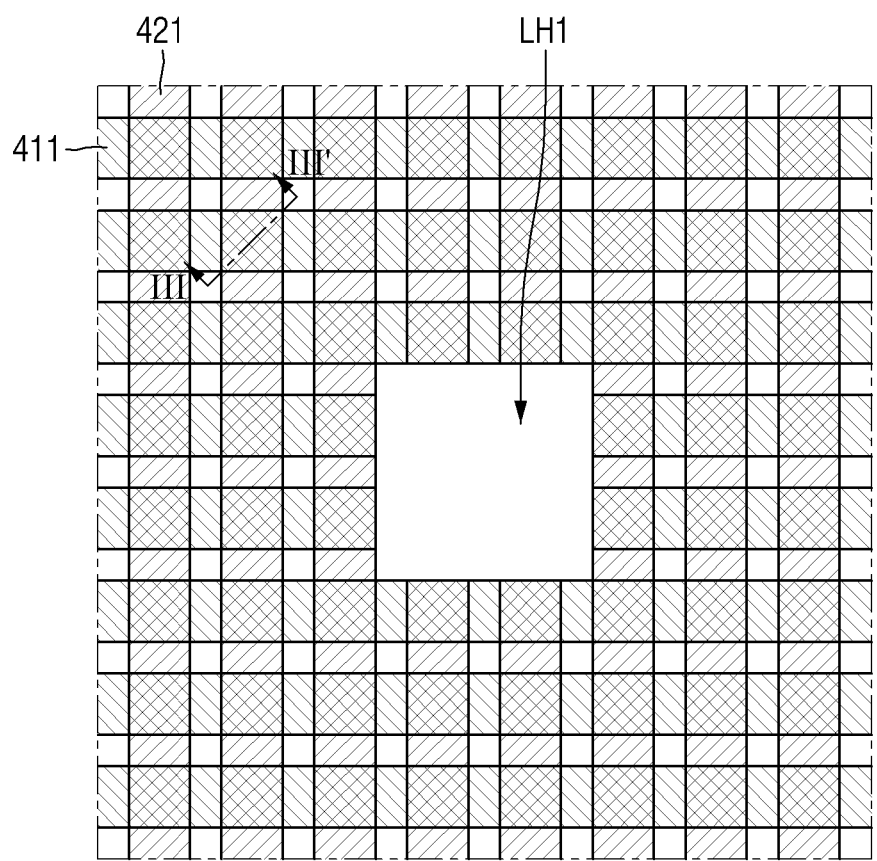
FIG. 9 is a layout view illustrating force sensor electrodes and a first optical hole of the force sensor according to an embodiment.
Figure 9:
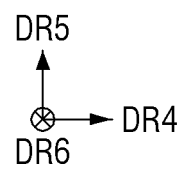
Figure 10:
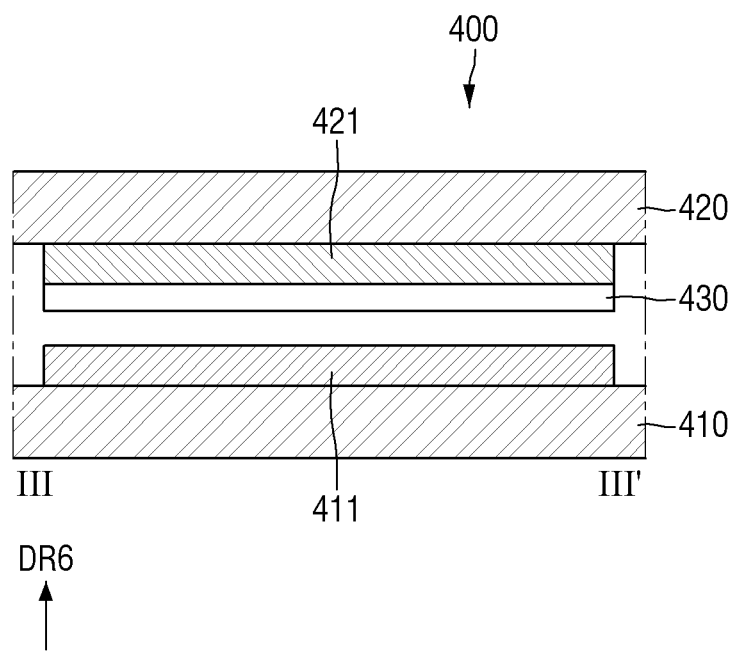
FIG. 10 is a cross-sectional view of an example of the force sensor of FIG. 9.

FIG. 9 is a layout view illustrating force sensor electrodes 411 and 421 and the first optical hole LH1 of the force sensor 400 according to an embodiment. FIG. 10 is a cross-sectional view of an example of the force sensor 400 of FIG. 9. In FIG. 10, an example of a cross-section of the force sensor 400 taken along III-III' of FIG. 9 is illustrated.

Referring to FIGS. 9 and 10, the force sensor 400 may include a first base substrate 410, first force sensor electrodes 411, a second base substrate 420, second force sensor electrodes 421, and a force sensing layer 430 disposed between each of the first force sensor electrodes 411 and each of the second force sensor electrodes 421.

Each of the first base substrate 410 and the second base substrate 420 may include a polyethylene, polyimide, polycarbonate, polysulfone, polyacrylate, polystyrene, polyvinyl chloride, polyvinyl alcohol, polynorbornene, or polyester-based material. In an embodiment, each of the first base substrate 410 and the second base substrate 420 may be made of a polyethylene terephthalate (PET) film or a polyimide film.

The first base substrate 410 and the second base substrate 420 may be bonded to each other by a bonding layer. The bonding layer may include an adhesive material. The bonding layer may be disposed along edges of the first base substrate 410 and the second base substrate 420, but the present disclosure is not limited thereto.

The first force sensor electrodes 411 may be disposed on a surface (e.g., an upper surface) of the first base substrate 410 which faces the second base substrate 420. The second force sensor electrodes 421 may be disposed on a surface (e.g., a lower surface) of the second base substrate 420 which faces the first base substrate 410. The first force sensor electrodes 411 and the second force sensor electrodes 421 may each include a conductive material. For example, the first force sensor electrodes 411 and the second force sensor electrodes 421 may each be made of a metal such as silver (Ag) and/or copper (Cu), a transparent conductive oxide such as ITO, IZO and/or ZIO, carbon nanotubes, and/or a conductive polymer. Any ones of the first force sensor electrodes 411 and the second force sensor electrodes 421 may be force driving electrodes, and the other ones may be force sensing electrodes.

Figure 11:
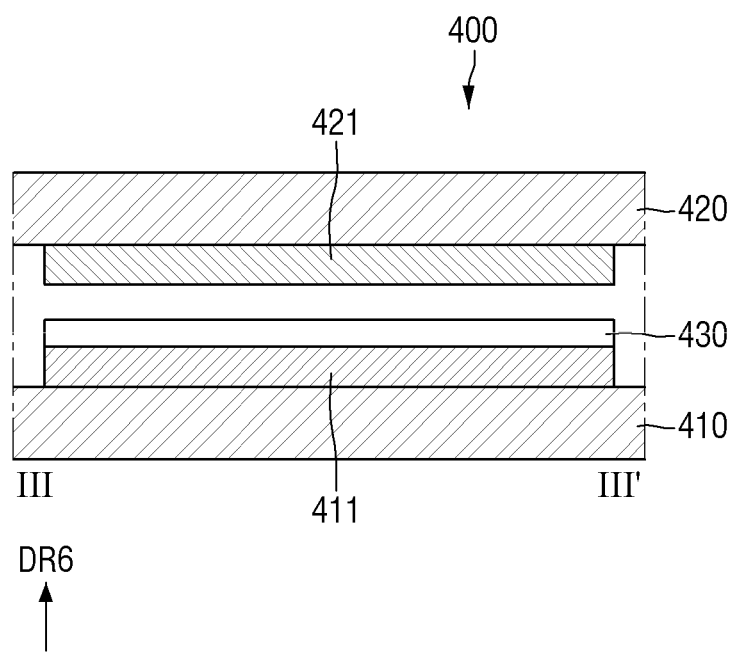
FIG. 11 is a cross-sectional view of an example of the force sensor of FIG. 9.

The force sensing layer 430 may be disposed between each of the first force sensor electrodes 411 and each of the second force sensor electrodes 421 in a sixth direction DR6. The force sensing layer 430 may contact at least any one of each first force sensor electrode 411 and each second force sensor electrode 421. For example, the force sensing layer 430 may contact each second force sensor electrode 421 as illustrated in FIG. 10 or contact each first force sensor electrode 411 as illustrated in FIG. 11.

The force sensing layer 430 may include a force sensitive material. The force sensitive material may include carbon and/or metal nanoparticles, such as nickel, aluminum, tin and/or copper. The force sensitive material may be disposed in a polymer resin in the form of particles, but the present disclosure is not limited thereto.

When force is applied to the force sensor 400, the first force sensor electrodes 411, the force sensing layer 430, and the second force sensor electrodes 412 may be connected (e.g., electrically connected) to each other. The electrical resistance of the force sensing layer 430 may be lowered (or may decrease) according to the force applied to the force sensor 400. The electrical resistance of the force sensing layer 430 may be calculated by applying a force driving voltage to each first force sensor electrodes 411 and measuring a force sensing voltage through each second force sensor electrode 421. Whether force has been applied and the magnitude of the force may be determined or calculated according to the electrical resistance of the force sensing layer 430.

The first force sensor electrodes 411 may extend in a fourth direction DR4 and may be arranged in a fifth direction DR5, which may be normal or perpendicular to the fourth direction DR4. The second force sensor electrodes 421 may extend in the fifth direction DR5 and may be arranged in the fourth direction DR4. The first force sensor electrodes 411 and the second force sensor electrodes 421 may cross each other. Crossings of the first force sensor electrodes 411 and the second force sensor electrodes 421 may be arranged in a matrix shape from a plan view as illustrated in FIG. 9. Each of the crossings of the first force sensor electrodes 411 and the second force sensor electrodes 421 may be a force sensing cell that senses force. That is, force may be sensed at each of the crossings of the first force sensor electrodes 411 and the second force sensor electrodes 421.

When the first force sensor electrodes 411 and the second force sensor electrodes 421 include an opaque conductive material or when the force sensing layer 430 includes an opaque polymer resin, a portion (or portions) of the force sensor 400 may be opaque. To prevent or substantially prevent light passing through the through hole TH from being blocked by the force sensor 400, the force sensor 400 may include the first optical hole LH1. Elements including an opaque material among the first force sensor electrodes 411, the second force sensor electrodes 421 and the force sensing layer 430 may be removed from or may not be present in the first optical hole LH1. For example, when the first force sensor electrodes 411 and the second force sensor electrodes 421 include an opaque conductive material, they may be removed from or may not be present in the first optical hole LH1. When the force sensing layer 430 includes an opaque polymer resin, the force sensing layer 430 may be removed from or may not be present in the first optical hole LH1. When the first force sensor electrodes 411 and the second force sensor electrodes 421 include an opaque conductive material and the force sensing layer 430 includes an opaque polymer resin, the first force sensor electrodes 411, the second force sensor electrodes 421 and the force sensing layer 430 may be removed from or may not be present in the first optical hole LH1.

Although the first force sensor electrodes 411, the second force sensor electrodes 421 and the force sensing layer 430 are described as separate components from the first base substrate 410 and the second base substrate 430, the present disclosure is not limited thereto.

For example, the first force sensor electrodes 411, the second force sensor electrodes 421 and the force sensing layer 430 may be included in (or integral with) the first base substrate 410 and the second base substrate 420. For example, the first force sensor electrodes 411 and the force sensing layer 430 may be included in the first base substrate 410, and the second force sensor electrodes 421 may be included in the second base substrate 420. Alternatively, the first force sensor electrodes 411, the second force sensor electrodes 421, and the force sensing layer 430 may be included in any one of the first base substrate 410 and the second base substrate 420.

Although eight first force sensor electrodes 411 and eight second force sensor electrodes 421 are illustrated in FIG. 9 for ease of description, the numbers of the first force sensor electrodes 411 and the second force sensor electrodes 421 are not limited thereto. In an embodiment, lengths of the force sensor 400 in the fourth direction DR4 and the fifth direction DR5 may each be about 10 mm to about 20 mm. In an embodiment, lengths of the crossings of the first force sensor electrodes 411 and the second force sensor electrodes 421 in the fourth direction DR4 and the fifth direction DR5 may be about 1.5 mm or more. In an embodiment, lengths of the first optical hole LH1 in the fourth direction DR4 and the fifth direction DR5 may each be about 3 mm or more.

Figure 12:
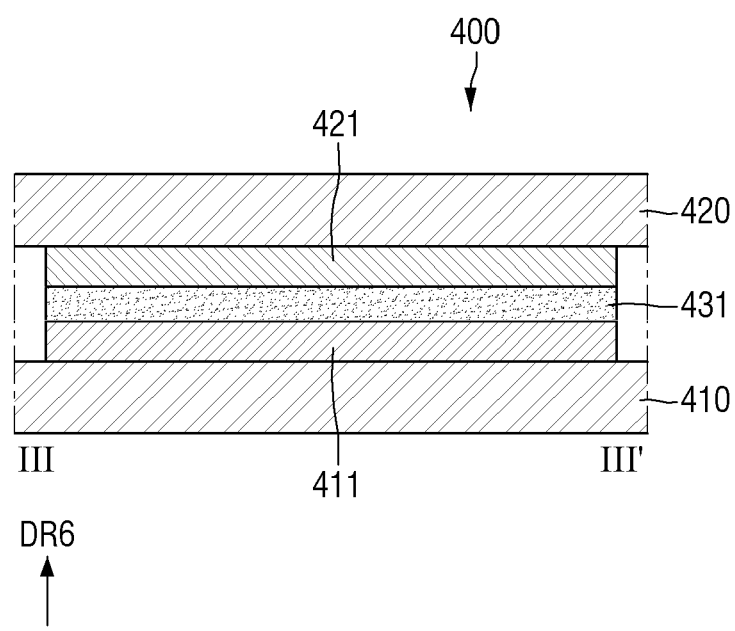
FIG. 12 is a cross-sectional view of an example of the force sensor of FIG. 9.

FIG. 12 is a cross-sectional view of an example of the force sensor 400 of FIG. 9. In FIG. 12, an example of the cross-section of the force sensor 400 taken along III-III' of FIG. 9 is illustrated.

The embodiment of FIG. 12 is different from the embodiments of FIGS. 10 and 11 in that the force sensing layer 430 of the force sensor 400 may be replaced with a variable dielectric constant material layer 431, and the variable dielectric constant material layer 431 contacts both a first force sensor electrode 411 and a second force sensor electrode 421. In other words, a variable dielectric constant material layer 431 may be present in the embodiment of FIG. 12 instead of the force sensing layer 430 of the force sensor 400 as illustrated in the embodiments of FIGS. 10 and 11.

Referring to FIG. 12, the variable dielectric constant material layer 431 may be made of one or more materials from among various suitable materials known to one or ordinary skill in the art such that the dielectric constant of the variable dielectric constant material layer 431 varies according to force applied to the force sensor 400. Because the dielectric constant of the variable dielectric constant material layer 431 varies according to the force applied to the force sensor 400, the magnitude of the force applied to the force sensor 400 may be measured by measuring a value of capacitance between the first force sensor electrode 411 and the second force sensor electrode 412.

Alternatively, the variable dielectric constant material layer 431 may be omitted. In this case, a distance between the first force sensor electrode 411 and the second force sensor electrode 412 may vary according to force applied to the force sensor 400, thereby changing the value of the capacitance between the first force sensor electrode 411 and the second force sensor electrode 412. Therefore, the magnitude of the force applied to the force sensor 400 may be measured or determined by measuring the value of the capacitance between the first force sensor electrode 411 and the second force sensor electrode 412.

Figure 13:
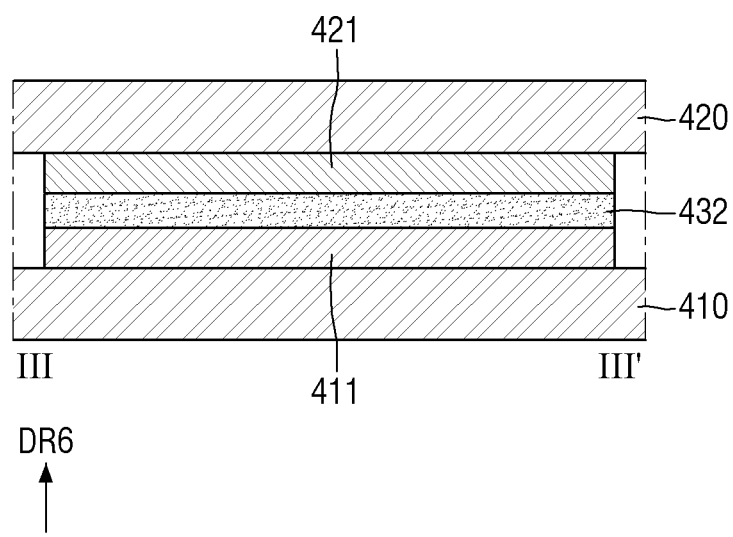
FIG. 13 is a cross-sectional view of an example of the force sensor of FIG. 9.

FIG. 13 is a cross-sectional view of an example of the force sensor 400 of FIG. 9. In FIG. 13, an example of the cross-section of the force sensor 400 taken along III-III' of FIG. 9 is illustrated.

The embodiment of FIG. 13 is different from the embodiments of FIGS. 10 and 11 in that the force sensing layer 430 of the force sensor 400 is replaced with a piezoelectric material layer 432, and the piezoelectric material layer 432 contacts both a first force sensor electrode 411 and a second force sensor electrode 421. In other words, a piezoelectric material layer 432 may be present in the embodiment of FIG. 13 instead of the force sensing layer 430 of the force sensor 400 as illustrated in the embodiments of FIGS. 10 and 11.

Referring to FIG. 13, the piezoelectric material layer 432 may include a piezoelectric material having a piezoelectric effect in which a voltage is generated when mechanical force is applied and an inverse piezoelectric effect in which mechanical deformation occurs when a voltage is applied. For example, the piezoelectric material layer 432 may include polyvinylidene fluoride (PVDF), plumbum ziconate titanate (PZT), or an electroactive polymer.

In the piezoelectric material layer 432, voltages generated in the first force sensor electrode 411 and the second force sensor electrode 421 may vary according to force applied to the force sensor 400 due to the piezoelectric effect. Therefore, the magnitude of the force applied to the force sensor 400 may be measured by measuring the voltages generated in the first force sensor electrode 411 and the second force sensor electrode 421.

Figure 14:
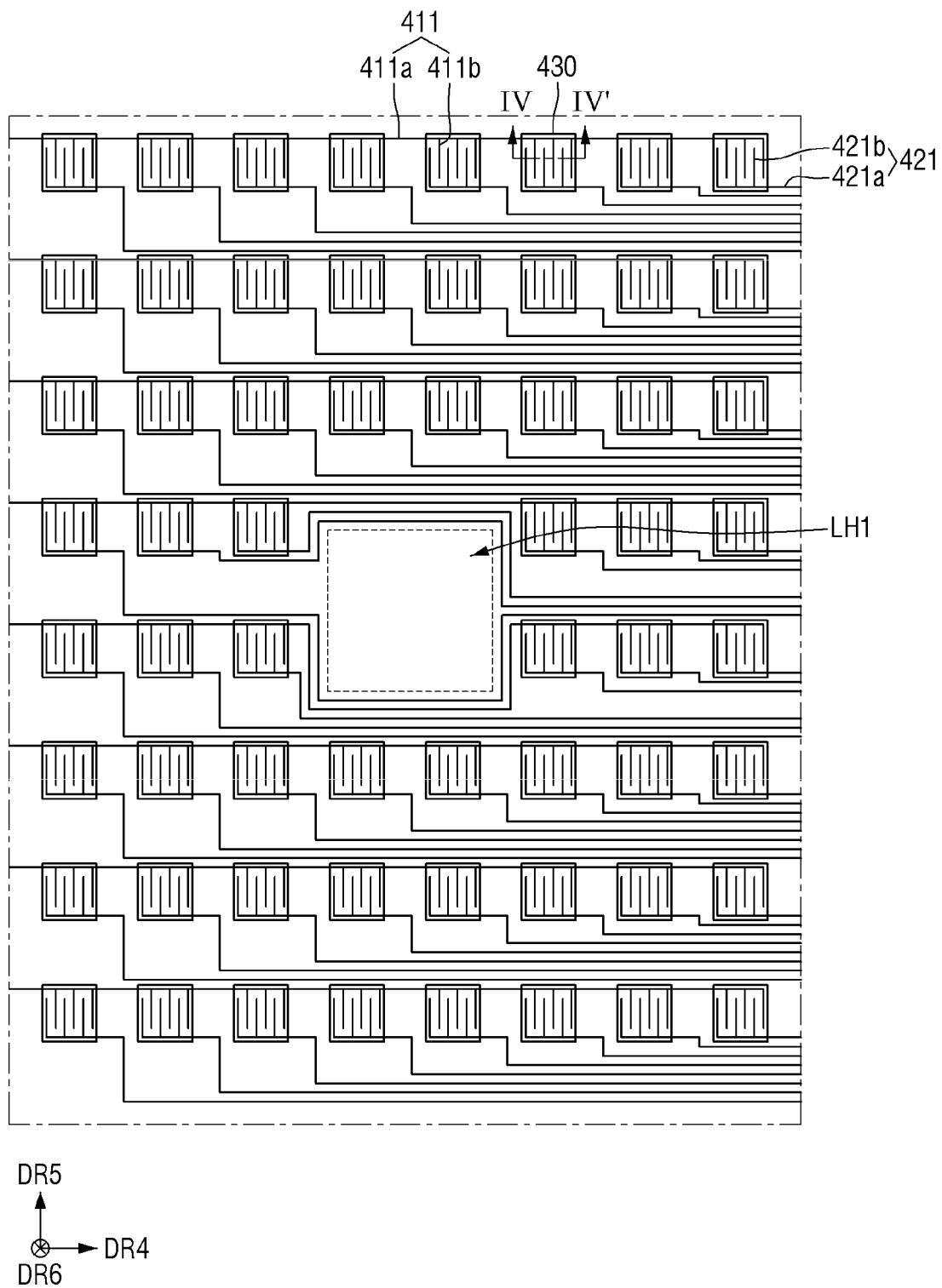
FIG. 14 is a layout view illustrating force sensor electrodes and a first optical hole of a force sensor according to an embodiment.
Figure 15:
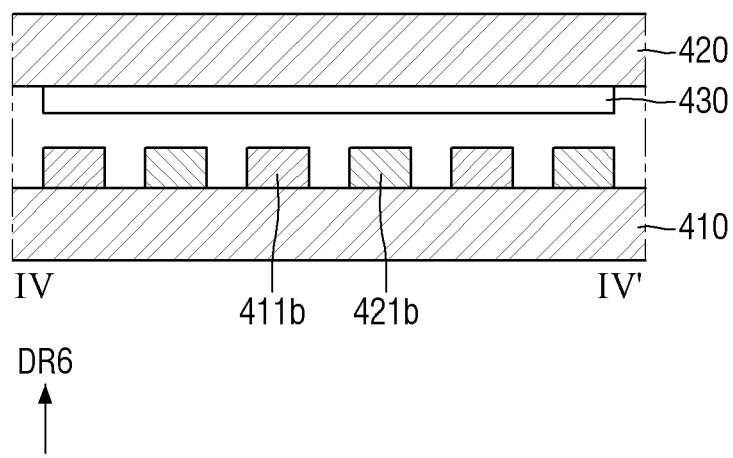
FIG. 15 is a cross-sectional view of an example of the force sensor of FIG. 14.

FIG. 14 is a layout view illustrating force sensor electrodes 411 and 421 and a first optical hole LH1 of a force sensor 400 according to an embodiment. FIG. 15 is a cross-sectional view of an example of the force sensor 400 of FIG. 14. In FIG. 15, an example of a cross-section of the force sensor 400 taken along IV-IV' of FIG. 14 is illustrated.

The embodiment of FIGS. 14 and 15 is different from the embodiments of FIGS. 10 and 11 in that first force sensor electrodes 411 and second force sensor electrodes 421 illustrated in the embodiment of FIGS. 14 and 15 are disposed on the same layer compared to first force sensor electrodes 411 and second force sensor electrodes 421 illustrated in the embodiments of FIGS. 10 and 11.

Referring to FIGS. 14 and 15, the first force sensor electrodes 411 and the second force sensor electrodes 421 may be disposed on a surface of a first base substrate 410 which faces a second base substrate 420. The first force sensor electrodes 411 and the second force sensor electrodes 421 may be electrically separated. The first force sensor electrodes 411 and the second force sensor electrodes 421 may be spaced apart from each other.

Each of the first force sensor electrodes 411 and the second force sensor electrodes 421 may have a comb shape. For example, each of the first force sensor electrodes 411 may include a first stem electrode 411a extending in the fourth direction DR4 and first branch electrodes 411b protruding in the fifth direction DR5, which may be normal or perpendicular to the fourth direction DR4. The first branch electrodes 411b extending in the fifth direction DR5 may protrude from the first stem electrode 411a extending in the fourth direction DR4. Each of the second force sensor electrodes 421 may include a second stem electrode 421a extending in the fourth direction DR4 and second branch electrodes 421b protruding in the fifth direction DR5, which may be normal or perpendicular to the fourth direction DR4. The second branch electrodes 421b may protrude in the fifth direction DR5 from the second stem electrode 421a extending in the fourth direction DR4. The first branch electrodes 411b and the second branch electrodes 421b may be alternately arranged in the fourth direction DR4.

A force sensing layer 430 may be disposed on a surface (e.g., a lower surface) of the second base substrate 420 which faces the first base substrate 410. The first branch electrodes 411b and the second branch electrodes 421b may be alternately disposed in the fourth direction DR4 and may be overlapped by the force sensing layer 430 in the sixth direction DR6.

When force is applied to the force sensor 400, the first force sensor electrodes 411, the force sensing layer 430, and the second force sensor electrodes 412 may be connected (e.g., electrically connected) to each other. The electrical resistance of the force sensing layer 430 may be lowered according to the force applied to the force sensor 400. The electrical resistance of the force sensing layer 430 may be calculated by applying a force driving voltage to each first force sensor electrodes 411 and measuring a force sensing voltage through each second force sensor electrode 421. Whether force has been applied and the magnitude of the force may be determined or calculated according to the electrical resistance of the force sensing layer 430.

When the first force sensor electrodes 411 and the second force sensor electrodes 421 include an opaque conductive material or when the force sensing layer 430 includes an opaque polymer resin, a portion (or portions) of the force sensor 400 may be opaque. To prevent or substantially prevent light passing through the through hole TH from being blocked by the force sensor 400, the force sensor 400 may include the first optical hole LH1. Elements including an opaque material among the first force sensor electrodes 411, the second force sensor electrodes 421 and the force sensing layer 430 may be removed from or may not be present in the first optical hole LH1. For example, when the first force sensor electrodes 411 and the second force sensor electrodes 421 include an opaque conductive material, they may be removed from or may not be present in the first optical hole LH1. When the force sensing layer 430 includes an opaque polymer resin, the force sensing layer 430 may be removed from or may not be present in the first optical hole LH1. When the first force sensor electrodes 411 and the second force sensor electrodes 421 include an opaque conductive material and the force sensing layer 430 includes an opaque polymer resin, the first force sensor electrodes 411, the second force sensor electrodes 421 and the force sensing layer 430 may be removed from or may not be present in the first optical hole LH1. In addition, the first force sensor electrodes 411 and the second force sensor electrodes 421 may bypass or may not be present in the first optical hole LH1.

In FIG. 14, in an embodiment, the force sensing layer 430 overlapping the first branch electrodes 411b and the second branch electrodes 421*b* in the sixth direction DR6 may have a length of about 1.5 mm or more in the fourth direction DR4 and the fifth direction DR5.

Figure 16:
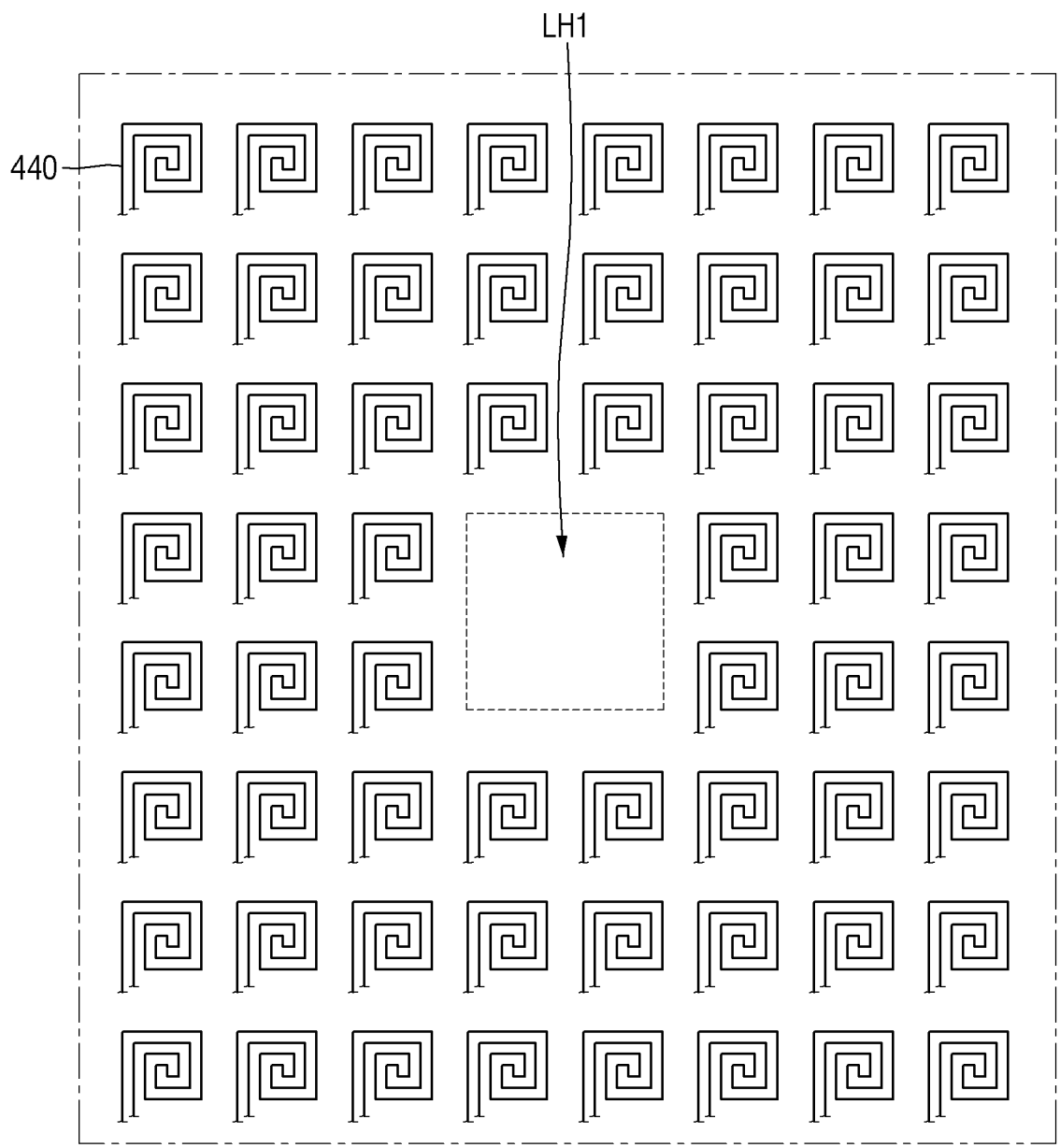
FIG. 16 is a layout view illustrating force sensor electrodes and a first optical hole of a force sensor according to an embodiment.

FIG. 16 is a layout view illustrating force sensor electrodes 440 and a first optical hole LH1 of a force sensor 400 according to an embodiment.

The embodiment of FIG. 16 is different from the embodiment of FIGS. 9 and 10 in that the force sensor 400 includes one type of force sensor electrodes 440 used as strain gauges instead of two types of force sensor electrodes 411 and 421 and does not include the force sensing layer 430. In FIG. 16, force sensor wirings extending from an end to the other end of each of the force sensor electrodes 440 are omitted for ease of description.

Referring to FIG. 16, the force sensor 400 may include the force sensor electrodes 440. The force sensor electrodes 440 may be patterns of a conductive layer formed on a first base substrate 410 (e.g., similar to the first base substrate 410 shown in FIG. 10). The force sensor electrodes 440 may be made of a metal such as silver (Ag) and/or copper (Cu), a transparent conductive oxide such as ITO, IZO and/or ZIO, carbon nanotubes, and/or a conductive polymer. An insulating layer or a second base substrate 420 (e.g., similar to the second base substrate 420 shown in FIG. 10) may be disposed on the force sensor electrodes 440.

The shape of each force sensor electrode 440 may be changed by force applied to the force sensor 400. When the shape of each force sensor electrode 440 is changed, a resistance value sensed by each force sensor electrode 440 may be changed. Therefore, the magnitude of the force may be measured by measuring the resistance value (e.g., the change in resistance value) sensed by each force sensor electrode 440.

To maximize or increase a change in the resistance value of each force sensor electrode 440 when force is applied to the force sensor 400, each force sensor electrode 440 may have a winding shape including a plurality of bent parts in a plan view. For example, as illustrated in FIG. 16, each of the force sensor electrodes 440 may have a tornado shape by repeatedly extending in the fourth direction DR4 and then bending to extend in the fifth direction DR5, bending again to extend in the fourth direction DR4, and then bending again to extend in the fifth direction DR5. Alternatively, each of the force sensor electrodes 440 may have a zigzag shape in a plan view.

When the force sensor electrodes 440 include an opaque conductive material, a portion (or portions) of the force sensor 400 may be opaque. To prevent or substantially prevent light passing through the through hole TH from being blocked by the force sensor 400, the force sensor 400 may include the first optical hole LH1. The force sensor electrodes 440 may be removed from or may not be present in the first optical hole LH1. In addition, force sensor wirings connected to the force sensor electrodes 440 may bypass or may not be present in the first optical hole LH1.

Figure 17:
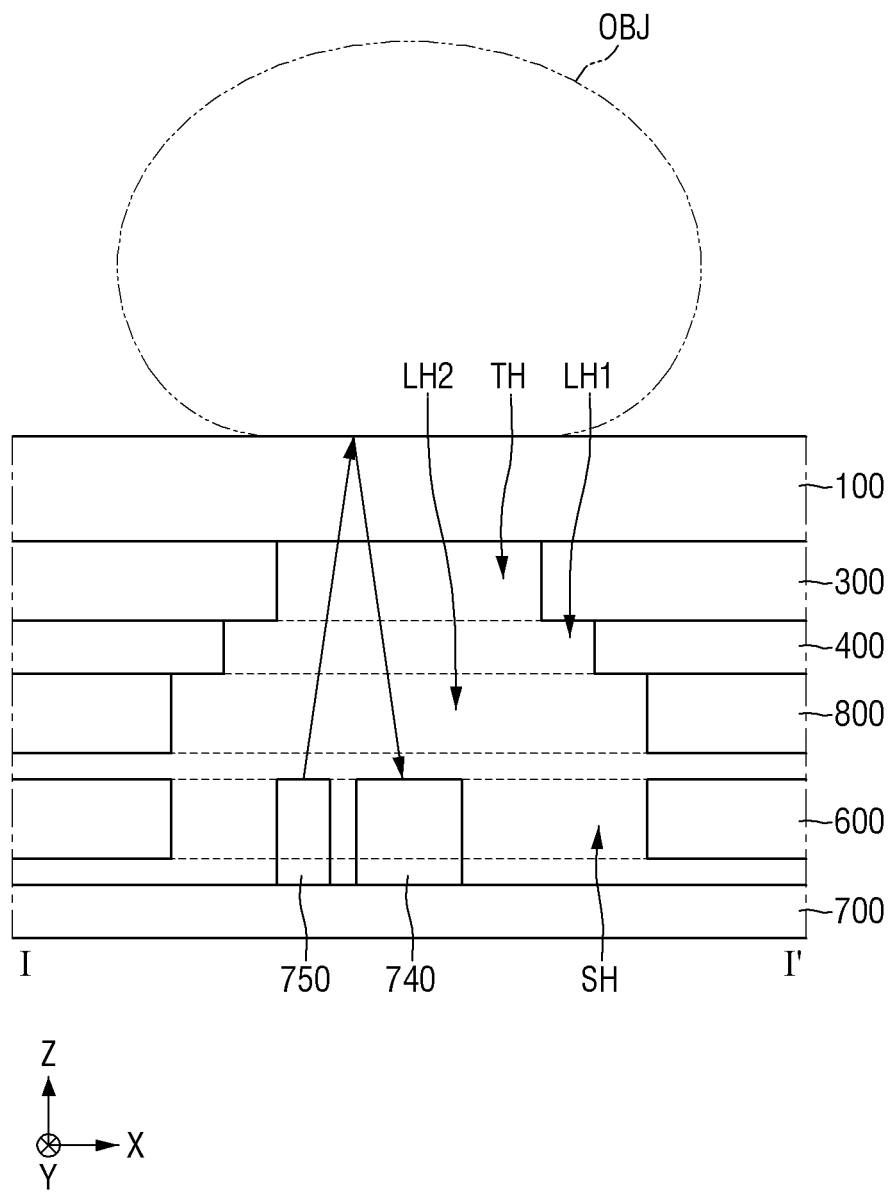
FIG. 17 is a cross-sectional view illustrating a cover window, a display panel, a force sensor, a bottom panel cover, a light emitting device, and a light sensor according to an embodiment.

FIG. 17 is a cross-sectional view illustrating a cover window, a display panel 300, a force sensor 400, a bottom panel cover 800, a light emitting device 750, and a light sensor 740 according to an embodiment.

In FIG. 17, an example of the cross-section of the display device 10 taken along I-I' of FIG. 4 is illustrated. In FIG. 17, a bottom cover 900 is omitted for ease of description.

The embodiment of FIG. 17 is different from the embodiment of FIG. 6 in that the display device 10 further includes the bottom panel cover 800 on a surface (e.g., a lower surface) of the force sensor 400.

Referring to FIG. 17, the bottom panel cover 800 may be attached to a lower surface of the force sensor 400 through an adhesive member. The adhesive member may be a force sensitive adhesive (PSA). The bottom panel cover 800 may include at least one of a light blocking member for absorbing light incident on the at least one light blocking member from the outside, a buffer member for absorbing external impact, or a heat dissipating member for efficiently dissipating the heat of the display panel 300.

The light blocking member may be disposed under the display panel 300. The light blocking member blocks or substantially blocks transmission of light to prevent or substantially prevent elements disposed under the light blocking member (e.g., a display circuit board 310, etc.) from being seen from above the display panel 300. The light blocking member may include a light absorbing material such as a black pigment and/or dye.

The buffer member may be disposed under the light blocking member. The buffer member absorbs external impact to prevent or substantially prevent the display panel 300 from being damaged. The buffer member may be composed of a single layer or a plurality of layers. For example, the buffer member may be made of polymer resin such as polyurethane, polycarbonate, polypropylene and/or polyethylene and/or may be made of an elastic material such as sponge formed by foaming rubber, a urethane-based material and/or an acrylic-based material.

The heat dissipating member may be disposed under the buffer member. The heat dissipating member may include a first heat dissipating layer including graphite or carbon nanotubes and a second heat dissipating layer made of a metal thin film (such as copper, nickel, ferrite and/or silver) capable of shielding electromagnetic waves and having excellent thermal conductivity.

The bottom panel cover 800 may include a second optical hole LH2. The second optical hole LH2 may be an optical hole through which light can pass. Alternatively, the second optical hole LH2 may be a physically formed hole like a hole penetrating (or extending through) the bottom panel cover 800. Alternatively, the second optical hole LH2 may be a combination of a physical hole and an optical hole.

A through hole TH of the display panel 300 may completely overlap the second optical hole LH2 of the bottom panel cover 800. The through hole TH of the display panel 300 may be smaller in size than the second optical hole LH2 of the bottom panel cover 800. A length of the through hole TH in a direction may be smaller (or less) than a length of the second optical hole LH2 in the direction. For example, as illustrated in FIG. 17, a length of the through hole TH in the first direction (X-axis direction) may be smaller (or less) than a length of the second optical hole LH2 in the first direction (X-axis direction).

In addition, a first optical hole LH1 of the force sensor 400 may completely overlap the second optical hole LH2 of the bottom panel cover 800. The first optical hole LH1 of the force sensor 400 may be smaller in size than the second optical hole LH2 of the bottom panel cover 800. A length of the first optical hole LH1 in a direction may be smaller (or less) than a length of the second optical hole LH2 in the direction. For example, as illustrated in FIG. 17, a length of the first optical hole LH1 in the first direction (X-axis direction) may be smaller (or less) than the length of the second optical hole LH2 in the first direction (X-axis direction).

In addition, the second optical hole LH2 of the bottom panel cover 800 may completely overlap a sensor hole SH of a bracket 600. The second optical hole LH2 of the bottom panel cover 800 may be smaller in size than the sensor hole SH of the bracket 600. A length of the second optical hole LH2 in a direction may be smaller (or less) than a length of the sensor hole SH in the direction. For example, as illustrated in FIG. 17), the length of the second optical hole LH2 in the first direction (X-axis direction) may be smaller (or less) than a length of the sensor hole SH in the first direction (X-axis direction). Therefore, light passing through the through hole TH, the first optical hole LH1, the second optical hole LH2, and the sensor hole SH may be incident on the light sensor 740.

The light sensor 740 and the light emitting device 750 may be disposed in the sensor hole SH of the bracket 600. Alternatively, when the light sensor 740 and the light emitting device 750 are long in the third direction (Z-axis direction), the light sensor 740 and the light emitting device 750 may be disposed in the second optical hole LH2 of the bottom panel cover 800, in the first optical hole LH1 of the force sensor 400 and the second optical hole LH2 of the bottom panel cover 800, or in all of the through hole TH of the display panel 300, the first optical hole LH1 of the force sensor 400 and the second optical hole LH2 of the bottom panel cover 800. In this case, the through hole TH of the display panel 300, the first optical hole LH1 of the force sensor 400, and the second optical hole LH2 of the bottom panel cover 800 may all be physical holes.

Figure 18:
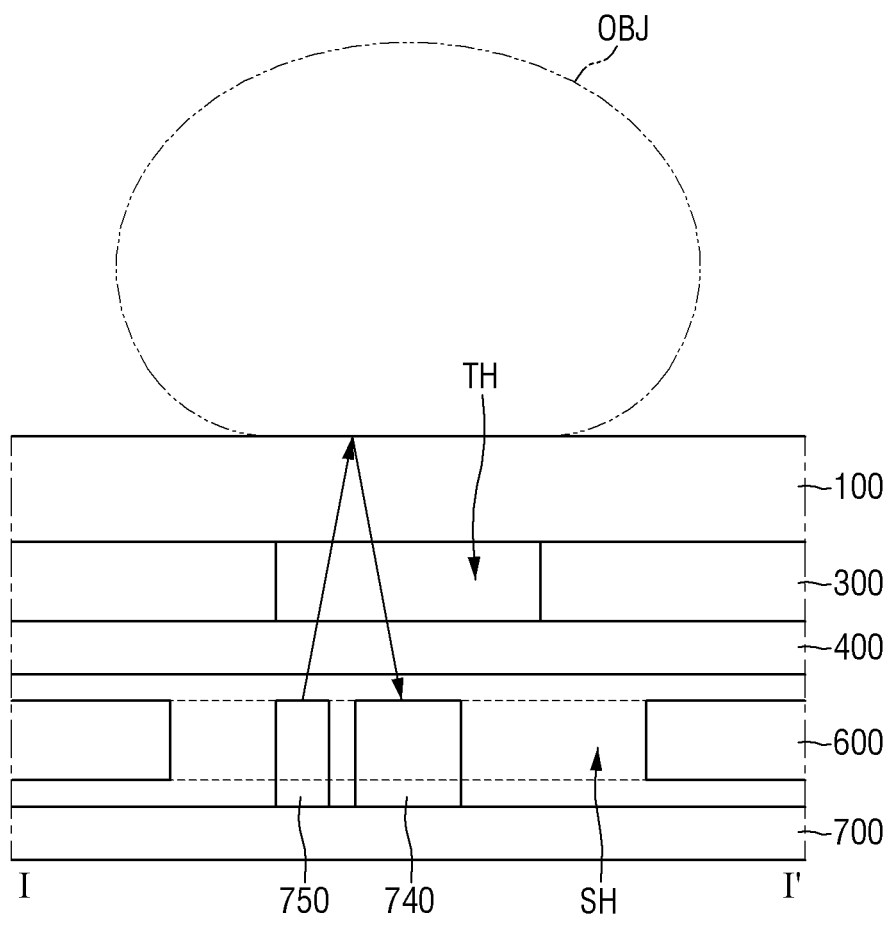
FIG. 18 is a cross-sectional view illustrating a cover window, a display panel, a transparent force sensor, a light emitting device, and a light sensor according to an embodiment.

FIG. 18 is a cross-sectional view illustrating a cover window, a display panel 300, a force sensor 400, a light emitting device 750, and a light sensor 740 according to an embodiment.

In FIG. 18, an example of the cross-section of the display device 10 taken along I-I' of FIG. 4 is illustrated. In FIG. 18, a bottom cover 900 is omitted for ease of description.

The embodiment of FIG. 18 is different from the embodiment of FIG. 6 in that a first optical hole LH1 is removed from or is not present in the force sensor 400.

Figure 19:
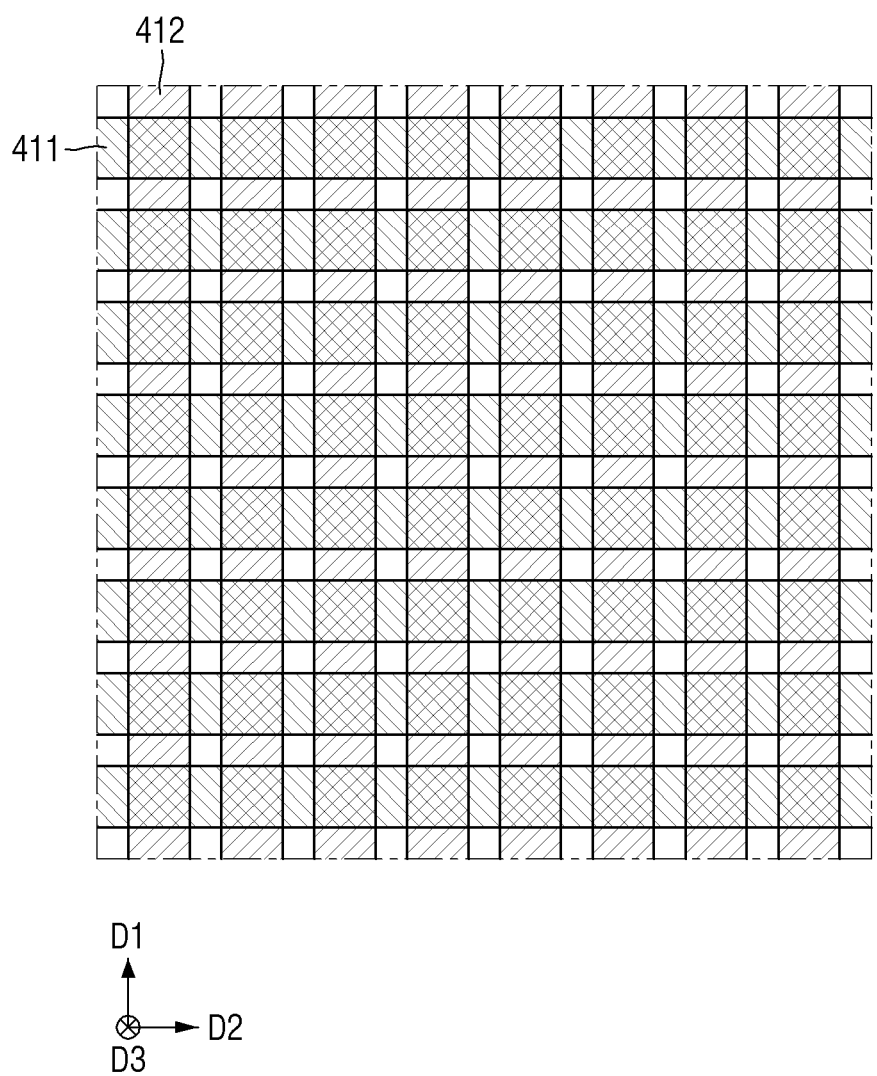
FIG. 19 is a layout view illustrating force sensor electrodes of a force sensor according to an embodiment.

Referring to FIG. 18, the force sensor 400 may be formed to be transparent so that light can pass through the force sensor 400. For example, when the force sensor 400 includes a force sensing layer 430 to sense force as illustrated in FIGS. 9-11, 14, and 15, a first base substrate 410 and a second base substrate 420 may include a transparent material, first force sensor electrodes 411 and second force sensor electrodes 421 may include a transparent conductive material, and the force sensing layer 430 may include a transparent polymer resin. In this case, because light can pass through the force sensor 400, the first optical hole LH1 is not necessary in the force sensor 400 as illustrated in FIG. 19.

In addition, when the force sensor 400 includes a variable dielectric constant material layer 431 to sense force as illustrated in FIG. 12, the variable dielectric constant material layer 431 may include a transparent insulating material. In this case, because light can pass through the force sensor 400, the first optical hole LH1 is not necessary in the force sensor 400.

In addition, when the force sensor 400 includes a piezoelectric material layer 432 to sense force as illustrated in FIG. 13, the piezoelectric material layer 432 may include transparent polyvinylidene fluoride (PVDF). In this case, because light can pass through the force sensor 400, the first optical hole LH1 is not necessary in the force sensor 400.

In addition, when the force sensor 400 includes force sensor electrodes 440 used as strain gauges to sense force as illustrated in FIG. 16, the force sensor electrodes 440 may include a transparent conductive material. In this case, because light can pass through the force sensor 400, the first optical hole LH1 is not necessary in the force sensor 400.

Figure 20:
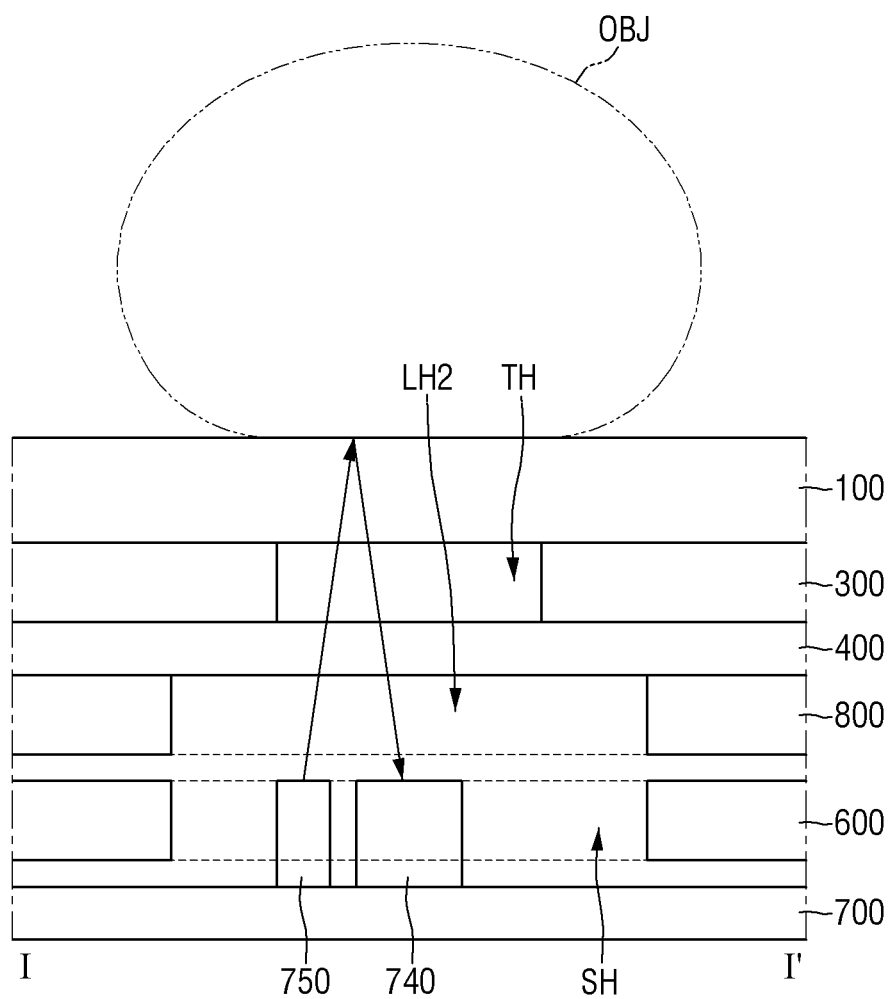
FIG. 20 is a cross-sectional view illustrating a cover window, a display panel, a transparent force sensor, a bottom panel cover, a light emitting device, and a light sensor according to an embodiment.

FIG. 20 is a cross-sectional view illustrating a cover window, a display panel 300, a force sensor 400, a bottom panel cover 800, a light emitting device 750, and a light sensor 740 according to an embodiment.

In FIG. 20, an example of the cross-section of the display device 10 taken along I-I' of FIG. 4 is illustrated. In FIG. 20, a bottom cover 900 is omitted for ease of description.

The embodiment of FIG. 20 is different from the embodiment of FIG. 6 in that the display device 10 further includes the bottom panel cover 800 on a surface of the force sensor 400, and a first optical hole LH1 is removed from or is not present in the force sensor 400.

Because the bottom panel cover 800 illustrated in FIG. 20 is substantially the same as that described with reference to FIG. 17, a description of the bottom panel cover 800 is omitted. In addition, because the force sensor 400 illustrated in FIG. 20 is substantially the same as that described with reference to FIG. 18, a description of the force sensor 400 is omitted or not repeated.

Figure 21:
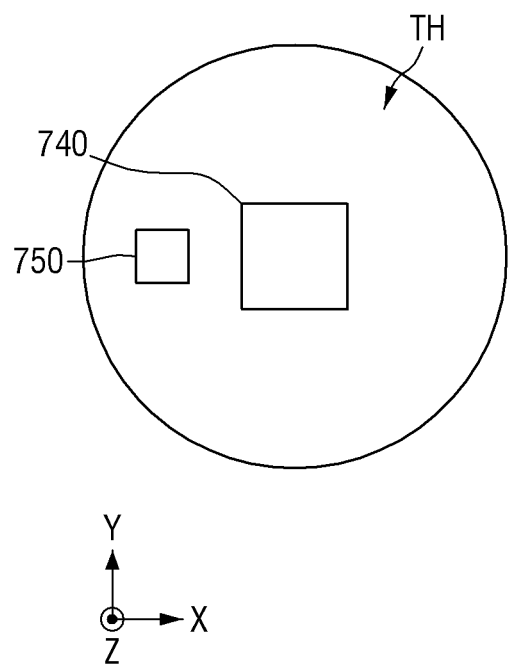
FIG. 21 is a layout view illustrating a light emitting device and a light sensor disposed in a through hole according to an embodiment.

FIG. 21 is a layout view illustrating a light emitting device 750 and a light sensor 740 disposed in a through hole TH according to an embodiment. In FIG. 21, the light sensor 740 and the light emitting device 750 disposed in the through hole TH when seen in a plan view are illustrated.

Referring to FIG. 21, the light sensor 740 may be disposed at the center of the through hole TH, and the light emitting device 750 may be disposed near the light sensor 740. The light emitting device 750 may be disposed adjacent to a side of the light sensor 740. For example, the light emitting device 750 may be disposed on or adjacent to a left side of the light sensor 740 as illustrated in FIG. 21.

Figure 22:
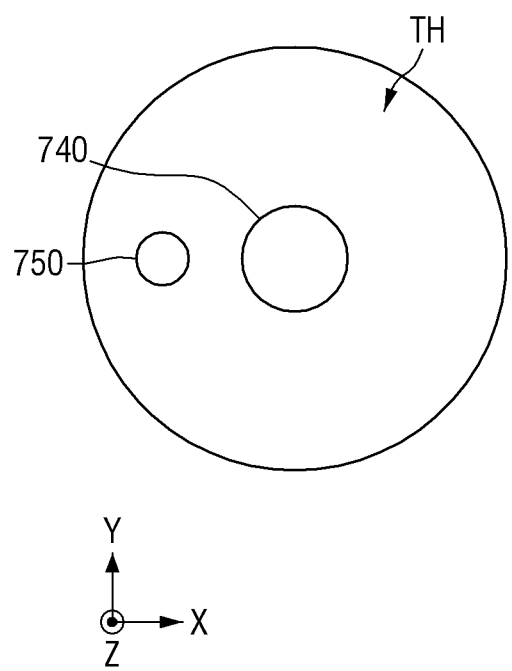
FIG. 22 is a layout view illustrating a light emitting device and a light sensor disposed in a through hole according to an embodiment.

In addition, although the light sensor 740 and the light emitting device 750 have a quadrangular planar shape in FIG. 21, the present disclosure is not limited thereto. The light sensor 740 and the light emitting device 750 may also have a circular planar shape as illustrated in FIG. 22. Alternatively, the light sensor 740 and the light emitting device 750 may have a polygonal planar shape other than the quadrangular planar shape or an oval planar shape.

In addition, although the planar shape of the light sensor 740 and the planar shape of the light emitting device 750 are the same in FIG. 21, the present disclosure is not limited thereto. The planar shape of the light sensor 740 and the planar shape of the light emitting device 750 may also be different.

Figure 23:
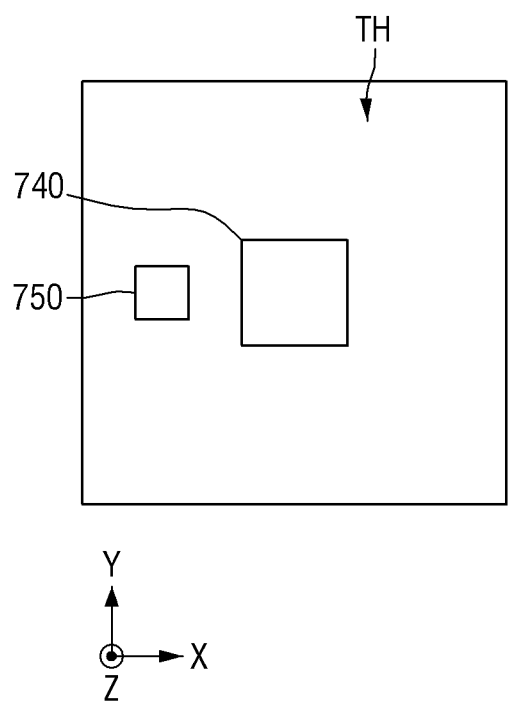
FIG. 23 is a layout view illustrating a light emitting device and a light sensor disposed in a through hole according to an embodiment.

In addition, although the through hole TH has a circular planar shape in FIG. 21, the present disclosure is not limited thereto. The through hole TH may also have a quadrangular planar shape as illustrated in FIG. 23. Alternatively, the through hole TH may have a polygonal planar shape other than the quadrangular planar shape or an oval planar shape.

Figure 24:
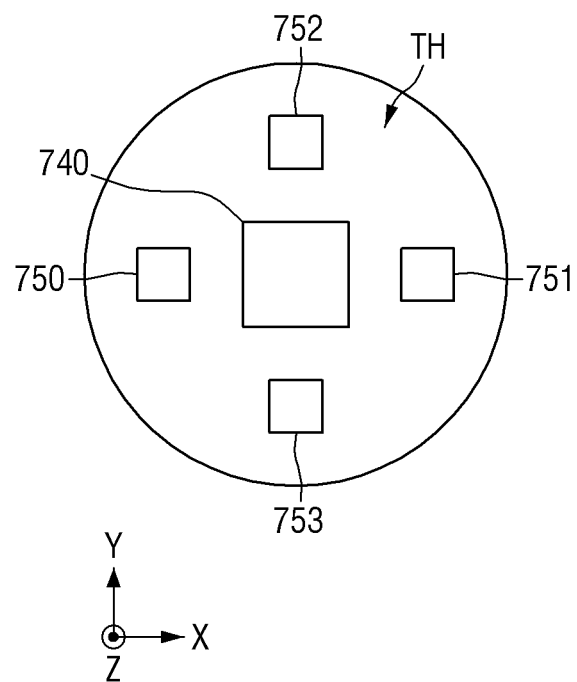
FIG. 24 is a layout view illustrating a light emitting device and a light sensor disposed in a through hole according to an embodiment.

In addition, although one light sensor 740 and one light emitting device 750 are disposed in the through hole TH in FIG. 21, the present disclosure is not limited thereto. The through hole TH may include one light sensor 740 and a plurality of light emitting devices 750 through 753 (a first light emitting device 750, a second light emitting device 751, a third light emitting device 752, and a fourth light emitting device 753). For example, the through hole TH may include one light sensor 740 and four light emitting devices 750 through 753 as illustrated in FIG. 24. In this case, the light sensor 740 may be disposed at the center of the through hole TH, and the light emitting devices 750 through 753 may be disposed around the light sensor 740. For example, a first light emitting device 750 may be disposed on a left side of the light sensor 740, a second light emitting device 751 may be disposed on a right side of the light sensor 740, a third light emitting device 752 may be disposed on an upper side of the light sensor 740, and a fourth light emitting device 753 may be disposed on a lower side of the light sensor 740. In other words, the light sensor 740 may be disposed between the first light emitting device 750 and the second light emitting device 751, and between the third light emitting device 752 and the fourth light emitting device 753 such that the plurality of light emitting devices 750 through 753 form a cross shape.

Figure 25:
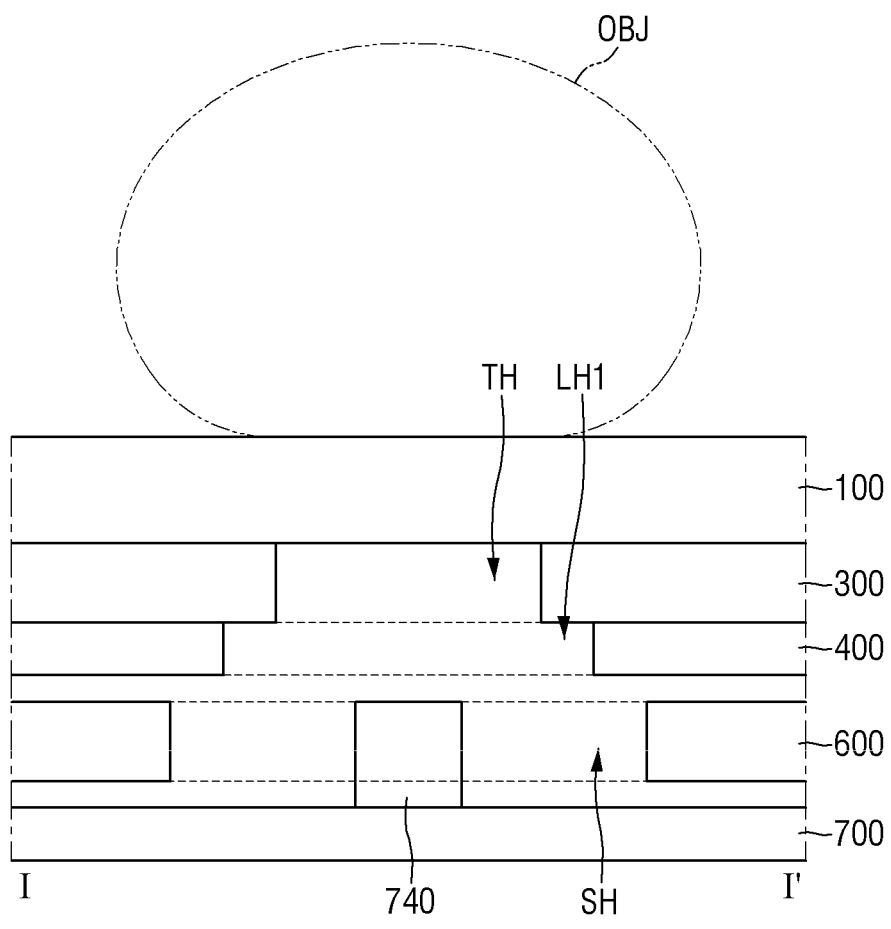
FIG. 25 is a cross-sectional view illustrating a cover window, a display panel, a force sensor, and a light sensor according to an embodiment.

FIG. 25 is a cross-sectional view illustrating a cover window, a display panel 300, a force sensor 400, and a light sensor 740 according to an embodiment.

The embodiment of FIG. 25 is different from the embodiment of FIG. 6 in that a light emitting device 750 is omitted.

Referring to FIG. 25, because the light emitting device 750 is omitted, the light sensor 740 may sense light reflected by a user's finger OBJ from among light emitted from pixels PX of the display panel 300 instead of the light emitting device 750. Specifically, light emitted from the pixels PX of the display panel 300 may be absorbed or reflected by blood vessels of the user's finger OBJ through a first optical hole LH1 of the force sensor 400 and a through hole TH of the display panel 300. The light reflected by the blood vessels of the user's finger OBJ may be sensed by the light sensor 740 through the through hole TH of the display panel 300 and the first optical hole LH1 of the force sensor 400.

Figure 26:
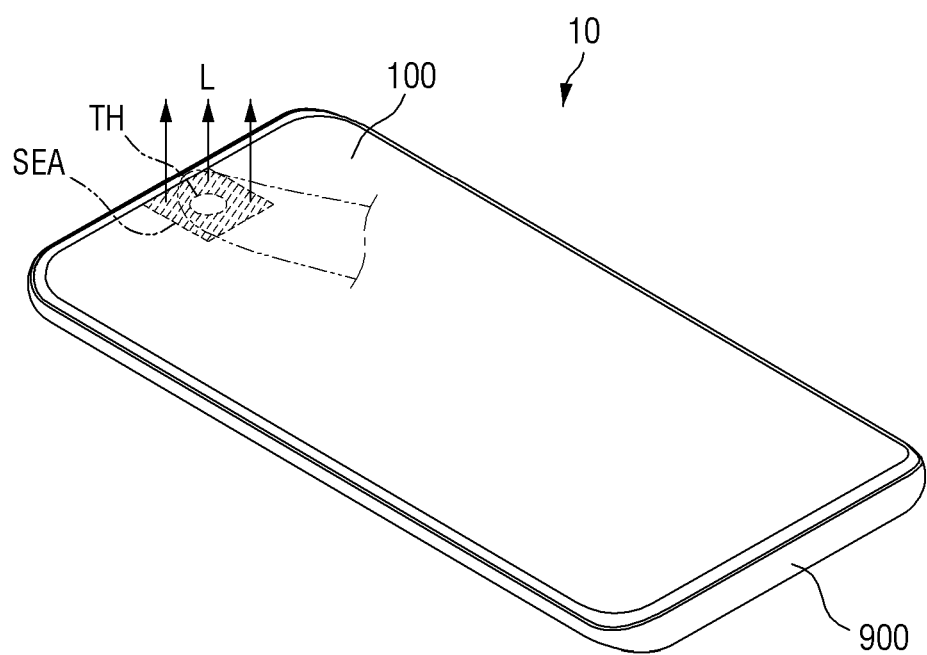
FIG. 26 is a schematic perspective view illustrating a light emitting area of a display device according to an embodiment.

FIG. 26 is a schematic perspective view illustrating an area that emits light in a blood pressure measurement mode in a display device 10 according to an embodiment.

Referring to FIG. 26, when a light emitting device 750 is omitted, light emitted from pixels PX of a display panel 300 may be irradiated to a user's finger OBJ. For example, pixels PX of a sensor emission area SEA of a display area DA may emit light as illustrated in FIG. 26. The sensor emission area SEA may be defined as an area disposed around a through hole TH in the display area DA. The sensor emission area SEA may surround the through hole TH. Alternatively, the sensor emission area SEA may be disposed on at least one side of the through hole TH.

The wavelength of light emitted from the pixels PX of the sensor emission area SEA in the blood pressure measurement mode may be an infrared wavelength, a blue wavelength of visible light, a red wavelength of visible light, or a green wavelength of visible light. Here, when a body part disposed on the through hole TH is a finger OBJ, because blood vessels of the finger OBJ are tiny, if the wavelength of light emitted from the pixels PX of the sensor emission area SEA is the infrared wavelength or the red wavelength of visible light, the light can easily penetrate into and be absorbed by the blood vessels (e.g., tiny blood vessels) of the finger OBJ because the infrared wavelength and the red wavelength of visible light are longer than the green wavelength of visible light or the blue wavelength of visible light. In addition, when the body part disposed on the through hole TH is a wrist, because arteries of the wrist are sufficiently thick, even if the wavelength of light emitted from the pixels PX of the sensor emission area SEA is the green wavelength of visible light, the light can penetrate into and be absorbed by the arteries of the wrist. Accordingly, the wavelength of light emitted from the pixels PX of the sensor emission area SEA may be determined according to a part of the body to measure blood pressure.

In addition, to increase the proportion of light sensed by a light sensor 740 in the blood pressure measurement mode, luminance (e.g., maximum luminance) of light emitted from the pixels PX of the sensor emission area SEA may be different in the blood pressure measurement mode for measuring blood pressure and a display mode for displaying an image. The luminance (e.g., maximum luminance) of light emitted from the pixels PX of the sensor emission area SEA may be higher in the blood pressure measurement mode than in the display mode. For example, the maximum luminance of light emitted from the pixels PX of the sensor emission area SEA in the display mode may be about 400 nits. On the other hand, the maximum luminance of light emitted from the pixels PX of the sensor emission area SEA in the blood pressure measurement mode may be about 500 nits to about 2500 nits.

Figure 28:
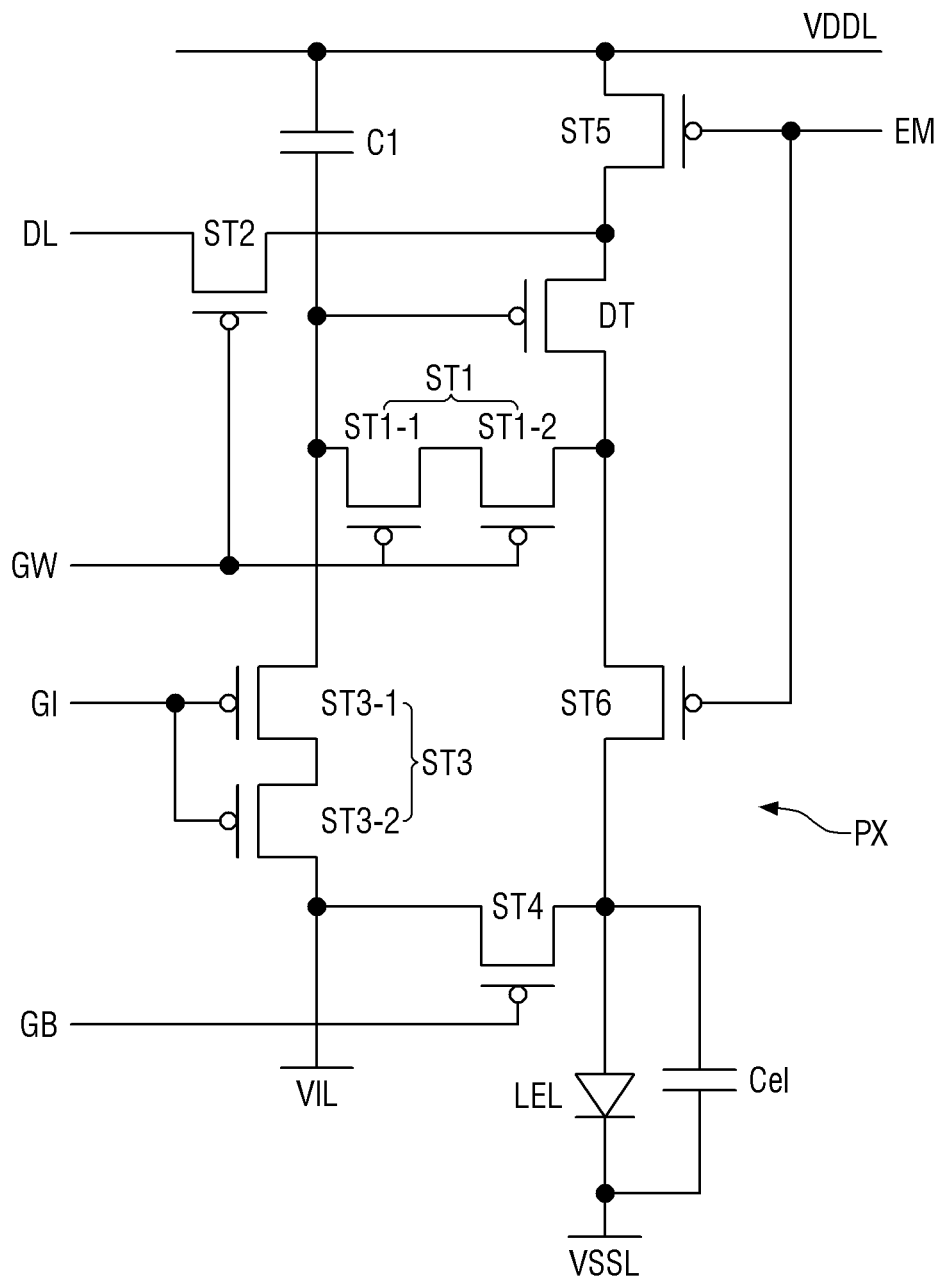
FIG. 28 is a schematic circuit diagram of a pixel of a display area.

In order to make the luminance of light emitted from the pixels PX of the sensor emission area SEA higher in the blood pressure measurement mode than in the display mode, a first driving voltage of a first driving voltage wiring VDDL (e.g., see FIG. 28) of each pixel PX may be higher in the blood pressure measurement mode than in the display mode as illustrated in FIG. 28.

Figure 27:
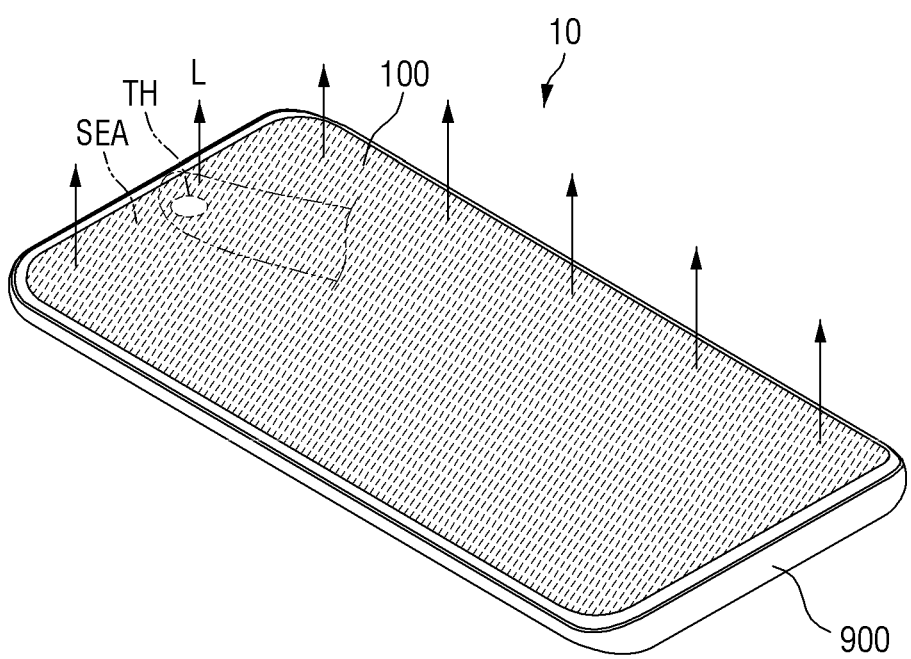
FIG. 27 is a schematic perspective view illustrating an area that emits light when blood pressure is measured by a display device according to an embodiment.
Figure 27:
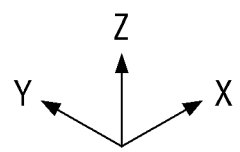

FIG. 27 is a schematic perspective view illustrating an area that emits light when blood pressure is measured by a display device according to an embodiment.

The embodiment of FIG. 27 is different from the embodiment of FIG. 26 in that all pixels PX of a display area DA emit light in a blood pressure measurement mode. In other words, the sensor emission area SEA includes all of the pixels PX of the display area DA.

FIG. 28 is a schematic circuit diagram of a pixel PX of a display area.

Referring to FIG. 28, the pixel PX may be connected to a first initialization scan wiring GI, a write scan wiring GW, a second initialization scan wiring GB, an emission wiring EM, and a data wiring DL. In addition, the pixel PX may be connected to a first driving voltage wiring VDDL to which a first driving voltage is supplied, an initialization voltage wiring VIL to which an initialization voltage Vini is supplied, and a second driving voltage wiring VSSL to which a second driving voltage is supplied.

The pixel PX includes a driving transistor DT, a light emitting element LEL, switch elements, and a capacitor C1. The switch elements include first through sixth transistors ST1 through ST6 (a first transistor ST1, a second transistor ST2, a third transistor ST3, a fourth transistor ST4, a fifth transistor ST5, a sixth transistor ST6).

The driving transistor DT may include a gate electrode, a first electrode, and a second electrode. The driving transistor DT controls a drain-source current Ids (hereinafter, referred to as a "driving current") flowing between the first electrode and the second electrode according to a data voltage applied to the gate electrode. The driving current Ids flowing through a channel of the driving transistor DT is proportional to the square of a difference between a voltage Vgs between the gate electrode and a source electrode of the driving transistor DT and a threshold voltage as shown in Equation 1.

$$Ids = k' \times (Vgs - Vth)^2 \quad (1)$$

In Equation 1, k' is a proportional coefficient determined by the structure and physical properties of a driving transistor, Vgs is a gate-source voltage of the driving transistor, and Vth is a threshold voltage of the driving transistor.

The light emitting element LEL emits light according to the driving current Ids. The amount of light emitted from the light emitting element LEL may be proportional to the driving current Ids.

The light emitting element LEL may be an organic light emitting diode including an anode, a cathode, and an organic light emitting layer disposed between the anode and the cathode. Alternatively, the light emitting element LEL may be an inorganic light emitting element including an anode, a cathode, and an inorganic semiconductor disposed between the anode and the cathode. Alternatively, the light emitting element LEL may be a quantum dot light emitting element including an anode, a cathode, and a quantum dot light emitting layer disposed between the anode and the cathode. Alternatively, the light emitting element LEL may be a micro light emitting diode.

The anode of the light emitting element LEL may be connected to a first electrode of the fourth transistor ST4 and a second electrode of the sixth transistor ST6, and the cathode may be connected to the second driving voltage wiring VSSL. A parasitic capacitance Cel may be formed between the anode and the cathode of the light emitting element LEL.

The first transistor ST1 may be a dual transistor including a $(1-1)^{th}$ transistor ST1-1 and a $(1-2)^{th}$ transistor ST1-2. The $(1-1)^{th}$ transistor ST1-1 and the $(1-2)^{th}$ transistor ST1-2 are turned on by a scan signal of the write scan wiring GW to connect the gate electrode and the second electrode of the driving transistor DT. That is, because the gate electrode and the second electrode of the driving transistor DT are connected when the $(1-1)^{th}$ transistor ST1-1 and the $(1-2)^{th}$ transistor ST1-2 are turned on, the driving transistor DT operates a diode. The $(1-1)^{th}$ transistor ST1-1 may have a gate electrode connected to the write scan wiring GW, a first electrode connected to a second electrode of the $(1-2)^{th}$ transistor ST1-2, and a second electrode connected to the gate electrode of the driving transistor DT. The $(1-2)^{th}$ transistor ST1-2 may have a gate electrode connected to the write scan wiring GW, a first electrode connected to the second electrode of the driving transistor DT, and the second electrode connected to the first electrode of the $(1-1)^{th}$ transistor ST1-1.

The second transistor ST2 is turned on by the scan signal of the write scan wiring GW to connect the first electrode of the driving transistor DT and the data wiring DL. The second transistor ST2 may have a gate electrode connected to the write scan wiring GW, a first electrode connected to the first electrode of the driving transistor DT, and a second electrode connected to the data wiring DL.

The third transistor ST3 may be a dual transistor including a $(3-1)^{th}$ transistor ST3-1 and a $(3-2)^{th}$ transistor ST3-2. The $(3-1)^{th}$ transistor ST3-1 and the $(3-2)^{th}$ transistor ST3-2 are turned on by a scan signal of the first initialization scan wiring GI to connect the gate electrode of the driving transistor DT and the initialization voltage wiring VIL. The gate electrode of the driving transistor DT may be discharged to an initialization voltage of the initialization voltage wiring VIL. The $(3-1)^{th}$ transistor ST3-1 may have a gate electrode connected to the first initialization scan wiring GI, a first electrode connected to the gate electrode of the driving transistor DT, and a second electrode connected to a first electrode of the $(3-2)^{th}$ transistor ST3-2. The $(3-2)^{th}$ transistor ST3-2 may have a gate electrode connected to the first initialization scan wiring GI, the first electrode connected to the second electrode of the $(3-1)^{th}$ transistor ST3-1, and a second electrode connected to the initialization voltage wiring VIL.

The fourth transistor ST4 is turned on by a scan signal of the second initialization scan wiring GB to connect the anode of the light emitting element LEL and the initialization voltage wiring VIL. The anode of the light emitting element LEL may be discharged to the initialization voltage. The fourth transistor ST4 may have a gate electrode connected to the second initialization scan wiring GB, the first electrode connected to the anode of the light emitting element LEL, and a second electrode connected to the initialization voltage wiring VIL.

The fifth transistor ST5 is turned on by an emission control signal of the emission wiring EM to connect the first electrode of the driving transistor DT and the first driving voltage wiring VDDL. The fifth transistor ST5 has a gate electrode connected to the emission wiring EM, a first electrode connected to the first driving voltage wiring VDDL, and a second electrode connected to the source electrode of the driving transistor DT.

The sixth transistor ST6 is connected between the second electrode of the driving transistor DT and the anode of the light emitting element LEL. The sixth transistor ST6 is turned on by the emission control signal of the emission wiring EM to connect the second electrode of the driving transistor DT and the anode of the light emitting element LEL. The sixth transistor ST6 has a gate electrode connected to the emission wiring EM, a first electrode connected to the second electrode of the driving transistor DT, and the second electrode connected to the anode of the light emitting element LEL. When both the fifth transistor ST5 and the sixth transistor ST6 are turned on, the driving current Ids may be supplied to the light emitting element LEL.

The capacitor C1 is formed between the gate electrode of the driving transistor DT and the first driving voltage wiring VDDL. An electrode of the capacitor C1 may be connected to the gate electrode of the driving transistor DT, and the other electrode may be connected to the first driving voltage wiring VDDL.

When the first electrode of each of the first through sixth transistors ST1 through ST6 and the driving transistor DT is a source electrode, the second electrode may be a drain electrode. Alternatively, when the first electrode of each of the first through sixth transistors ST1 through ST6 and the driving transistor DT is a drain electrode, the second electrode may be a source electrode.

An active layer of each of the first through sixth transistors ST1 through ST6 and the driving transistor DT may be made of any one of polysilicon, amorphous silicon, and an oxide semiconductor. Alternatively, the active layers of some of the first through sixth transistors ST1 through ST6 and the driving transistor DT may be made of polysilicon, and the active layers of the other ones may be made of an oxide semiconductor.

In addition, although the first through sixth transistors ST1 through ST6 and the driving transistor DT are formed as P-type metal oxide semiconductor field effect transistors (MOSFETs) in FIG. 28, the present disclosure is not limited thereto, and they may also be formed as N-type MOSFETs.

The first driving voltage of the first driving voltage wiring VDDL, the second driving voltage of the second driving voltage wiring VSSL, and the initialization voltage of the initialization voltage wiring VIL may be set in consideration of characteristics of the driving transistor DT and characteristics of the light emitting element LEL. For example, a difference between the initialization voltage and a data voltage supplied to the source electrode of the driving transistor DT may be set to be smaller (or less) than the threshold voltage of the driving transistor DT.

Figure 29:
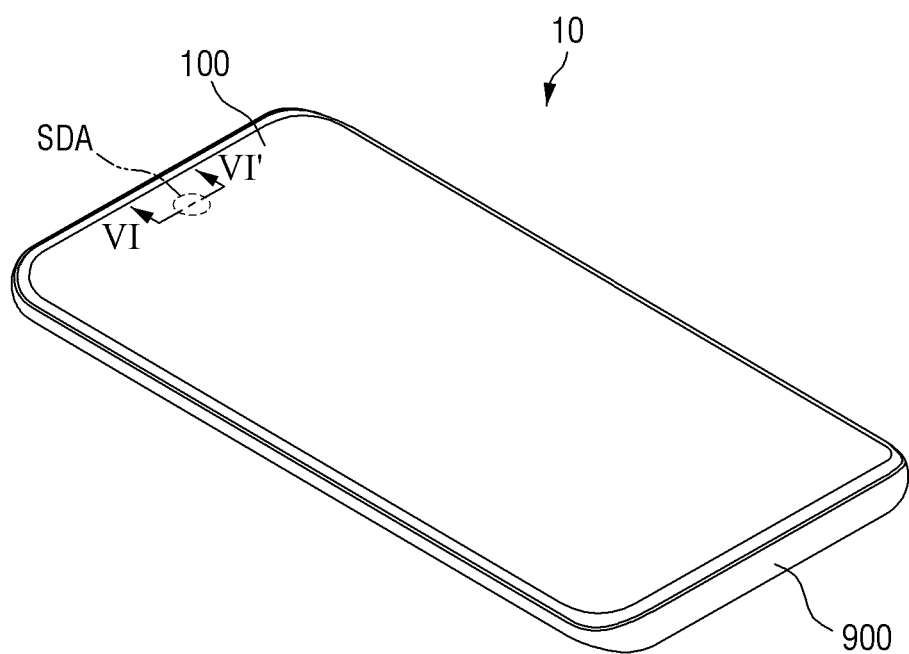
FIG. 29 is a schematic perspective view of a display device according to an embodiment.
Figure 30:
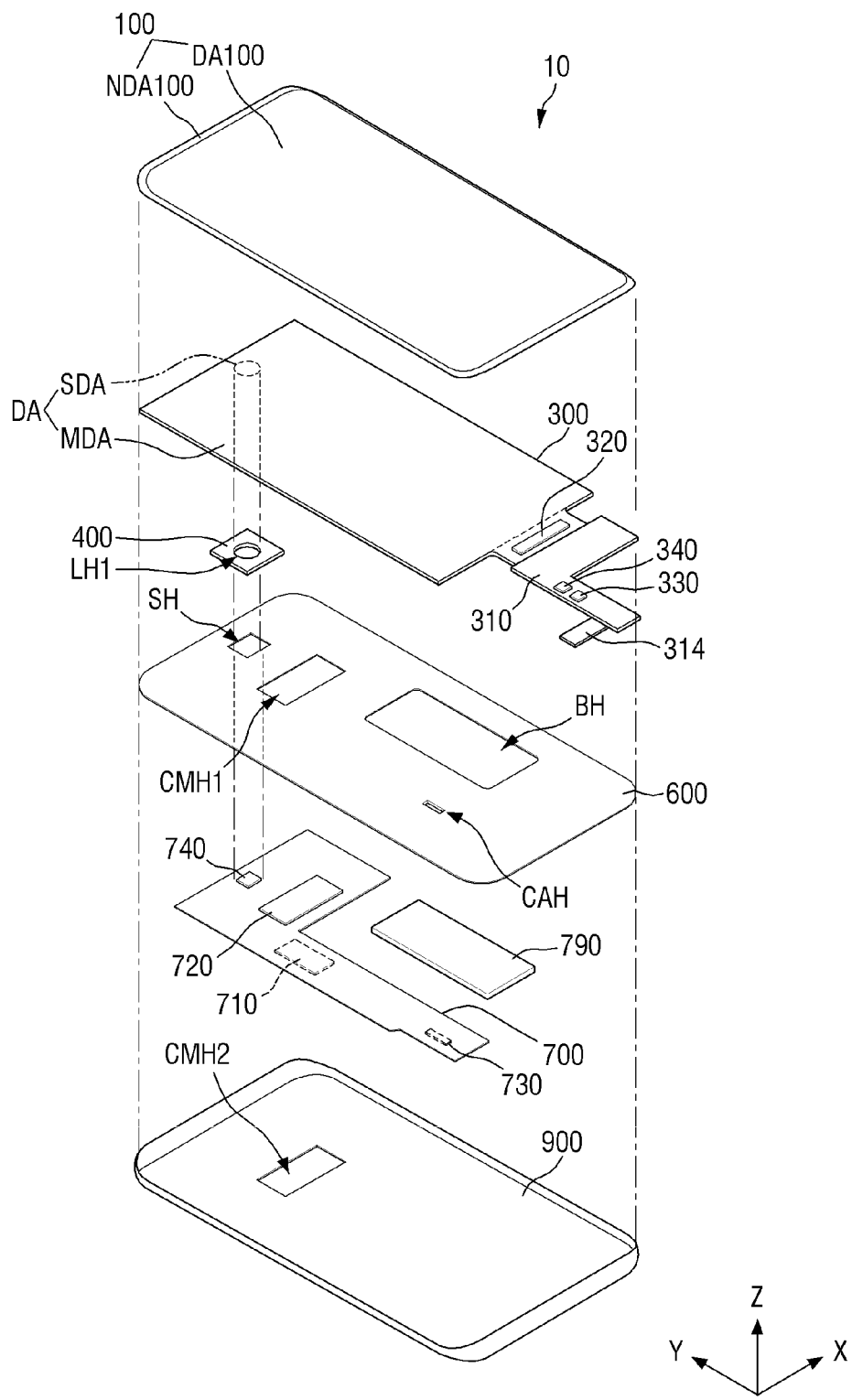
FIG. 30 is an exploded perspective view of the display device according to the embodiment of FIG. 29.
Figure 31:
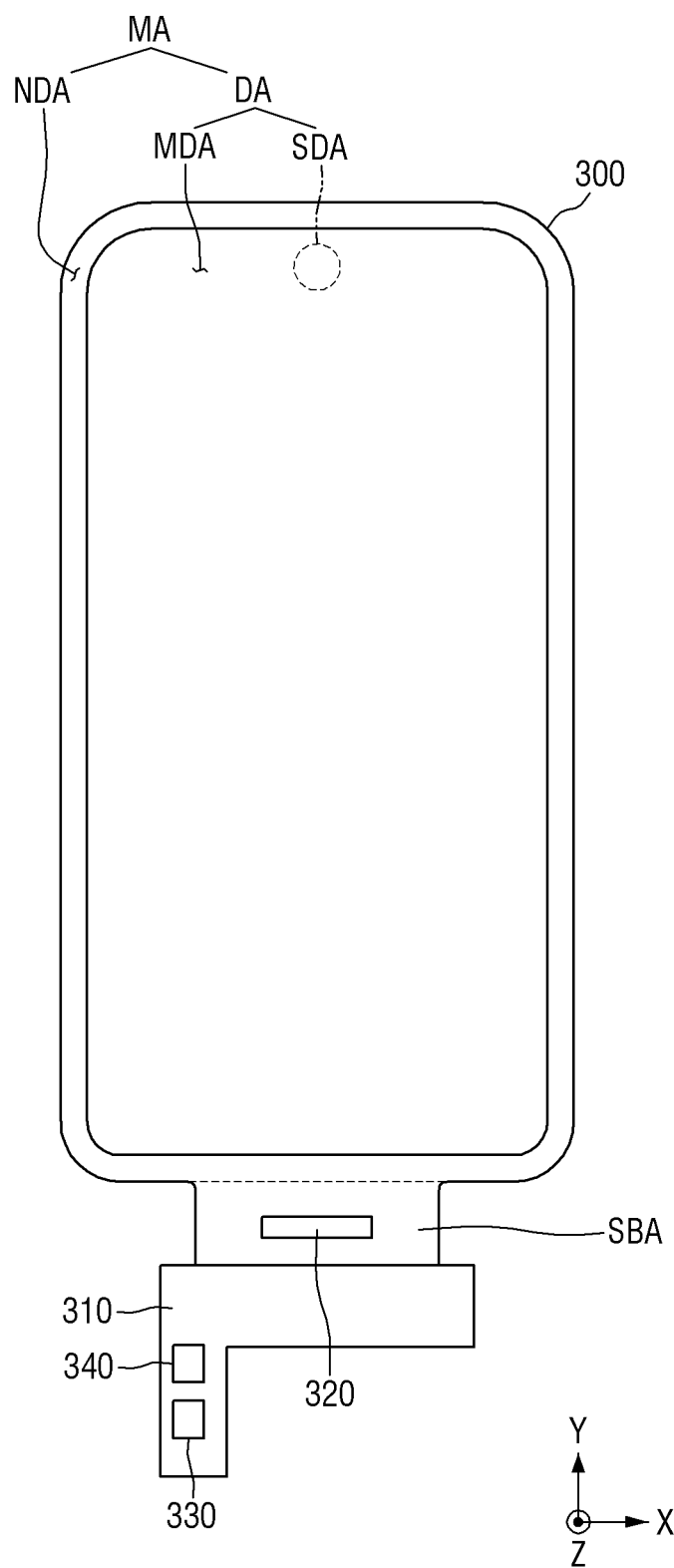
FIG. 31 is a plan view illustrating a display panel, a display circuit board, a display driving circuit, and a touch driving circuit according to an embodiment.

FIG. 29 is a schematic perspective view of a display device 10 according to an embodiment. FIG. 30 is an exploded perspective view of the display device 10 according to the embodiment. FIG. 31 is a plan view illustrating a display panel 300, a display circuit board, a display driving circuit, and a touch driving circuit according to an embodiment.

The embodiment of FIGS. 29-31 is different from the embodiment of FIGS. 1-3 in that the display panel 300 includes a sub-display area SDA instead of a through hole TH.

Referring to FIGS. 29 through 31, a display area DA of the display panel 300 may include a main display area MDA and the sub-display area SDA. The main display area MDA may occupy most of the display area DA.

The main display area MDA may not include a transmissive area that transmits light and may include only a pixel area that includes pixels for displaying an image. On the other hand, the sub-display area SDA may include both a transmissive area that transmits light and a pixel area that includes pixels for displaying an image. That is, the sub-display area SDA may include a transmissive area that is an optical hole through which light can pass. Therefore, light transmittance of the sub-display area SDA may be higher than that of the main display area MDA.

The sub-display area SDA may overlap a sensor hole SH of a bracket 600 and a light sensor 740 in the third direction (Z-axis direction). Thus, light passing through the sub-display area SDA of the display panel 300 may be incident on the light sensor 740 through the sensor hole SH. Therefore, even though the light sensor 740 is disposed under the display panel 300, the light sensor 740 can sense light that is incident on the light sensor 740 from a front surface of the display device 10. For example, the light sensor 740 may sense light reflected by an object disposed on the sub-display area SDA among light emitted from a light emitting device 750.

The sub-display area SDA may be surrounded by the main display area MDA. Alternatively, the sub-display area SDA may be surrounded by a non-display area NDA or may be disposed between the display area DA and the non-display area NDA. In addition, although the sub-display area SDA is disposed at an upper center of the display panel 300 in FIG. 30, the position of the sub-display area SDA is not limited thereto.

In FIGS. 29-31, the display panel 300 includes one sub-display area SDA, but the number of sub-display areas SDA is not limited thereto. When the display panel 300 includes a plurality of sub-display areas SDA, any one of the sub-display areas SDA may overlap the light sensor 740 in the third direction (Z-axis direction), and the other sub-display areas SDA may overlap a sensor device other than the light sensor 740. For example, the sensor device may be a proximity sensor, an illuminance sensor, or a front camera sensor.

In addition, although the sub-display area SDA has a circular planar shape in FIGS. 29-31, the present disclosure is not limited thereto. For example, the sub-display area SDA may also have a polygonal or oval shape.

Figure 32:
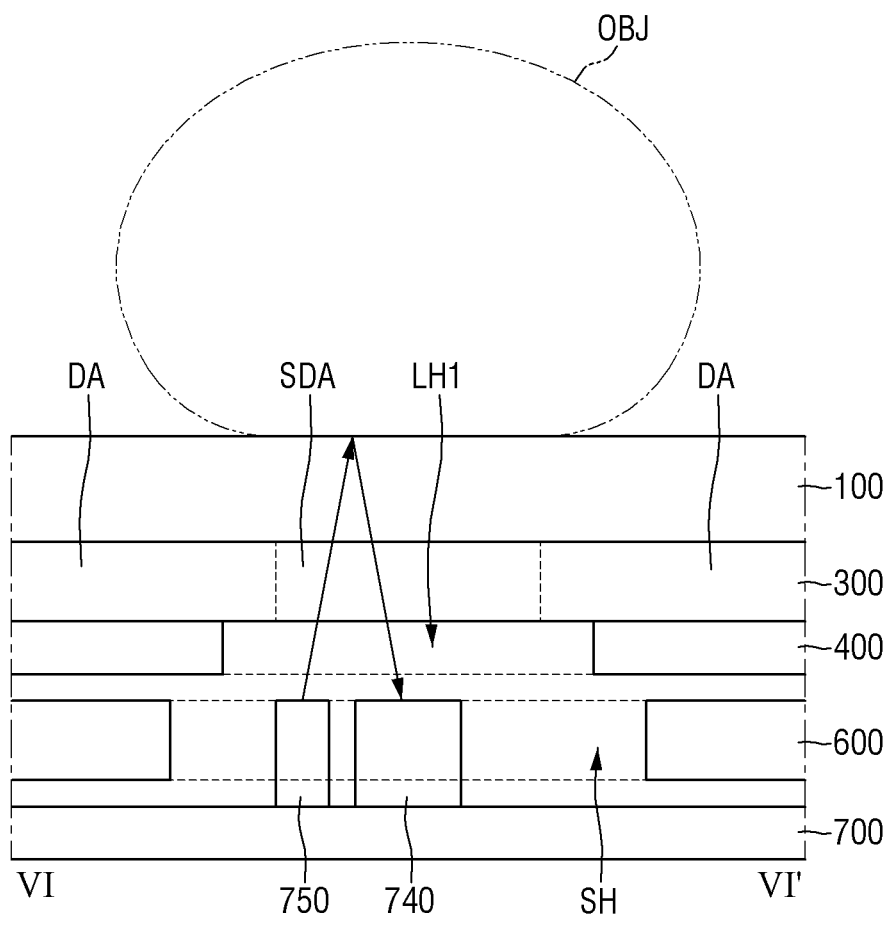
FIG. 32 is a cross-sectional view illustrating a cover window, the display panel, a force sensor, a light emitting device, and a light sensor according to an embodiment.

FIG. 32 is a cross-sectional view illustrating a cover window, the display panel 300, a force sensor 400, the light emitting device 750, and the light sensor 740 according to an embodiment.

In FIG. 32, a cross-section of the display device 10 taken along VI-VI' of FIG. 29 is illustrated. In FIG. 32, a bottom cover 900 is omitted for ease of description.

Figure 33:
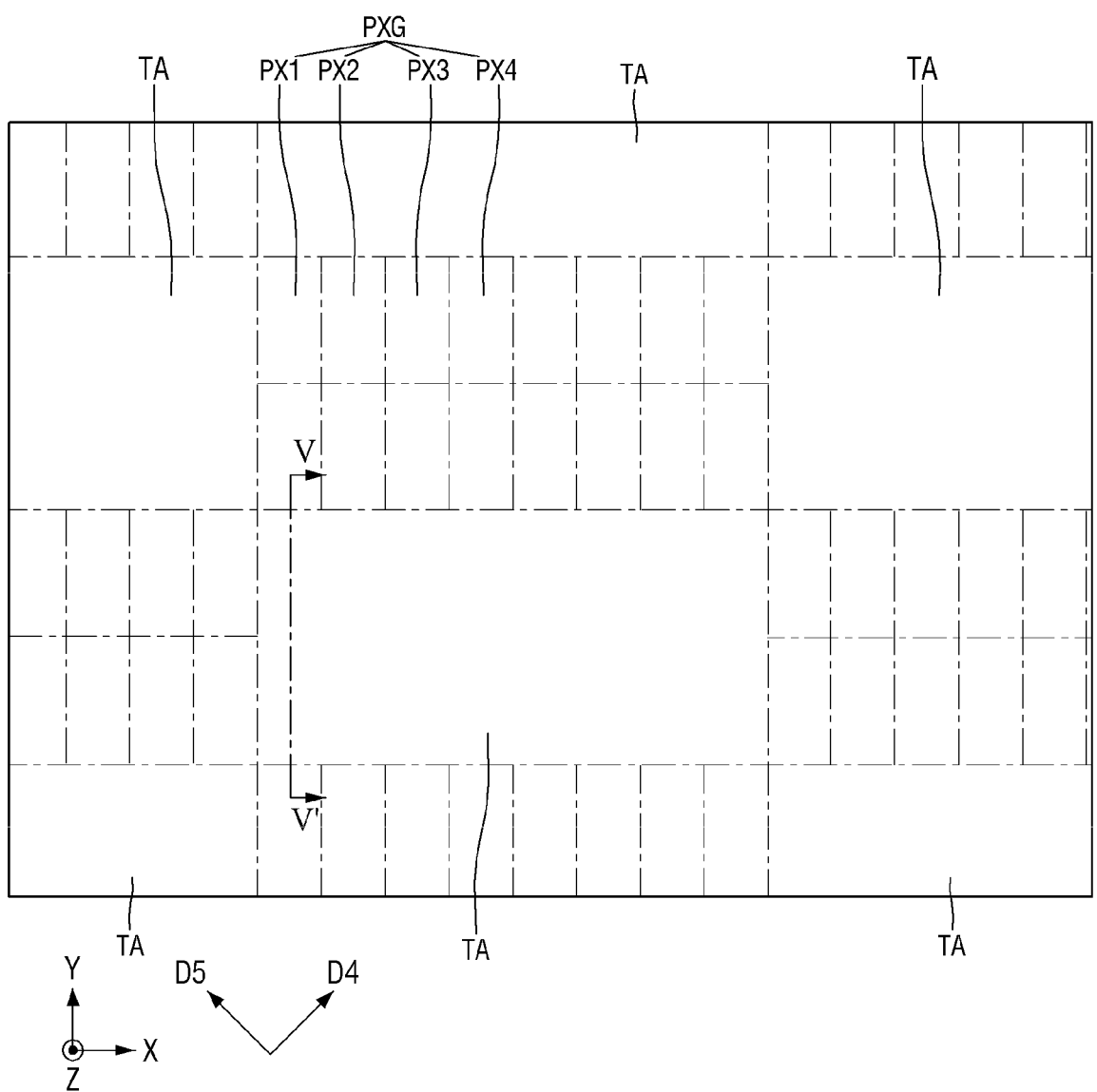
FIG. 33 is a layout view of a sub-display area of a display panel according to an embodiment.

The embodiment of FIG. 32 is different from the embodiment of FIG. 6 in that a through hole TH of the display panel 300 is replaced with the sub-display area SDA having transmissive areas TA (e.g., see FIG. 33).

Referring to FIG. 32, the sub-display area SDA of the display panel 300 may completely overlap a first optical hole LH1 of the force sensor 400. The sub-display area SDA of the display panel 300 may be smaller in size than the first optical hole LH1 of the force sensor 400. A length of the sub-display area SDA in a direction may be smaller (or less) than a length of the first optical hole LH1 in the direction. For example, as illustrated in FIG. 32, a length of the sub-display area SDA in the first direction (X-axis direction) may be smaller (or less) than a length of the first optical hole LH1 in the first direction (X-axis direction). In addition, a length of each transmissive area TA included in the sub-display area SDA in a direction may be smaller (or less) than a length of the first optical hole LH1 in the direction.

In addition, the sub-display area SDA of the display panel 300 may completely overlap the sensor hole SH of the bracket 600. The sub-display area SDA of the display panel 300 may be smaller in size than the sensor hole SH of the bracket 600. A length of the sub-display area SDA in a direction may be smaller (or less) than a length of the sensor hole SH in the direction. For example, as illustrated in FIG. 32, the length of the sub-display area SDA in the first direction (X-axis direction) may be smaller (or less) than a length of the sensor hole SH in the first direction (X-axis direction). Therefore, light passing through the sub-display area SDA, the first optical hole LH1, and the sensor hole SH may be incident on the light sensor 740 overlapped by the sub-display area SDA in the third direction (Z-axis direction).

As illustrated in FIG. 32, light emitted from the light emitting device 750 may be absorbed or reflected by blood vessels of a user's finger OBJ through the first optical hole LH1 of the force sensor 400 and the sub-display area SDA of the display panel 300. The light reflected by the blood vessels of the user's finger OBJ may be sensed by the light sensor 740 through the sub-display area SDA of the display panel 300 and the first optical hole LH1 of the force sensor 400.

In addition, as illustrated in FIG. 17, a bottom panel cover 800 having a second optical hole LH2 may be added on a lower surface of the force sensor 400. In this case, the sub-display area SDA of the display panel 300 may completely overlap the second optical hole LH2 of the bottom panel cover 800. The sub-display area SDA of the display panel 300 may be smaller in size than the second optical hole LH2 of the bottom panel cover 800. A length of the sub-display area SDA in a direction may be smaller (or less) than a length of the second optical hole LH2 in the direction. For example, the length of the sub-display area SDA in the first direction (X-axis direction) may be smaller (or less) than a length of the second optical hole LH2 in the first direction (X-axis direction).

Alternatively, as illustrated in FIG. 18, the force sensor 400 may be formed to be transparent so that light can pass through the force sensor 400. Thus, the first optical hole LH1 may be removed from or may not be present in the force sensor 400.

Alternatively, as illustrated in FIG. 20, the force sensor 400 may be formed to be transparent so that light can pass through the force sensor 400. Thus, the first optical hole LH1 may be removed from or may not be present in the force sensor 400, and the bottom panel cover 800 having the second optical hole LH2 may be added on the lower surface of the force sensor 400.

Alternatively, as illustrated in FIG. 25, the light emitting device 750 may be omitted, and pixels PX of the display panel 300 may emit light in a blood pressure measurement mode instead of the light emitting device 750.

FIG. 33 is a layout view of a sub-display area SDA of a display panel 300 according to an embodiment.

Referring to FIG. 33, the sub-display area SDA may include pixels areas PXA having first through fourth pixels PX1 through PX4 (first pixel PX1, second pixel PX2, third pixel PX3, and fourth pixel PX4) and transmissive areas TA transmitting light.

The pixels areas PXA and the transmissive areas TA may be disposed side by side in the first direction (X-axis direction). The pixel areas PXA and the transmissive areas TA may be alternately disposed in the first direction (X-axis direction). In addition, the pixel areas PXA and the transmissive areas TA may be disposed side by side in the second direction (Y-axis direction). The pixels areas PXA and the transmissive areas TA may be alternately disposed in the second direction (Y-axis direction).

Due to the transmissive areas TA, the number of pixels PX1 through PX4 per unit area in the sub-display area SDA may be smaller (or less) than the number of pixels PX1 through PX4 per unit area in a main display area MDA. In addition, due to the transmissive areas TA, a ratio of the area of the pixels PX1 through PX4 of the sub-display area SDA to the area of the sub-display area SDA may be smaller (or less) than a ratio of the area of the pixels PX1 through PX4 of the main display area MDA to the area of the main display area MDA.

Each of the pixel areas PXA may include I (where I is a positive integer) pixel groups PXG. For example, each of the pixel areas PXA may include four pixel groups PXG. In this case, in each of the pixel areas PXA, two pixel groups PXG may be arranged in the first direction (X-axis direction), and two pixel groups PXG may be arranged in the second direction (Y-axis direction). Each of the pixel groups PXG may include the first through fourth pixels PX1 through PX4.

The transmissive areas TA are areas through which light incident on the display panel 300 passes. The transmissive areas TA do not include the pixels PX1 through PX4. The transmissive areas TA may be surrounded by the pixel areas PXA. To increase light transmittance of the transmissive areas TA, the number of pixels PX1 through PX4 in the sub-display area SDA may be half of the number of pixels PX1 through PX4 in a display area DA excluding the sub-display area SDA. Alternatively, the number of pixels PX1 through PX4 in the sub-display area SDA may be a quarter of the number of pixels PX1 through PX4 in the main display area MDA.

As illustrated in FIG. 32, because the light sensor 740 is overlapped by the sub-display area SDA of the display panel 300, which includes the transmissive areas TA, in the third direction (Z-axis direction), the light sensor 740 can sense light that is incident on the light sensor 740 from a front surface of the display device 10 due to the transmissive areas TA.

Figure 34:
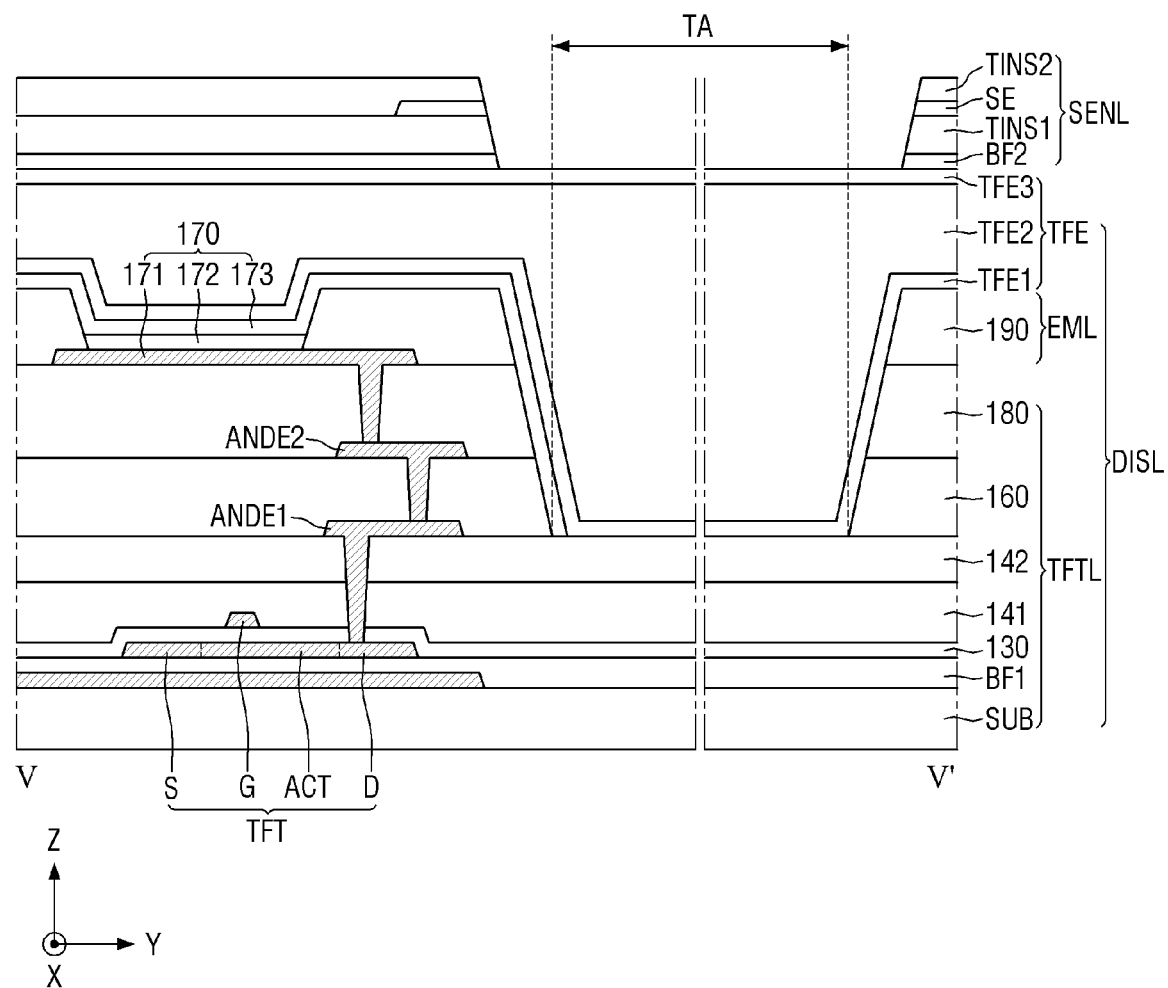
FIG. 34 is a cross-sectional view of an example of the display panel of FIG. 31.

FIG. 34 is a cross-sectional view of an example of the display panel 300 of FIG. 31.

In the embodiment of FIG. 34, a substrate SUB, a thin-film transistor layer TFTL, and a sensor electrode layer SENL formed in the display area DA excluding a transmissive area TA are substantially the same as those described with reference to FIG. 8, and thus a description thereof will be omitted.

Referring to FIG. 34, the transmissive area TA may be an area in which a metal layer of the thin-film transistor layer TFTL, a metal layer of a light emitting element layer EML, and a metal layer of the sensor electrode layer SENL are not disposed to transmit light. Therefore, the transmissive area TA may include a substrate SUB, a buffer layer BF, a gate insulating layer 130, a first interlayer insulating film 141, a second interlayer insulating film 142, a first inorganic layer TFE1, an organic layer TFE2, and a second inorganic layer TFE3.

A first planarization layer 160, a second planarization layer 180, and a bank 190 may be removed from or may not be present in the transmissive area TA. In addition, a part of the transmissive area TA from which the first planarization layer 160, the second planarization layer 180, and the bank 190 have been removed may be filled with or occupied by an encapsulation layer TFE. For example, a part of the transmissive area TA from which the first planarization layer 160, the second planarization layer 180, and the bank 190 have been removed may be filled with or occupied by the first inorganic layer TFE1 and the organic layer TFE2. Therefore, the first inorganic layer TFE1 and the second interlayer insulating film 142 may contact each other in the transmissive area TA.

Although the first planarization layer 160, the second planarization layer 180, and the bank 190 are removed from or not present in the transmissive area TA in FIG. 34, the present disclosure is not limited thereto. For example, at least any one of the first buffer layer BF1, the gate insulating layer 130, the first interlayer insulating film 141, or the second interlayer insulating film 142 may be removed from or not present in the transmissive area TA.

As illustrated in FIG. 34, because an opaque material is not disposed in the transmissive area TA, light passing through the transmissive area TA may be incident on the light sensor 740 overlapped in the third direction (Z-axis direction) by the sub-display area SDA including the transmissive area TA.

Figure 35:
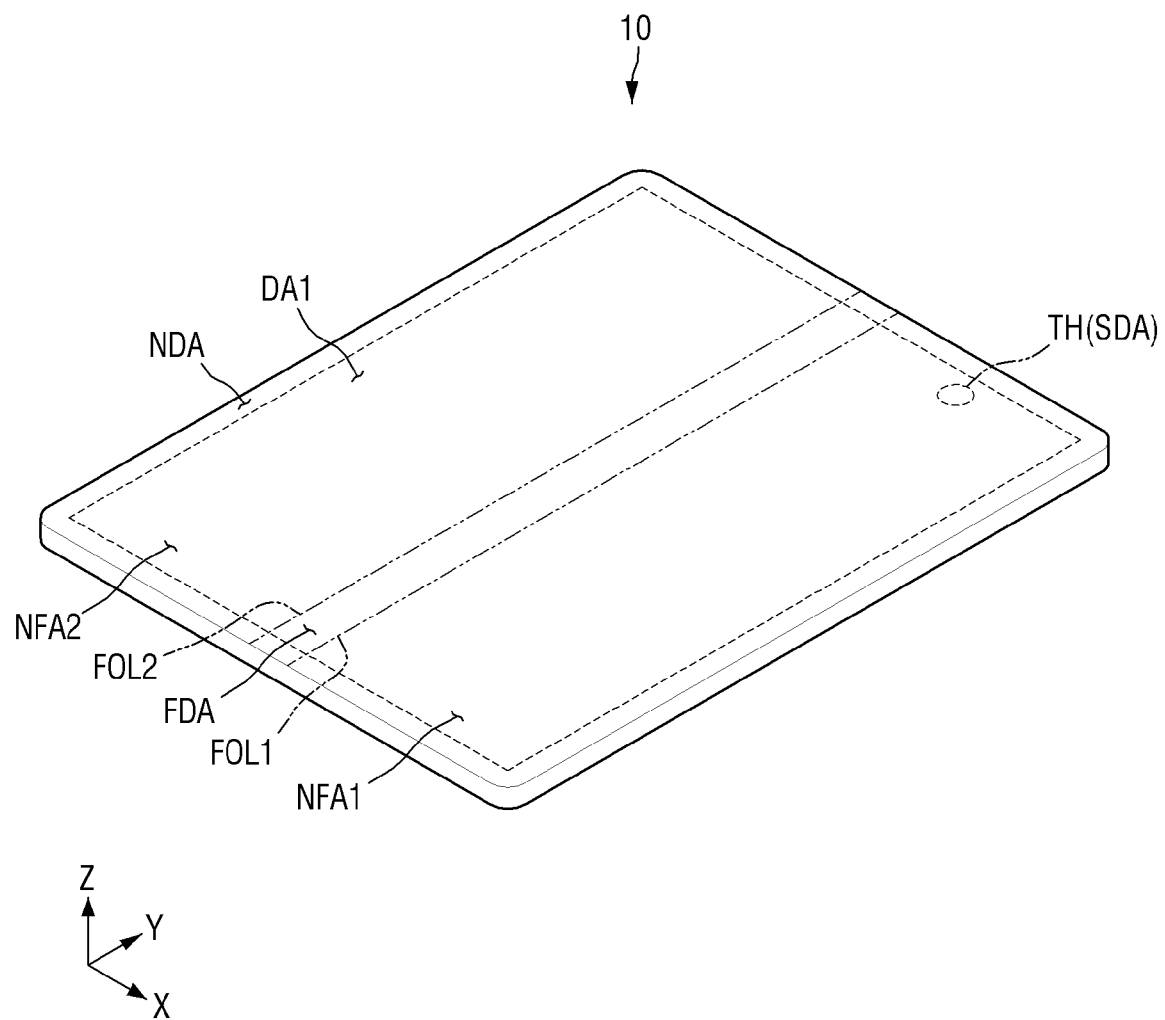
FIGS. 35 and 36 are perspective views of a display device according to an embodiment.
Figure 36:
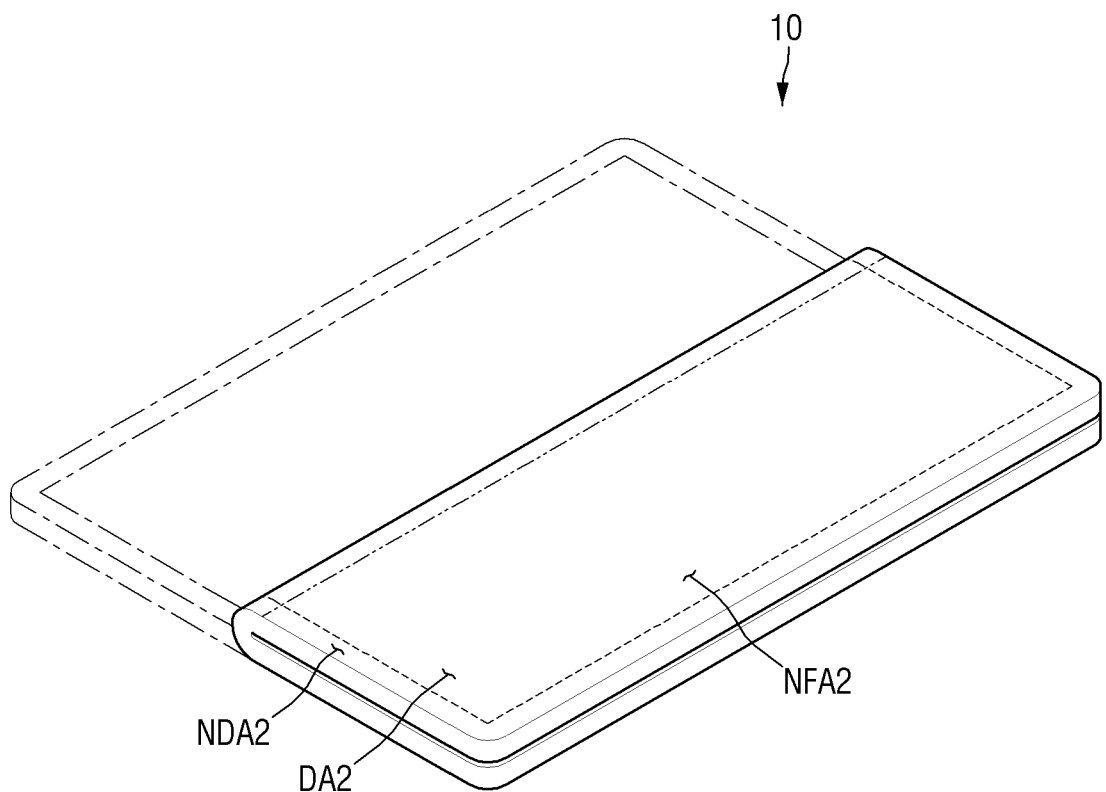

FIGS. 35 and 36 are perspective views of a display device 10 according to an embodiment. In FIGS. 35 and 36, the display device 10 is illustrated as a foldable display device that is folded in the first direction (X-axis direction).

Referring to FIGS. 35 and 36, the display device 10 may maintain both a folded state and an unfolded state. The display device 10 may be folded in an in-folding manner in which its front surface is disposed inside. When the display device 10 is bent or folded in the in-folding manner, parts of the front surface of the display device 10 may face each other. Alternatively, the display device 10 may be folded in an out-folding manner in which its front surface is disposed outside. When the display device 10 is bent or folded in the out-folding manner, parts of a rear surface of the display device 10 may face each other.

A first non-folding area NFA1 may be disposed on a side (e.g., a right side of a folding area FDA). A second non-folding area NFA2 may be disposed on the other side (e.g., a left side of the folding area FDA).

A first folding line FOL1 and a second folding line FOL2 may extend in the second direction (Y-axis direction), and the display device 10 may be folded in the first direction (X-axis direction). Therefore, because a length of the display device 10 in the first direction (X-axis direction) can be reduced to about half, a user may more easily carry the display device 10.

The first folding line FOL1 and the second folding line FOL2 may not necessarily extend in the second direction (Y-axis direction). For example, the first folding line FOL1 and the second folding line FOL2 may extend in the first direction (X-axis direction), and the display device 10 may be folded in the second direction (Y-axis direction). In this case, a length of the display device 10 in the second direction (Y-axis direction) may be reduced to about half. Alternatively, the first folding line FOL1 and the second folding line FOL2 may extend in a diagonal direction of the display device 10 between the first direction (X-axis direction) and the second direction (Y-axis direction). In this case, the display device 10 may be folded in a triangular shape.

When the first folding line FOL1 and the second folding line FOL2 extend in the second direction (Y-axis direction), a length of the folding area FDA may be smaller (or less) in the first direction (X-axis direction) than in the second direction (Y-axis direction). In addition, a length of the first non-folding area NFA1 in the first direction (X-axis direction) may be greater than the length of the folding area FDA in the first direction (X-axis direction). A length of the second non-folding area NFA2 in the first direction (X-axis direction) may be greater than the length of the folding area FDA in the first direction (X-axis direction).

A first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed in a forward direction on the folding area FDA, the first non-folding area NFA1, and the second non-folding area NFA2 of the display device 10.

A second display area DA2 may be disposed on the rear surface of the display device 10. The second display area DA2 may overlap the second non-folding area NFA2. Therefore, when the display device 10 is folded, an image may be displayed in the forward direction on the second non-folding area NFA2 of the display device 10.

Although a through hole TH or a sub-display area SDA is disposed in the first non-folding area NFA1 in FIGS. 35 and 36, the present disclosure is not limited thereto. The through hole TH or the sub-display area SDA may also be disposed in the second non-folding area NFA2 or the folding area FDA.

Figure 37:
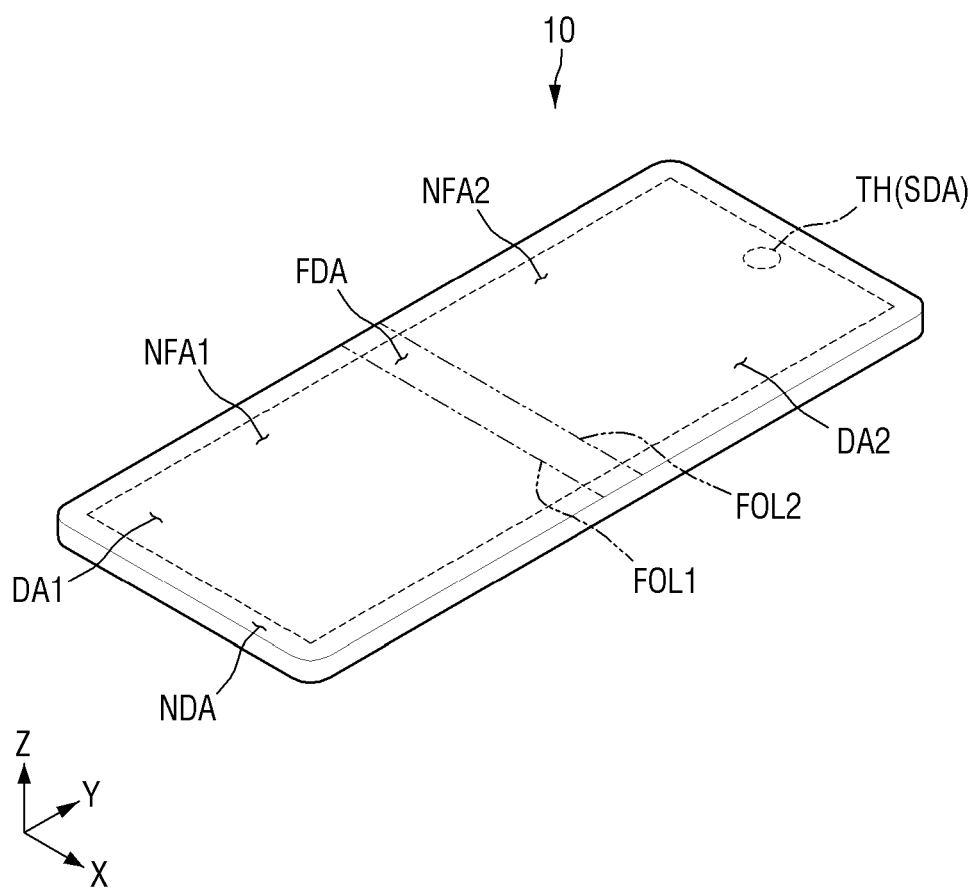
FIGS. 37 and 38 are perspective views of a display device according to an embodiment.
Figure 38:
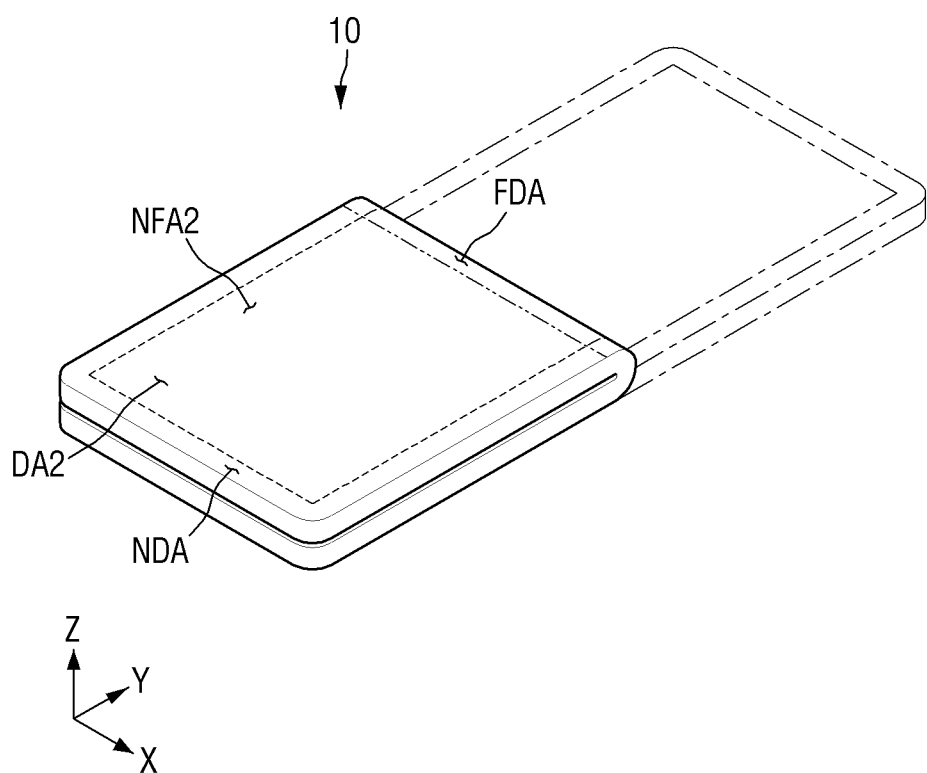

FIGS. 37 and 38 are perspective views of a display device 10 according to an embodiment. In FIGS. 37 and 38, the display device 10 is illustrated as a foldable display device that is folded in the second direction (Y-axis direction).

Referring to FIGS. 37 and 38, the display device 10 may maintain both a folded state and an unfolded state. The display device 10 may be folded in an in-folding manner in which its front surface is disposed inside. When the display device 10 is bent or folded in the in-folding manner, parts of the front surface of the display device 10 may face each other. Alternatively, the display device 10 may be folded in an out-folding manner in which its front surface is disposed outside. When the display device 10 is bent or folded in the out-folding manner, parts of a rear surface of the display device 10 may face each other.

The display device 10 may include a folding area FDA, a first non-folding area NFA1, and a second non-folding area NFA2. The folding area FDA may be an area where the display device 10 is folded, and the first non-folding area NFA1 and the second non-folding area NFA2 may be areas where the display device 10 is not folded.

The first non-folding area NFA1 may be disposed on a side (e.g., a lower side) of the folding area FDA. The second non-folding area NFA2 may be disposed on the other side (e.g., an upper side of the folding area FDA). The folding area FDA may be an area that is bent with a set (e.g., predetermined) curvature along a first folding line FOL1 and a second folding line FOL2. Therefore, the first folding line FOL1 may be a boundary between the folding area FDA and the first non-folding area NFA1, and the second folding line FOL2 may be a boundary between the folding area FDA and the second non-folding area NFA2.

The first folding line FOL1 and the second folding line FOL2 may extend in the first direction (X-axis direction) as illustrated in FIGS. 37 and 38, and the display device 10 may be folded in the second direction (Y-axis direction). Therefore, because a length of the display device 10 in the second direction (Y-axis direction) can be reduced to about half, a user may more easily carry the display device 10.

The first folding line FOL1 and the second folding line FOL2 may not necessarily extend in the first direction (X-axis direction). For example, the first folding line FOL1 and the second folding line FOL2 may extend in the second direction (Y-axis direction), and the display device 10 may be folded in the first direction (X-axis direction). In this case, a length of the display device 10 in the first direction (X-axis direction) may be reduced to about half. Alternatively, the first folding line FOL1 and the second folding line FOL2 may extend in the diagonal direction of the display device 10 between the first direction (X-axis direction) and the second direction (Y-axis direction). In this case, the display device 10 may be folded in a triangular shape.

When the first folding line FOL1 and the second folding line FOL2 extend in the first direction (X-axis direction) as illustrated in FIGS. 37 and 38, a length of the folding area FDA may be smaller (or less) in the second direction (Y-axis direction) than in the first direction (X-axis direction). In addition, a length of the first non-folding area NFA1 in the second direction (Y-axis direction) may be greater than the length of the folding area FDA in the second direction (Y-axis direction). A length of the second non-folding area NFA2 in the second direction (Y-axis direction) may be greater than the length of the folding area FDA in the second direction (Y-axis direction).

A first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed in the forward direction on the folding area FDA, the first non-folding area NFA1, and the second non-folding area NFA2 of the display device 10.

A second display area DA2 may be disposed on the rear surface of the display device 10. The second display area DA2 may overlap the second non-folding area NFA2. Therefore, when the display device 10 is folded, an image may be displayed in the forward direction on the second non-folding area NFA2 of the display device 10.

Although a through hole TH or a sub-display area SDA is disposed in the second non-folding area NFA2 in FIGS. 37 and 38, the present disclosure is not limited thereto. The through hole TH or the sub-display area SDA may also be disposed in the first non-folding area NFA1 or the folding area FDA.

Although some embodiments of the present disclosure have been disclosed for illustrative purposes, those skilled in the art will appreciate that various modifications, additions and substitutions are possible, without departing from the scope and spirit of the disclosure as defined by the accompanying claims and equivalents thereof.

What is claimed is:

1. A display device comprising:
    a display panel comprising a through hole and a pixel area, the pixel area surrounding the through hole and including pixels to display an image;
    a force sensor at a first surface of the display panel and configured to sense force applied from an outside; and
    a light sensor overlapping the through hole of the display panel in a thickness direction of the display panel, the light sensor being configured to sense light incident on the light sensor through the through hole,
wherein the force sensor comprises a first optical hole overlapping the through hole in the thickness direction of the display panel.

2. The display device of claim 1, wherein a length of the through hole in a direction is less than a length of the first optical hole in the direction.

3. The display device of claim 1, further comprising a light emitting device overlapping the through hole of the display panel in the thickness direction of the display panel and configured to emit light.

4. The display device of claim 3, further comprising a main circuit board at a surface of the force sensor, wherein the light sensor and the light emitting device are mounted on the main circuit board.

5. The display device of claim 3, wherein the light sensor is configured to sense, through the through hole, light reflected by an object from among light emitted from the light emitting device, the object being at a second surface of the display panel opposite the first surface of the display panel.

6. The display device of claim 5, wherein the light emitting device is configured to emit infrared light, red-wavelength light, or green-wavelength light.

7. The display device of claim 1, wherein the force sensor comprises:
a first base substrate and a second base substrate facing each other;
a first force electrode on the first base substrate;
a second force electrode on the second base substrate; and
a force sensing layer overlapping the first force electrode and the second force electrode in a thickness direction of the first base substrate.

8. The display device of claim 7, wherein the first force electrode and the second force electrode comprise an opaque conductive material.

9. The display device of claim 7, wherein the first force electrode and the second force electrode comprise a transparent conductive material.

10. The display device of claim 1, wherein the light sensor is configured to sense, through the through hole, light reflected by an object from among light emitted from the pixels, the object being at a second surface of the display panel opposite the first surface of the display panel.

11. The display device of claim 10, wherein light emitted from the pixels in a display mode to display an image has lower luminance than light emitted from the pixels in a blood pressure measurement mode in which the light reflected by the object is sensed by the light sensor.

12. The display device of claim 11, wherein the pixels are configured to emit infrared light, red-wavelength light, or green-wavelength light in the blood pressure measurement mode in which the light reflected by the object is sensed by the light sensor.

13. The display device of claim 11, wherein pixels disposed adjacent to the through hole are configured to emit light in the blood pressure measurement mode.

14. The display device of claim 1, wherein the display panel comprises a display layer and a touch electrode layer on the display layer.

15. A display device comprising:
a display panel comprising a through hole and a pixel area, the pixel area surrounding the through hole and including pixels to display an image;
a force sensor at a first surface of the display panel and configured to sense force applied from an outside;
a light sensor overlapping the through hole of the display panel in a thickness direction of the display panel, the light sensor being configured to sense light incident on the light sensor through the through hole; and
a bottom panel cover on a surface of the force sensor, the bottom panel cover comprising a second optical hole overlapping the through hole of the display panel in the thickness direction of the display panel and configured to protect the display panel.

16. The display device of claim 15, wherein a length of the through hole in a direction is less than a length of the second optical hole in the direction.

17. A display device comprising:
a display panel comprising a pixel area and a transmissive area adjacent to the pixel area, the pixel area comprising pixels to display an image;
a force sensor at a surface of the display panel and configured to sense force applied from an outside; and
a light sensor overlapping the transmissive area of the display panel in a thickness direction of the display panel and configured to sense light incident on the light sensor through the transmissive area,
wherein the force sensor comprises a first optical hole overlapping the transmissive area in the thickness direction of the display panel.

18. The display device of claim 17, wherein a length of the first optical hole in a direction is greater than a length of the transmissive area in the direction.

19. The display device of claim 17, further comprising a main circuit board at a surface of the force sensor, wherein the light sensor is mounted on the main circuit board.

20. The display device of claim 17, wherein the display panel comprises a display layer and a touch electrode layer on the display layer.

* * * * *